(12) United States Patent
Laal et al.

(10) Patent No.: US 7,807,182 B2
(45) Date of Patent: Oct. 5, 2010

(54) EARLY DETECTION OF MYCOBACTERIAL DISEASE USING PEPTIDES

(75) Inventors: Suman Laal, Croton-on-Hudson, NY (US); Susan Zolla-Pazner, New York, NY (US); John T. Belisle, Fort Collins, CO (US)

(73) Assignees: Colorado State University Research Foundation, Fort Collins, CO (US); New York University, New York, NY (US)

( * ) Notice: Subject to any disclaimer, the term of this patent is extended or adjusted under 35 U.S.C. 154(b) by 2560 days.

(21) Appl. No.: 10/210,884

(22) Filed: Aug. 2, 2002

(65) Prior Publication Data

US 2009/0280140 A1 Nov. 12, 2009

Related U.S. Application Data

(63) Continuation-in-part of application No. 09/396,347, filed on Sep. 14, 1999, now Pat. No. 6,506,384, which is a continuation-in-part of application No. 09/001,984, filed on Dec. 31, 1997, now Pat. No. 6,245,331.

(60) Provisional application No. 60/309,185, filed on Aug. 2, 2001, provisional application No. 60/034,003, filed on Dec. 31, 1996.

(51) Int. Cl.
*A61K 39/04* (2006.01)
*A61K 39/38* (2006.01)
*A61K 39/02* (2006.01)

(52) U.S. Cl. .................... 424/248.1; 424/9.1; 424/9.2; 424/130.1; 424/164.1; 424/168.1; 424/184.1; 424/185.1; 424/234.1; 435/7.1; 435/7.2; 530/300; 530/350

(58) Field of Classification Search ................. 424/9.1, 424/9.2, 130.1, 164.1, 168.1, 184.1, 185.1, 424/234.1, 248.1; 435/7.1, 7.2; 530/300, 530/350
See application file for complete search history.

(56) References Cited

U.S. PATENT DOCUMENTS

| 5,254,459 | A | 10/1993 | Patarroyo |
| 5,330,754 | A | 7/1994 | Kapoor et al. |

FOREIGN PATENT DOCUMENTS

| WO | WO90/04041 | 4/1990 |
| WO | WO92/08809 | 5/1992 |
| WO | WO97/34149 | 9/1997 |

OTHER PUBLICATIONS

E. O. E. Bassey et al., "Candidate Antigens for Improved Serodiagnosis of Tuberculosis," Tubercle and Lung Disease, 1996, pp. 136-145, vol. 77.

*Primary Examiner*—Rodney P. Swartz
(74) *Attorney, Agent, or Firm*—Browdy and Neimark, PLLC

(57) ABSTRACT

A number of protein and glycoprotein antigens secreted by *Mycobacterium tuberculosis* (Mtb) have been identified as "early" Mtb antigens on the basis early antibodies present in subjects infected with Mtb prior to the development of detectable clinical disease. Epitope-bearing peptide fragments of these early Mtb antigens, in particular of an 88 kDa secreted protein, GlcB (SEQ ID NO:106) and of Mtb antigen MPT51 (SEQ ID NO:107) have been identified. These peptides, variants thereof, peptide multimers thereof that include two or more repeats of one or more of the peptides, and fusion polypeptides that include early Mtb antigenic proteins, peptides or both, are useful in immunoassay methods for early, rapid detection of TB in a subject. Preferred immunoassays detect the antibodies in the subject's urine. Also provided are antigenic compositions, kits and methods to useful for detecting an early Mtb antibodies. The antigenic proteins and peptides are also used in vaccine compositions.

24 Claims, 5 Drawing Sheets

SEQUENCE LISTING

<160> NUMBER OF SEQ ID NOS: 238

<210> SEQ ID NO 1
<211> LENGTH: 39
<212> TYPE: PRT
<213> ORGANISM: Mycobacterium tuberculosis

<400> SEQUENCE: 1

Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Ala Asn
            20                  25                  30

Ser Pro Ala Leu Tyr Leu Leu
        35

<210> SEQ ID NO 2
<211> LENGTH: 39
<212> TYPE: PRT
<213> ORGANISM: Mycobacterium tuberculosis

<400> SEQUENCE: 2

Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Asn Asn
            20                  25                  30

Ser Pro Ala Val Tyr Leu Leu
        35

<210> SEQ ID NO 3
<211> LENGTH: 37
<212> TYPE: PRT
<213> ORGANISM: Mycobacterium tuberculosis

<400> SEQUENCE: 3

```
Phe Ser Arg Pro Gly Leu Pro Val Glu Tyr Leu Gln Val Pro Ser Ala
1               5                   10                  15

Ser Met Gly Arg Asp Ile Lys Val Gln Phe Gln Gly Gly Pro His
            20                  25                  30

Ala Val Tyr Leu Leu
            35

<210> SEQ ID NO 4
<211> LENGTH: 32
<212> TYPE: PRT
<213> ORGANISM: Mycobacterium tuberculosis

<400> SEQUENCE: 4

Ala Pro Tyr Glu Asn Leu Met Val Pro Ser Pro Ser Met Gly Arg Asp
1               5                   10                  15

Ile Pro Val Ala Phe Leu Ala Gly Gly Pro His Ala Val Tyr Leu Leu
            20                  25                  30

<210> SEQ ID NO 5
<211> LENGTH: 12
<212> TYPE: PRT
<213> ORGANISM: Mycobacterium tuberculosis

<400> SEQUENCE: 5

Asp Pro Glu Pro Ala Pro Pro Val Pro Thr Thr Ala
1               5                   10

<210> SEQ ID NO 6
<211> LENGTH: 26
<212> TYPE: PRT
<213> ORGANISM: Mycobacterium tuberculosis

<400> SEQUENCE: 6

Ala Pro Tyr Glu Leu Asn Ile Thr Ser Ala Thr Tyr Gln Ser Ala Ile
1               5                   10                  15

Pro Pro Arg Gly Thr Gln Ala Val Val Leu
            20                  25

<210> SEQ ID NO 7
<211> LENGTH: 11
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be any amino acid

<400> SEQUENCE: 7

Xaa Pro Val Ala Pro Pro Pro Pro Ala Ala Ala
1               5                   10

<210> SEQ ID NO 8
<211> LENGTH: 13
<212> TYPE: PRT
<213> ORGANISM: Mycobacterium tuberculosis
<220> FEATURE:
<221> NAME/KEY: MISC_FEATURE
<222> LOCATION: (9)..(9)
<223> OTHER INFORMATION: Xaa can be any amino acid

<400> SEQUENCE: 8

Gly Glu Val Ala Pro Thr Pro Thr Xaa Pro Thr Pro Gln
1               5                   10
```

```
<210> SEQ ID NO 9
<211> LENGTH: 13
<212> TYPE: PRT
<213> ORGANISM: Mycobacterium tuberculosis

<400> SEQUENCE: 9

Gly Glu Val Ala Pro Thr Pro Thr Thr Pro Thr Pro Gln
1               5                   10

<210> SEQ ID NO 10
<211> LENGTH: 7
<212> TYPE: PRT
<213> ORGANISM: Mycobacterium tuberculosis
<220> FEATURE:
<221> NAME/KEY: MISC_FEATURE
<222> LOCATION: (6)..(6)
<223> OTHER INFORMATION: Xaa can be any amino acid

<400> SEQUENCE: 10

Ala Ser Pro Pro Ser Xaa Ala
1               5

<210> SEQ ID NO 11
<211> LENGTH: 35
<212> TYPE: PRT
<213> ORGANISM: Mycobacterium tuberculosis

<400> SEQUENCE: 11

Val Ala Pro Pro Pro Ala Pro Ala Pro Ala Pro Ala Glu Pro Ala Pro
1               5                   10                  15

Ala Pro Ala Pro Ala Gly Glu Val Ala Pro Thr Pro Thr Thr Pro Thr
            20                  25                  30

Pro Gln Arg
        35

<210> SEQ ID NO 12
<211> LENGTH: 7
<212> TYPE: PRT
<213> ORGANISM: Mycobacterium tuberculosis
<220> FEATURE:
<221> NAME/KEY: MISC_FEATURE
<222> LOCATION: (6)..(6)
<223> OTHER INFORMATION: Xaa can be any amino acid

<400> SEQUENCE: 12

Ala Ser Pro Pro Ser Xaa Ala
1               5

<210> SEQ ID NO 13
<211> LENGTH: 10
<212> TYPE: PRT
<213> ORGANISM: Mycobacterium tuberculosis

<400> SEQUENCE: 13

Asn Asn Pro Val Asp Lys Gly Ala Ala Lys
1               5                   10

<210> SEQ ID NO 14
<211> LENGTH: 6
<212> TYPE: PRT
<213> ORGANISM: Mycobacterium tuberculosis

<400> SEQUENCE: 14

Asp Thr Arg Ile Val Leu
1               5
```

```
<210> SEQ ID NO 15
<211> LENGTH: 7
<212> TYPE: PRT
<213> ORGANISM: Mycobacterium tuberculosis

<400> SEQUENCE: 15

Ala Ala Pro Pro Ala Pro Ala
1               5

<210> SEQ ID NO 16
<211> LENGTH: 9
<212> TYPE: PRT
<213> ORGANISM: Mycobacterium tuberculosis

<400> SEQUENCE: 16

Gly Trp Val Glu Ser Asp Ala Ala His
1               5

<210> SEQ ID NO 17
<211> LENGTH: 9
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be any amino acid

<400> SEQUENCE: 17

Xaa Pro Val Ala Pro Pro Pro Pro Ala
1               5

<210> SEQ ID NO 18
<211> LENGTH: 11
<212> TYPE: PRT
<213> ORGANISM: Mycobacterium tuberculosis

<400> SEQUENCE: 18

Thr Asp Ser Lys Ala Ala Ala Arg Leu Gly Ser
1               5                   10

<210> SEQ ID NO 19
<211> LENGTH: 16
<212> TYPE: PRT
<213> ORGANISM: Mycobacterium tuberculosis

<400> SEQUENCE: 19

Gly Ser Ala Leu Leu Ala Lys Thr Thr Gly Asp Pro Pro Phe Pro Gly
1               5                   10                  15

<210> SEQ ID NO 20
<211> LENGTH: 13
<212> TYPE: PRT
<213> ORGANISM: Mycobacterium tuberculosis
<220> FEATURE:
<221> NAME/KEY: MISC_FEATURE
<222> LOCATION: (9)..(9)
<223> OTHER INFORMATION: Xaa can be any amino acid

<400> SEQUENCE: 20

Gly Glu Val Ala Pro Thr Pro Thr Xaa Pro Thr Pro Gln
1               5                   10

<210> SEQ ID NO 21
<211> LENGTH: 5
<212> TYPE: PRT
<213> ORGANISM: Mycobacterium tuberculosis
```

-continued

```
<400> SEQUENCE: 21

Leu Pro Ala Gly Trp
1               5

<210> SEQ ID NO 22
<211> LENGTH: 5
<212> TYPE: PRT
<213> ORGANISM: Mycobacterium tuberculosis

<400> SEQUENCE: 22

Ile Val Leu Gly Arg
1               5

<210> SEQ ID NO 23
<211> LENGTH: 11
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be any amino acid

<400> SEQUENCE: 23

Xaa Pro Val Ala Pro Pro Pro Ala Ala Ala
1               5                   10

<210> SEQ ID NO 24
<211> LENGTH: 5
<212> TYPE: PRT
<213> ORGANISM: Mycobacterium tuberculosis

<400> SEQUENCE: 24

Tyr Tyr Glu Val Lys
1               5

<210> SEQ ID NO 25
<211> LENGTH: 13
<212> TYPE: PRT
<213> ORGANISM: Mycobacterium tuberculosis

<400> SEQUENCE: 25

Gly Glu Val Ala Pro Thr Pro Thr Thr Pro Thr Pro Gln
1               5                   10

<210> SEQ ID NO 26
<211> LENGTH: 11
<212> TYPE: PRT
<213> ORGANISM: Mycobacterium tuberculosis

<400> SEQUENCE: 26

Ala Ala Asn Thr Pro Asn Ala Gln Pro Gly Asp
1               5                   10

<210> SEQ ID NO 27
<211> LENGTH: 13
<212> TYPE: PRT
<213> ORGANISM: Mycobacterium tuberculosis

<400> SEQUENCE: 27

Leu Asp Ala Asn Gly Val Ser Gly Ser Ala Ser Tyr Tyr
1               5                   10

<210> SEQ ID NO 28
<211> LENGTH: 13
```

```
<212> TYPE: PRT
<213> ORGANISM: Mycobacterium tuberculosis

<400> SEQUENCE: 28

Glu Val Lys Phe Ser Asp Pro Ser Lys Pro Asn Gly Gln
1               5                   10

<210> SEQ ID NO 29
<211> LENGTH: 12
<212> TYPE: PRT
<213> ORGANISM: Mycobacterium tuberculosis
<220> FEATURE:
<221> NAME/KEY: MISC_FEATURE
<222> LOCATION: (10)..(10)
<223> OTHER INFORMATION: Xaa can be any amino acid

<400> SEQUENCE: 29

Asp Pro Glu Pro Ala Pro Pro Val Pro Xaa Thr Ala
1               5                   10

<210> SEQ ID NO 30
<211> LENGTH: 8
<212> TYPE: PRT
<213> ORGANISM: Mycobacterium tuberculosis

<400> SEQUENCE: 30

Thr Gly Val Ile Gly Ser Pro Ala
1               5

<210> SEQ ID NO 31
<211> LENGTH: 16
<212> TYPE: PRT
<213> ORGANISM: Mycobacterium tuberculosis

<400> SEQUENCE: 31

Phe Val Val Trp Leu Gly Thr Ala Asn Asn Pro Val Asp Lys Gly Ala
1               5                   10                  15

<210> SEQ ID NO 32
<211> LENGTH: 13
<212> TYPE: PRT
<213> ORGANISM: Mycobacterium tuberculosis

<400> SEQUENCE: 32

Gly Arg Leu Asp Gln Lys Leu Tyr Ala Ser Ala Glu Ala
1               5                   10

<210> SEQ ID NO 33
<211> LENGTH: 8
<212> TYPE: PRT
<213> ORGANISM: Mycobacterium tuberculosis

<400> SEQUENCE: 33

Tyr Met Pro Tyr Pro Gly Thr Arg
1               5

<210> SEQ ID NO 34
<211> LENGTH: 10
<212> TYPE: PRT
<213> ORGANISM: Mycobacterium tuberculosis

<400> SEQUENCE: 34

Pro Asn Ala Pro Pro Pro Pro Val Ile Ala
1               5                   10
```

-continued

```
<210> SEQ ID NO 35
<211> LENGTH: 6
<212> TYPE: PRT
<213> ORGANISM: Mycobacterium tuberculosis

<400> SEQUENCE: 35

Gln Glu Thr Val Ser Leu
1               5

<210> SEQ ID NO 36
<211> LENGTH: 16
<212> TYPE: PRT
<213> ORGANISM: Mycobacterium tuberculosis

<400> SEQUENCE: 36

Val Ile Gly Ser Pro Ala Ala Asn Ala Pro Asp Ala Gly Pro Pro Gln
1               5                   10                  15

<210> SEQ ID NO 37
<211> LENGTH: 6
<212> TYPE: PRT
<213> ORGANISM: Mycobacterium tuberculosis

<400> SEQUENCE: 37

Gly Gly Phe Ser Phe Ala
1               5

<210> SEQ ID NO 38
<211> LENGTH: 7
<212> TYPE: PRT
<213> ORGANISM: Mycobacterium tuberculosis

<400> SEQUENCE: 38

Ala Glu Ser Ile Arg Pro Leu
1               5

<210> SEQ ID NO 39
<211> LENGTH: 9
<212> TYPE: PRT
<213> ORGANISM: Mycobacterium tuberculosis

<400> SEQUENCE: 39

Asn Gly Val Ser Gly Ser Ala Ser Tyr
1               5

<210> SEQ ID NO 40
<211> LENGTH: 5
<212> TYPE: PRT
<213> ORGANISM: Mycobacterium tuberculosis

<400> SEQUENCE: 40

Ile Val Leu Gly Arg
1               5

<210> SEQ ID NO 41
<211> LENGTH: 16
<212> TYPE: PRT
<213> ORGANISM: Mycobacterium tuberculosis

<400> SEQUENCE: 41

Thr Gly Val Ile Gly Ser Pro Ala Ala Asn Ala Pro Asp Ala Gly Pro
1               5                   10                  15

<210> SEQ ID NO 42
<211> LENGTH: 35
```

```
<212> TYPE: PRT
<213> ORGANISM: Mycobacterium tuberculosis

<400> SEQUENCE: 42

Val Ala Pro Pro Ala Pro Ala Pro Ala Pro Glu Pro Ala Pro
1               5                   10                  15

Ala Pro Ala Pro Ala Gly Glu Val Ala Pro Thr Pro Thr Pro Thr
                20                  25                  30

Pro Gln Arg
        35

<210> SEQ ID NO 43
<211> LENGTH: 19
<212> TYPE: PRT
<213> ORGANISM: Mycobacterium tuberculosis

<400> SEQUENCE: 43

Thr Thr Gly Asp Pro Pro Phe Pro Gly Gln Pro Pro Val Ala Asn
1               5                   10                  15

Asp Thr Arg

<210> SEQ ID NO 44
<211> LENGTH: 13
<212> TYPE: PRT
<213> ORGANISM: Mycobacterium tuberculosis

<400> SEQUENCE: 44

Ala Ser Ala Glu Ala Thr Asp Ser Lys Ala Ala Ala Arg
1               5                   10

<210> SEQ ID NO 45
<211> LENGTH: 9
<212> TYPE: PRT
<213> ORGANISM: Mycobacterium tuberculosis

<400> SEQUENCE: 45

Ile Val Leu Gly Arg Leu Asp Gln Lys
1               5

<210> SEQ ID NO 46
<211> LENGTH: 8
<212> TYPE: PRT
<213> ORGANISM: Mycobacterium tuberculosis

<400> SEQUENCE: 46

Ile Asp Asn Pro Val Gly Gly Phe
1               5

<210> SEQ ID NO 47
<211> LENGTH: 20
<212> TYPE: PRT
<213> ORGANISM: Mycobacterium tuberculosis

<400> SEQUENCE: 47

Thr Gly Val Ile Gly Ser Pro Ala Ala Asn Ala Pro Asp Ala Gly Pro
1               5                   10                  15

Pro Gln Arg Trp
        20

<210> SEQ ID NO 48
<211> LENGTH: 15
<212> TYPE: PRT
<213> ORGANISM: Mycobacterium tuberculosis
```

```
<400> SEQUENCE: 48

Glu Val Lys Phe Ser Asp Pro Ser Lys Pro Asn Gly Gln Ile Trp
1               5                   10                  15

<210> SEQ ID NO 49
<211> LENGTH: 19
<212> TYPE: PRT
<213> ORGANISM: Mycobacterium tuberculosis

<400> SEQUENCE: 49

Leu Gly Thr Ala Asn Asn Pro Val Asp Lys Gly Ala Ala Lys Ala Leu
1               5                   10                  15

Ala Glu Ser

<210> SEQ ID NO 50
<211> LENGTH: 14
<212> TYPE: PRT
<213> ORGANISM: Mycobacterium tuberculosis

<400> SEQUENCE: 50

Ile Arg Pro Leu Val Glu Ser Asp Ala Ala His Phe Asp Tyr
1               5                   10

<210> SEQ ID NO 51
<211> LENGTH: 8
<212> TYPE: PRT
<213> ORGANISM: Mycobacterium tuberculosis

<400> SEQUENCE: 51

Ser Phe Ala Leu Pro Ala Gly Trp
1               5

<210> SEQ ID NO 52
<211> LENGTH: 23
<212> TYPE: PRT
<213> ORGANISM: Mycobacterium tuberculosis

<400> SEQUENCE: 52

Ala Leu Pro Ala Gly Trp Val Glu Ser Asp Ala Ala His Phe Asp Tyr
1               5                   10                  15

Gly Ser Ala Leu Leu Ala Lys
            20

<210> SEQ ID NO 53
<211> LENGTH: 7
<212> TYPE: PRT
<213> ORGANISM: Mycobacterium tuberculosis

<400> SEQUENCE: 53

Glu Thr Val Ser Leu Asp Ala
1               5

<210> SEQ ID NO 54
<211> LENGTH: 7
<212> TYPE: PRT
<213> ORGANISM: Mycobacterium tuberculosis

<400> SEQUENCE: 54

Ala Ser Pro Pro Ser Thr Ala
1               5

<210> SEQ ID NO 55
```

```
<211> LENGTH: 11
<212> TYPE: PRT
<213> ORGANISM: Mycobacterium tuberculosis

<400> SEQUENCE: 55

Thr Pro Val Ala Pro Pro Pro Ala Ala Ala
1               5                   10

<210> SEQ ID NO 56
<211> LENGTH: 12
<212> TYPE: PRT
<213> ORGANISM: Mycobacterium tuberculosis
<220> FEATURE:
<221> NAME/KEY: MISC_FEATURE
<222> LOCATION: (9)..(9)
<223> OTHER INFORMATION: Xaa can be Asp or Gly

<400> SEQUENCE: 56

Ala Pro Pro Ser Cys Ala Gly Leu Xaa Cys Thr Val
1               5                   10

<210> SEQ ID NO 57
<211> LENGTH: 7
<212> TYPE: PRT
<213> ORGANISM: Mycobacterium tuberculosis
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 57

Xaa Xaa Ala Val Xaa Val Thr
1               5

<210> SEQ ID NO 58
<211> LENGTH: 16
<212> TYPE: PRT
<213> ORGANISM: Mycobacterium tuberculosis

<400> SEQUENCE: 58

Phe Ser Arg Pro Gly Leu Pro Val Glu Tyr Leu Gln Val Pro Ser Pro
1               5                   10                  15

<210> SEQ ID NO 59
<211> LENGTH: 21
<212> TYPE: PRT
<213> ORGANISM: Mycobacterium tuberculosis

<400> SEQUENCE: 59

Thr Glu Lys Thr Pro Asp Asp Val Phe Lys Leu Ala Asp Asp Glu Lys
1               5                   10                  15

Val Glu Tyr Val Asp
            20

<210> SEQ ID NO 60
<211> LENGTH: 15
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
```

```
<222> LOCATION: (4)..(4)
<223> OTHER INFORMATION: Xaa can be Met or Leu
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid

<400> SEQUENCE: 60

Xaa Pro Val Xaa Val Xaa Pro Gly Xaa Glu Xaa Xaa Gln Asp Asn
1               5                   10                  15

<210> SEQ ID NO 61
<211> LENGTH: 12
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be any amino acid

<400> SEQUENCE: 61

Xaa Val Tyr Asp Val Ile Met Leu Thr Ala Gly Pro
1               5                   10

<210> SEQ ID NO 62
<211> LENGTH: 9
<212> TYPE: PRT
<213> ORGANISM: Mycobacterium tuberculosis
<220> FEATURE:
<221> NAME/KEY: MISC_FEATURE
<222> LOCATION: (8)..(8)
<223> OTHER INFORMATION: Xaa can be any amino acid

<400> SEQUENCE: 62

Ala Pro Tyr Glu Asn Leu Met Xaa Pro
1               5

<210> SEQ ID NO 63
<211> LENGTH: 10
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be Lys or Asn
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid

<400> SEQUENCE: 63

Xaa Val Ile Arg Ile Xaa Gly Xaa Thr Asp
1               5                   10

<210> SEQ ID NO 64
<211> LENGTH: 15
<212> TYPE: PRT
<213> ORGANISM: Mycobacterium tuberculosis
```

-continued

```
<400> SEQUENCE: 64

Phe Ala Pro Leu Asn Ser Trp Pro Asp Asn Ala Ser Leu Asp Lys
1               5                   10                  15

<210> SEQ ID NO 65
<211> LENGTH: 9
<212> TYPE: PRT
<213> ORGANISM: Mycobacterium tuberculosis

<400> SEQUENCE: 65

Glu Ala Thr Trp Leu Gly Asp Glu Arg
1               5

<210> SEQ ID NO 66
<211> LENGTH: 17
<212> TYPE: PRT
<213> ORGANISM: Mycobacterium tuberculosis

<400> SEQUENCE: 66

Asp Ala Ile Thr Ser Gly Ile Glu Val Val Trp Thr Asn Thr Pro Thr
1               5                   10                  15

Lys

<210> SEQ ID NO 67
<211> LENGTH: 11
<212> TYPE: PRT
<213> ORGANISM: Mycobacterium tuberculosis

<400> SEQUENCE: 67

Ser Pro Ala Gly Ala Trp Gln Tyr Thr Ala Lys
1               5                   10

<210> SEQ ID NO 68
<211> LENGTH: 16
<212> TYPE: PRT
<213> ORGANISM: Mycobacterium tuberculosis

<400> SEQUENCE: 68

Asp Gly Ala Gly Ala Gly Thr Ile Pro Asp Pro Phe Gly Gly Pro Gly
1               5                   10                  15

<210> SEQ ID NO 69
<211> LENGTH: 15
<212> TYPE: PRT
<213> ORGANISM: Mycobacterium tuberculosis

<400> SEQUENCE: 69

Arg Trp Leu Glu His Pro Glu Glu Leu Ala Asp Glu Phe Ala Lys
1               5                   10                  15

<210> SEQ ID NO 70
<211> LENGTH: 18
<212> TYPE: PRT
<213> ORGANISM: Mycobacterium tuberculosis

<400> SEQUENCE: 70

Thr Leu Glu Glu Ile Gln Glu Ser Phe Asn Ser Ala Ala Pro Gly Asn
1               5                   10                  15

Ile Lys

<210> SEQ ID NO 71
<211> LENGTH: 13
<212> TYPE: PRT
```

-continued

<213> ORGANISM: Mycobacterium tuberculosis

<400> SEQUENCE: 71

Ala Gly His Asn Ile Thr Val Pro Phe Thr Pro Gly Arg
1               5                   10

<210> SEQ ID NO 72
<211> LENGTH: 19
<212> TYPE: PRT
<213> ORGANISM: Mycobacterium tuberculosis

<400> SEQUENCE: 72

Thr Asp Ala Ser Gln Glu Gln Thr Asp Val Glu Ser Phe Ala Val Leu
1               5                   10                  15

Glu Pro Lys

<210> SEQ ID NO 73
<211> LENGTH: 13
<212> TYPE: PRT
<213> ORGANISM: Mycobacterium tuberculosis

<400> SEQUENCE: 73

Gly Asn Pro Leu Pro Ala Glu Tyr Met Leu Leu Asp Lys
1               5                   10

<210> SEQ ID NO 74
<211> LENGTH: 19
<212> TYPE: PRT
<213> ORGANISM: Mycobacterium tuberculosis

<400> SEQUENCE: 74

Ala Asn Leu Leu Thr Leu Ser Ala Pro Glu Met Thr Val Leu Val Gly
1               5                   10                  15

Gly Leu Arg

<210> SEQ ID NO 75
<211> LENGTH: 12
<212> TYPE: PRT
<213> ORGANISM: Mycobacterium tuberculosis

<400> SEQUENCE: 75

Val Asp Leu Val Phe Gly Ser Asn Ser Glu Leu Arg
1               5                   10

<210> SEQ ID NO 76
<211> LENGTH: 15
<212> TYPE: PRT
<213> ORGANISM: Mycobacterium tuberculosis

<400> SEQUENCE: 76

Ala Leu Val Glu Val Tyr Gly Ala Asp Asp Ala Gln Pro Lys Phe
1               5                   10                  15

<210> SEQ ID NO 77
<211> LENGTH: 10
<212> TYPE: PRT
<213> ORGANISM: Mycobacterium tuberculosis

<400> SEQUENCE: 77

Thr Glu Gln Gln Trp Asp Phe Ala Gly Ile
1               5                   10

<210> SEQ ID NO 78

-continued

<211> LENGTH: 10
<212> TYPE: PRT
<213> ORGANISM: Mycobacterium tuberculosis

<400> SEQUENCE: 78

Asp Pro Ala Pro Ala Pro Pro Val Pro Thr
1 5 10

<210> SEQ ID NO 79
<211> LENGTH: 5
<212> TYPE: PRT
<213> ORGANISM: Mycobacterium tuberculosis

<400> SEQUENCE: 79

Asp Glu Cys Ile Gln
1 5

<210> SEQ ID NO 80
<211> LENGTH: 5
<212> TYPE: PRT
<213> ORGANISM: Mycobacterium tuberculosis

<400> SEQUENCE: 80

Arg Ile Lys Ile Phe
1 5

<210> SEQ ID NO 81
<211> LENGTH: 13
<212> TYPE: PRT
<213> ORGANISM: Mycobacterium tuberculosis

<400> SEQUENCE: 81

Ala Tyr Pro Ile Thr Gly Lys Leu Gly Ser Glu Leu Thr
1 5 10

<210> SEQ ID NO 82
<211> LENGTH: 10
<212> TYPE: PRT
<213> ORGANISM: Mycobacterium tuberculosis

<400> SEQUENCE: 82

Met Ala Lys Val Asn Ile Lys Pro Leu Glu
1 5 10

<210> SEQ ID NO 83
<211> LENGTH: 10
<212> TYPE: PRT
<213> ORGANISM: Mycobacterium tuberculosis

<400> SEQUENCE: 83

Cys Gly Ser Lys Pro Pro Ser Pro Glu Thr
1 5 10

<210> SEQ ID NO 84
<211> LENGTH: 10
<212> TYPE: PRT
<213> ORGANISM: Mycobacterium tuberculosis

<400> SEQUENCE: 84

Cys Gly Ser Lys Pro Pro Ser Pro Glu Thr
1 5 10

<210> SEQ ID NO 85
<211> LENGTH: 5
<212> TYPE: PRT

<213> ORGANISM: Mycobacterium tuberculosis

<400> SEQUENCE: 85

Arg Asp Ser Glu Lys
1               5

<210> SEQ ID NO 86
<211> LENGTH: 10
<212> TYPE: PRT
<213> ORGANISM: Mycobacterium tuberculosis

<400> SEQUENCE: 86

Met Ala Arg Ala Val Gly Ile Asp Leu Gly
1               5                   10

<210> SEQ ID NO 87
<211> LENGTH: 10
<212> TYPE: PRT
<213> ORGANISM: Mycobacterium tuberculosis

<400> SEQUENCE: 87

Cys Gly Ser Lys Pro Pro Ser Pro Glu Thr
1               5                   10

<210> SEQ ID NO 88
<211> LENGTH: 12
<212> TYPE: PRT
<213> ORGANISM: Mycobacterium tuberculosis
<220> FEATURE:
<221> NAME/KEY: MISC_FEATURE
<222> LOCATION: (9)..(9)
<223> OTHER INFORMATION: Xaa can be Asp or Gly

<400> SEQUENCE: 88

Ala Pro Pro Ser Cys Ala Gly Leu Xaa Cys Thr Val
1               5                   10

<210> SEQ ID NO 89
<211> LENGTH: 9
<212> TYPE: PRT
<213> ORGANISM: Mycobacterium tuberculosis

<400> SEQUENCE: 89

Cys Ser Ser Asn Lys Ser Thr Thr Gly
1               5

<210> SEQ ID NO 90
<211> LENGTH: 10
<212> TYPE: PRT
<213> ORGANISM: Mycobacterium tuberculosis

<400> SEQUENCE: 90

Met Ala Arg Ala Val Gly Ile Asp Leu Gly
1               5                   10

<210> SEQ ID NO 91
<211> LENGTH: 7
<212> TYPE: PRT
<213> ORGANISM: Mycobacterium tuberculosis
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

```
<400> SEQUENCE: 91

Xaa Xaa Ala Val Xaa Val Thr
1               5

<210> SEQ ID NO 92
<211> LENGTH: 10
<212> TYPE: PRT
<213> ORGANISM: Mycobacterium tuberculosis

<400> SEQUENCE: 92

Phe Ser Arg Pro Gly Leu Pro Val Glu Tyr
1               5                   10

<210> SEQ ID NO 93
<211> LENGTH: 10
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be Lys or Asn
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid

<400> SEQUENCE: 93

Xaa Val Ile Arg Ile Xaa Gly Xaa Thr Asp
1               5                   10

<210> SEQ ID NO 94
<211> LENGTH: 11
<212> TYPE: PRT
<213> ORGANISM: Mycobacterium tuberculosis

<400> SEQUENCE: 94

Met Ala Arg Ala Val Gly Ile Asp Leu Gly Thr
1               5                   10

<210> SEQ ID NO 95
<211> LENGTH: 16
<212> TYPE: PRT
<213> ORGANISM: Mycobacterium tuberculosis

<400> SEQUENCE: 95

Phe Ser Arg Pro Gly Leu Pro Val Glu Tyr Leu Gln Val Pro Ser Pro
1               5                   10                  15

<210> SEQ ID NO 96
<211> LENGTH: 21
<212> TYPE: PRT
<213> ORGANISM: Mycobacterium tuberculosis

<400> SEQUENCE: 96

Thr Glu Lys Thr Pro Asp Asp Val Phe Lys Leu Ala Lys Asp Glu Lys
1               5                   10                  15

Val Glu Tyr Val Asp
            20

<210> SEQ ID NO 97
<211> LENGTH: 10
```

```
<212> TYPE: PRT
<213> ORGANISM: Mycobacterium tuberculosis

<400> SEQUENCE: 97

Phe Ser Arg Pro Gly Leu Pro Val Glu Tyr
1               5                   10

<210> SEQ ID NO 98
<211> LENGTH: 15
<212> TYPE: PRT
<213> ORGANISM: Mycobacterium tuberculosis
<220> FEATURE:
<221> NAME/KEY: MISC_FEATURE
<222> LOCATION: (15)..(15)
<223> OTHER INFORMATION: Xaa can be Glu Thr

<400> SEQUENCE: 98

Thr Glu Lys Thr Pro Asp Asp Val Phe Lys Leu Asp Glu Val Xaa
1               5                   10                  15

<210> SEQ ID NO 99
<211> LENGTH: 10
<212> TYPE: PRT
<213> ORGANISM: Mycobacterium tuberculosis

<400> SEQUENCE: 99

Met Pro Glu Gln His Pro Pro Ile Thr Glu
1               5                   10

<210> SEQ ID NO 100
<211> LENGTH: 15
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be Met or Leu
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid

<400> SEQUENCE: 100

Xaa Pro Val Xaa Val Xaa Pro Gly Xaa Glu Xaa Xaa Gln Asp Asn
1               5                   10                  15

<210> SEQ ID NO 101
<211> LENGTH: 10
<212> TYPE: PRT
<213> ORGANISM: Mycobacterium tuberculosis

<400> SEQUENCE: 101

Phe Ser Arg Pro Gly Leu Pro Val Glu Tyr
1               5                   10

<210> SEQ ID NO 102
<211> LENGTH: 10
```

-continued

<212> TYPE: PRT
<213> ORGANISM: Mycobacterium tuberculosis

<400> SEQUENCE: 102

Ala Pro Tyr Glu Asn Leu Met Val Pro Ser
1 5 10

<210> SEQ ID NO 103
<211> LENGTH: 12
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be any amino acid

<400> SEQUENCE: 103

Xaa Val Tyr Asp Val Ile Met Leu Thr Ala Gly Pro
1 5 10

<210> SEQ ID NO 104
<211> LENGTH: 10
<212> TYPE: PRT
<213> ORGANISM: Mycobacterium tuberculosis

<400> SEQUENCE: 104

Met Ala Glu Tyr Thr Leu Pro Asp Leu Asp
1 5 10

<210> SEQ ID NO 105
<211> LENGTH: 15
<212> TYPE: PRT
<213> ORGANISM: Mycobacterium tuberculosis

<400> SEQUENCE: 105

Asp Pro Val Leu Val Phe Pro Gly Met Glu Ile Arg Gln Asp Asn
1 5 10 15

<210> SEQ ID NO 106
<211> LENGTH: 741
<212> TYPE: PRT
<213> ORGANISM: Mycobacterium tuberculosis

<400> SEQUENCE: 106

Met Thr Asp Arg Val Ser Val Gly Asn Leu Arg Ile Ala Arg Val Leu
1 5 10 15

Tyr Asp Phe Val Asn Asn Glu Ala Leu Pro Gly Thr Asp Ile Asp Pro
20 25 30

Asp Ser Phe Trp Ala Gly Val Asp Lys Val Val Ala Asp Leu Thr Pro
35 40 45

Gln Asn Gln Ala Leu Leu Asn Ala Arg Asp Glu Leu Gln Ala Gln Ile
50 55 60

Asp Lys Trp His Arg Arg Arg Val Ile Glu Pro Ile Asp Met Asp Ala
65 70 75 80

Tyr Arg Gln Phe Leu Thr Glu Ile Gly Tyr Leu Leu Pro Glu Pro Asp
85 90 95

Asp Phe Thr Ile Thr Thr Ser Gly Val Asp Ala Glu Ile Thr Thr Thr
100 105 110

Ala Gly Pro Gln Leu Val Val Pro Val Leu Asn Ala Arg Phe Ala Leu
115 120 125

Asn Ala Ala Asn Ala Arg Trp Gly Ser Leu Tyr Asp Ala Leu Tyr Gly
130 135 140

```
Thr Asp Val Ile Pro Glu Thr Asp Gly Ala Glu Lys Gly Pro Thr Tyr
145                 150                 155                 160

Asn Lys Val Arg Gly Asp Lys Val Ile Ala Tyr Ala Arg Lys Phe Leu
                165                 170                 175

Asp Asp Ser Val Pro Leu Ser Ser Gly Ser Phe Gly Asp Ala Thr Gly
            180                 185                 190

Phe Thr Val Gln Asp Gly Gln Leu Val Val Ala Leu Pro Asp Lys Ser
        195                 200                 205

Thr Gly Leu Ala Asn Pro Gly Gln Phe Ala Gly Tyr Thr Gly Ala Ala
    210                 215                 220

Glu Ser Pro Thr Ser Val Leu Leu Ile Asn His Gly Leu His Ile Glu
225                 230                 235                 240

Ile Leu Ile Asp Pro Glu Ser Gln Val Gly Thr Thr Asp Arg Ala Gly
                245                 250                 255

Val Lys Asp Val Ile Leu Glu Ser Ala Ile Thr Thr Ile Met Asp Phe
            260                 265                 270

Glu Asp Ser Val Ala Ala Val Asp Ala Ala Asp Lys Val Leu Gly Tyr
        275                 280                 285

Arg Asn Trp Leu Gly Leu Asn Lys Gly Asp Leu Ala Ala Ala Val Asp
    290                 295                 300

Lys Asp Gly Thr Ala Phe Leu Arg Val Leu Asn Arg Asp Arg Asn Tyr
305                 310                 315                 320

Thr Ala Pro Gly Gly Gly Gln Phe Thr Leu Pro Gly Arg Ser Leu Met
                325                 330                 335

Phe Val Arg Asn Val Gly His Leu Met Thr Asn Asp Ala Ile Val Asp
            340                 345                 350

Thr Asp Gly Ser Glu Val Phe Glu Gly Ile Met Asp Ala Leu Phe Thr
        355                 360                 365

Gly Leu Ile Ala Ile His Gly Leu Lys Ala Ser Asp Val Asn Gly Pro
    370                 375                 380

Leu Ile Asn Ser Arg Thr Gly Ser Ile Tyr Ile Val Lys Pro Lys Met
385                 390                 395                 400

His Gly Pro Ala Glu Val Ala Phe Thr Cys Glu Leu Phe Ser Arg Val
                405                 410                 415

Glu Asp Val Leu Gly Leu Pro Gln Asn Thr Met Lys Ile Gly Ile Met
            420                 425                 430

Asp Glu Glu Arg Arg Thr Thr Val Asn Leu Lys Ala Cys Ile Lys Ala
        435                 440                 445

Ala Ala Asp Arg Val Val Phe Ile Asn Thr Gly Phe Leu Asp Arg Thr
    450                 455                 460

Gly Asp Glu Ile His Thr Ser Met Glu Ala Gly Pro Met Val Arg Lys
465                 470                 475                 480

Gly Thr Met Lys Ser Gln Pro Trp Ile Leu Ala Tyr Glu Asp His Asn
                485                 490                 495

Val Asp Ala Gly Leu Ala Ala Gly Phe Ser Gly Arg Ala Gln Val Gly
            500                 505                 510

Lys Gly Met Trp Thr Met Thr Glu Leu Met Ala Asp Met Val Glu Thr
        515                 520                 525

Lys Ile Ala Gln Pro Arg Ala Gly Ala Ser Thr Ala Trp Val Pro Ser
    530                 535                 540

Pro Thr Ala Ala Thr Leu His Ala Leu His Tyr His Gln Val Asp Val
545                 550                 555                 560
```

-continued

```
Ala Ala Val Gln Gln Gly Leu Ala Gly Lys Arg Arg Ala Thr Ile Glu
            565                 570                 575

Gln Leu Leu Thr Ile Pro Leu Ala Lys Glu Leu Ala Trp Ala Pro Asp
        580                 585                 590

Glu Ile Arg Glu Val Asp Asn Asn Cys Gln Ser Ile Leu Gly Tyr
    595                 600                 605

Val Val Arg Trp Val Asp Gln Gly Val Gly Cys Ser Lys Val Pro Asp
    610                 615                 620

Ile His Asp Val Ala Leu Met Glu Asp Arg Ala Thr Leu Arg Ile Ser
625                 630                 635                 640

Ser Gln Leu Leu Ala Asn Trp Leu Arg His Gly Val Ile Thr Ser Ala
                645                 650                 655

Asp Val Arg Ala Ser Leu Glu Arg Met Ala Pro Leu Val Asp Arg Gln
            660                 665                 670

Asn Ala Gly Asp Val Ala Tyr Arg Pro Met Ala Pro Asn Phe Asp Asp
        675                 680                 685

Ser Ile Ala Phe Leu Ala Ala Gln Glu Leu Ile Leu Ser Gly Ala Gln
    690                 695                 700

Gln Pro Asn Gly Tyr Thr Glu Pro Ile Leu His Arg Arg Arg Arg Glu
705                 710                 715                 720

Phe Lys Ala Arg Ala Ala Glu Lys Pro Ala Pro Ser Asp Arg Ala Gly
                725                 730                 735

Asp Asp Ala Ala Arg
            740

<210> SEQ ID NO 107
<211> LENGTH: 256
<212> TYPE: PRT
<213> ORGANISM: Mycobacterium tuberculosis

<400> SEQUENCE: 107

Ala Pro Tyr Glu Asn Leu Met Val Pro Ser Pro Ser Met Gly Arg Asp
1               5                   10                  15

Ile Pro Val Ala Phe Leu Ala Gly Gly Pro His Ala Val Tyr Leu Leu
            20                  25                  30

Asp Ala Phe Asn Ala Gly Pro Asp Val Ser Asn Trp Val Thr Ala Gly
        35                  40                  45

Asn Ala Met Asn Thr Leu Ala Gly Lys Gly Ile Ser Val Val Ala Pro
    50                  55                  60

Ala Gly Gly Ala Tyr Ser Met Tyr Thr Asn Trp Glu Gln Asp Gly Ser
65                  70                  75                  80

Lys Gln Trp Asp Thr Phe Leu Ser Ala Glu Leu Pro Asp Trp Leu Ala
                85                  90                  95

Ala Asn Arg Gly Ala Ala Gln Gly Gly Tyr Gly Ala Met Ala Leu Ala
            100                 105                 110

Ala Phe His Pro Asp Arg Phe Gly Phe Ala Gly Ser Met Ser Gly Phe
        115                 120                 125

Leu Tyr Pro Ser Asn Thr Thr Thr Asn Gly Ala Ile Ala Ala Gly Met
    130                 135                 140

Gln Gln Phe Gly Gly Val Asp Thr Asn Gly Met Trp Gly Ala Pro Gln
145                 150                 155                 160

Leu Gly Arg Trp Lys Trp His Asp Pro Trp Val His Ala Ser Leu Leu
                165                 170                 175

Ala Gln Asn Asn Thr Arg Val Trp Val Trp Ser Pro Thr Asn Pro Gly
            180                 185                 190
```

```
Ala Ser Asp Pro Ala Ala Met Ile Gly Gln Thr Ala Glu Ala Met Gly
        195                 200                 205

Asn Ser Arg Met Phe Tyr Asn Gln Tyr Arg Ser Val Gly Gly His Asn
        210                 215                 220

Gly His Phe Asp Phe Pro Ala Ser Gly Asp Asn Gly Trp Gly Ser Trp
225                 230                 235                 240

Ala Pro Gln Leu Gly Ala Met Ser Gly Asp Ile Val Gly Ala Ile Arg
                245                 250                 255

<210> SEQ ID NO 108
<211> LENGTH: 19
<212> TYPE: PRT
<213> ORGANISM: Mycobacterium tuberculosis

<400> SEQUENCE: 108

Cys Gly Thr Asp Gly Ala Glu Lys Gly Pro Thr Tyr Asn Lys Val Arg
1               5                   10                  15

Gly Asp Lys

<210> SEQ ID NO 109
<211> LENGTH: 18
<212> TYPE: PRT
<213> ORGANISM: Mycobacterium tuberculosis

<400> SEQUENCE: 109

Lys Ile Gly Ile Met Asp Glu Glu Arg Arg Thr Thr Val Asn Leu Lys
1               5                   10                  15

Ala Cys

<210> SEQ ID NO 110
<211> LENGTH: 17
<212> TYPE: PRT
<213> ORGANISM: Mycobacterium tuberculosis

<400> SEQUENCE: 110

Glu Leu Ala Trp Ala Pro Asp Glu Ile Arg Glu Glu Val Asp Asn Asn
1               5                   10                  15

Cys

<210> SEQ ID NO 111
<211> LENGTH: 23
<212> TYPE: PRT
<213> ORGANISM: Mycobacterium tuberculosis

<400> SEQUENCE: 111

Leu His Arg Arg Arg Arg Glu Phe Lys Ala Arg Ala Ala Glu Lys Pro
1               5                   10                  15

Ala Pro Ser Asp Arg Ala Gly
            20

<210> SEQ ID NO 112
<211> LENGTH: 16
<212> TYPE: PRT
<213> ORGANISM: Mycobacterium tuberculosis

<400> SEQUENCE: 112

Ala Arg Asp Glu Leu Gln Ala Gln Ile Asp Lys Trp His Arg Arg Arg
1               5                   10                  15

<210> SEQ ID NO 113
```

```
<211> LENGTH: 14
<212> TYPE: PRT
<213> ORGANISM: Mycobacterium tuberculosis

<400> SEQUENCE: 113

Leu Asn Arg Asp Arg Asn Tyr Thr Ala Pro Gly Gly Gly Gln
1               5                   10

<210> SEQ ID NO 114
<211> LENGTH: 15
<212> TYPE: PRT
<213> ORGANISM: Mycobacterium tuberculosis

<400> SEQUENCE: 114

Gly Ala Pro Gln Leu Gly Arg Trp Lys Trp His Asp Pro Trp Val
1               5                   10                  15

<210> SEQ ID NO 115
<211> LENGTH: 6
<212> TYPE: PRT
<213> ORGANISM: Artificial Sequence
<220> FEATURE:
<223> OTHER INFORMATION: Linker peptide

<400> SEQUENCE: 115

Val Pro Arg Gly Ser Asp
1               5

<210> SEQ ID NO 116
<211> LENGTH: 13
<212> TYPE: PRT
<213> ORGANISM: Mycobacterium tuberculosis

<400> SEQUENCE: 116

Met Thr Asp Arg Val Ser Val Gly Asn Leu Arg Ile Ala
1               5                   10

<210> SEQ ID NO 117
<211> LENGTH: 13
<212> TYPE: PRT
<213> ORGANISM: Mycobacterium tuberculosis

<400> SEQUENCE: 117

Val Gly Asn Leu Arg Ile Ala Arg Val Leu Tyr Asp Phe
1               5                   10

<210> SEQ ID NO 118
<211> LENGTH: 13
<212> TYPE: PRT
<213> ORGANISM: Mycobacterium tuberculosis

<400> SEQUENCE: 118

Ala Arg Val Leu Tyr Asp Phe Val Asn Asn Glu Ala Leu
1               5                   10

<210> SEQ ID NO 119
<211> LENGTH: 13
<212> TYPE: PRT
<213> ORGANISM: Mycobacterium tuberculosis

<400> SEQUENCE: 119

Phe Val Asn Asn Glu Ala Leu Pro Gly Thr Asp Ile Asp
1               5                   10

<210> SEQ ID NO 120
```

```
<211> LENGTH: 13
<212> TYPE: PRT
<213> ORGANISM: Mycobacterium tuberculosis

<400> SEQUENCE: 120

Leu Pro Gly Thr Asp Ile Asp Pro Asp Ser Phe Trp Ala
1               5                   10

<210> SEQ ID NO 121
<211> LENGTH: 13
<212> TYPE: PRT
<213> ORGANISM: Mycobacterium tuberculosis

<400> SEQUENCE: 121

Asp Pro Asp Ser Phe Trp Ala Gly Val Asp Lys Val Val
1               5                   10

<210> SEQ ID NO 122
<211> LENGTH: 13
<212> TYPE: PRT
<213> ORGANISM: Mycobacterium tuberculosis

<400> SEQUENCE: 122

Ala Gly Val Asp Lys Val Val Ala Asp Leu Thr Pro Gln
1               5                   10

<210> SEQ ID NO 123
<211> LENGTH: 13
<212> TYPE: PRT
<213> ORGANISM: Mycobacterium tuberculosis

<400> SEQUENCE: 123

Val Ala Asp Leu Thr Pro Gln Asn Gln Ala Leu Leu Asn
1               5                   10

<210> SEQ ID NO 124
<211> LENGTH: 13
<212> TYPE: PRT
<213> ORGANISM: Mycobacterium tuberculosis

<400> SEQUENCE: 124

Gln Asn Gln Ala Leu Leu Asn Ala Arg Asp Glu Leu Gln
1               5                   10

<210> SEQ ID NO 125
<211> LENGTH: 13
<212> TYPE: PRT
<213> ORGANISM: Mycobacterium tuberculosis

<400> SEQUENCE: 125

Asn Ala Arg Asp Glu Leu Gln Ala Gln Ile Asp Lys Trp
1               5                   10

<210> SEQ ID NO 126
<211> LENGTH: 13
<212> TYPE: PRT
<213> ORGANISM: Mycobacterium tuberculosis

<400> SEQUENCE: 126

Gln Ala Gln Ile Asp Lys Trp His Arg Arg Val Ile
1               5                   10

<210> SEQ ID NO 127
<211> LENGTH: 13
<212> TYPE: PRT
```

-continued

<213> ORGANISM: Mycobacterium tuberculosis

<400> SEQUENCE: 127

Trp His Arg Arg Arg Val Ile Glu Pro Ile Asp Met Asp
1               5                   10

<210> SEQ ID NO 128
<211> LENGTH: 13
<212> TYPE: PRT
<213> ORGANISM: Mycobacterium tuberculosis

<400> SEQUENCE: 128

Ile Glu Pro Ile Asp Met Asp Ala Tyr Arg Gln Phe Leu
1               5                   10

<210> SEQ ID NO 129
<211> LENGTH: 13
<212> TYPE: PRT
<213> ORGANISM: Mycobacterium tuberculosis

<400> SEQUENCE: 129

Asp Ala Tyr Arg Gln Phe Leu Thr Glu Ile Gly Tyr Leu
1               5                   10

<210> SEQ ID NO 130
<211> LENGTH: 13
<212> TYPE: PRT
<213> ORGANISM: Mycobacterium tuberculosis

<400> SEQUENCE: 130

Leu Thr Glu Ile Gly Tyr Leu Leu Pro Glu Pro Asp Asp
1               5                   10

<210> SEQ ID NO 131
<211> LENGTH: 13
<212> TYPE: PRT
<213> ORGANISM: Mycobacterium tuberculosis

<400> SEQUENCE: 131

Leu Leu Pro Glu Pro Asp Asp Phe Thr Ile Thr Thr Ser
1               5                   10

<210> SEQ ID NO 132
<211> LENGTH: 13
<212> TYPE: PRT
<213> ORGANISM: Mycobacterium tuberculosis

<400> SEQUENCE: 132

Asp Phe Thr Ile Thr Thr Ser Gly Val Asp Ala Glu Ile
1               5                   10

<210> SEQ ID NO 133
<211> LENGTH: 13
<212> TYPE: PRT
<213> ORGANISM: Mycobacterium tuberculosis

<400> SEQUENCE: 133

Ser Gly Val Asp Ala Glu Ile Thr Thr Thr Ala Gly Pro
1               5                   10

<210> SEQ ID NO 134
<211> LENGTH: 13
<212> TYPE: PRT
<213> ORGANISM: Mycobacterium tuberculosis -continued

<400> SEQUENCE: 134

Ile Thr Thr Thr Ala Gly Pro Gln Leu Val Val Pro Val
1               5                   10

<210> SEQ ID NO 135
<211> LENGTH: 13
<212> TYPE: PRT
<213> ORGANISM: Mycobacterium tuberculosis

<400> SEQUENCE: 135

Pro Gln Leu Val Val Pro Val Leu Asn Ala Arg Phe Ala
1               5                   10

<210> SEQ ID NO 136
<211> LENGTH: 13
<212> TYPE: PRT
<213> ORGANISM: Mycobacterium tuberculosis

<400> SEQUENCE: 136

Val Leu Asn Ala Arg Phe Ala Leu Asn Ala Ala Asn Ala
1               5                   10

<210> SEQ ID NO 137
<211> LENGTH: 13
<212> TYPE: PRT
<213> ORGANISM: Mycobacterium tuberculosis

<400> SEQUENCE: 137

Ala Leu Asn Ala Ala Asn Ala Arg Trp Gly Ser Leu Tyr
1               5                   10

<210> SEQ ID NO 138
<211> LENGTH: 13
<212> TYPE: PRT
<213> ORGANISM: Mycobacterium tuberculosis

<400> SEQUENCE: 138

Ala Arg Trp Gly Ser Leu Tyr Asp Ala Leu Tyr Gly Thr
1               5                   10

<210> SEQ ID NO 139
<211> LENGTH: 13
<212> TYPE: PRT
<213> ORGANISM: Mycobacterium tuberculosis

<400> SEQUENCE: 139

Tyr Asp Ala Leu Tyr Gly Thr Asp Val Ile Pro Glu Thr
1               5                   10

<210> SEQ ID NO 140
<211> LENGTH: 13
<212> TYPE: PRT
<213> ORGANISM: Mycobacterium tuberculosis

<400> SEQUENCE: 140

Thr Asp Val Ile Pro Glu Thr Asp Gly Ala Glu Lys Gly
1               5                   10

<210> SEQ ID NO 141
<211> LENGTH: 13
<212> TYPE: PRT
<213> ORGANISM: Mycobacterium tuberculosis

<400> SEQUENCE: 141

```
Thr Asp Gly Ala Glu Lys Gly Pro Thr Tyr Asn Lys Val
1               5                   10
```

<210> SEQ ID NO 142
<211> LENGTH: 13
<212> TYPE: PRT
<213> ORGANISM: Mycobacterium tuberculosis

<400> SEQUENCE: 142

```
Gly Pro Thr Tyr Asn Lys Val Arg Gly Asp Lys Val Ile
1               5                   10
```

<210> SEQ ID NO 143
<211> LENGTH: 13
<212> TYPE: PRT
<213> ORGANISM: Mycobacterium tuberculosis

<400> SEQUENCE: 143

```
Val Arg Gly Asp Lys Val Ile Ala Tyr Ala Arg Lys Phe
1               5                   10
```

<210> SEQ ID NO 144
<211> LENGTH: 13
<212> TYPE: PRT
<213> ORGANISM: Mycobacterium tuberculosis

<400> SEQUENCE: 144

```
Ile Ala Tyr Ala Arg Lys Phe Leu Asp Asp Ser Val Pro
1               5                   10
```

<210> SEQ ID NO 145
<211> LENGTH: 13
<212> TYPE: PRT
<213> ORGANISM: Mycobacterium tuberculosis

<400> SEQUENCE: 145

```
Phe Leu Asp Asp Ser Val Pro Leu Ser Ser Gly Ser Phe
1               5                   10
```

<210> SEQ ID NO 146
<211> LENGTH: 13
<212> TYPE: PRT
<213> ORGANISM: Mycobacterium tuberculosis

<400> SEQUENCE: 146

```
Pro Leu Ser Ser Gly Ser Phe Gly Asp Ala Thr Gly Phe
1               5                   10
```

<210> SEQ ID NO 147
<211> LENGTH: 13
<212> TYPE: PRT
<213> ORGANISM: Mycobacterium tuberculosis

<400> SEQUENCE: 147

```
Phe Gly Asp Ala Thr Gly Phe Thr Val Gln Asp Gly Gln
1               5                   10
```

<210> SEQ ID NO 148
<211> LENGTH: 11
<212> TYPE: PRT
<213> ORGANISM: Mycobacterium tuberculosis

<400> SEQUENCE: 148

```
Phe Thr Val Gln Asp Gly Gln Leu Val Val Pro
1               5                   10
```

-continued

<210> SEQ ID NO 149
<211> LENGTH: 11
<212> TYPE: PRT
<213> ORGANISM: Mycobacterium tuberculosis

<400> SEQUENCE: 149

Gln Leu Val Val Pro Asp Lys Ser Thr Gly Leu
1               5                   10

<210> SEQ ID NO 150
<211> LENGTH: 13
<212> TYPE: PRT
<213> ORGANISM: Mycobacterium tuberculosis

<400> SEQUENCE: 150

Pro Asp Lys Ser Thr Gly Leu Ala Asn Pro Gly Gln Phe
1               5                   10

<210> SEQ ID NO 151
<211> LENGTH: 13
<212> TYPE: PRT
<213> ORGANISM: Mycobacterium tuberculosis

<400> SEQUENCE: 151

Leu Ala Asn Pro Gly Gln Phe Ala Gly Tyr Thr Gly Ala
1               5                   10

<210> SEQ ID NO 152
<211> LENGTH: 13
<212> TYPE: PRT
<213> ORGANISM: Mycobacterium tuberculosis

<400> SEQUENCE: 152

Phe Ala Gly Tyr Thr Gly Ala Ala Glu Ser Pro Thr Ser
1               5                   10

<210> SEQ ID NO 153
<211> LENGTH: 13
<212> TYPE: PRT
<213> ORGANISM: Mycobacterium tuberculosis

<400> SEQUENCE: 153

Ala Ala Glu Ser Pro Thr Ser Val Leu Leu Ile Asn His
1               5                   10

<210> SEQ ID NO 154
<211> LENGTH: 13
<212> TYPE: PRT
<213> ORGANISM: Mycobacterium tuberculosis

<400> SEQUENCE: 154

Ser Val Leu Leu Ile Asn His Gly Leu His Ile Glu Ile
1               5                   10

<210> SEQ ID NO 155
<211> LENGTH: 13
<212> TYPE: PRT
<213> ORGANISM: Mycobacterium tuberculosis

<400> SEQUENCE: 155

His Gly Leu His Ile Glu Ile Leu Ile Asp Pro Glu Ser
1               5                   10

-continued

<210> SEQ ID NO 156
<211> LENGTH: 13
<212> TYPE: PRT
<213> ORGANISM: Mycobacterium tuberculosis

<400> SEQUENCE: 156

Ile Leu Ile Asp Pro Glu Ser Gln Val Gly Thr Thr Asp
1               5                   10

<210> SEQ ID NO 157
<211> LENGTH: 13
<212> TYPE: PRT
<213> ORGANISM: Mycobacterium tuberculosis

<400> SEQUENCE: 157

Ser Gln Val Gly Thr Thr Asp Arg Ala Gly Val Lys Asp
1               5                   10

<210> SEQ ID NO 158
<211> LENGTH: 11
<212> TYPE: PRT
<213> ORGANISM: Mycobacterium tuberculosis

<400> SEQUENCE: 158

Asp Arg Ala Gly Val Lys Asp Val Ile Ser Ala
1               5                   10

<210> SEQ ID NO 159
<211> LENGTH: 11
<212> TYPE: PRT
<213> ORGANISM: Mycobacterium tuberculosis

<400> SEQUENCE: 159

Asp Val Ile Ser Ala Ile Thr Thr Ile Met Asp
1               5                   10

<210> SEQ ID NO 160
<211> LENGTH: 13
<212> TYPE: PRT
<213> ORGANISM: Mycobacterium tuberculosis

<400> SEQUENCE: 160

Ala Ile Thr Thr Ile Met Asp Phe Glu Asp Ser Val Ala
1               5                   10

<210> SEQ ID NO 161
<211> LENGTH: 13
<212> TYPE: PRT
<213> ORGANISM: Mycobacterium tuberculosis

<400> SEQUENCE: 161

Asp Phe Glu Asp Ser Val Ala Ala Val Asp Ala Ala Asp
1               5                   10

<210> SEQ ID NO 162
<211> LENGTH: 13
<212> TYPE: PRT
<213> ORGANISM: Mycobacterium tuberculosis

<400> SEQUENCE: 162

Ala Ala Val Asp Ala Ala Asp Lys Val Leu Gly Tyr Arg
1               5                   10

<210> SEQ ID NO 163
<211> LENGTH: 11

-continued

<212> TYPE: PRT
<213> ORGANISM: Mycobacterium tuberculosis

<400> SEQUENCE: 163

Asp Lys Val Leu Gly Tyr Arg Asn Trp Leu Gln
1 5 10

<210> SEQ ID NO 164
<211> LENGTH: 11
<212> TYPE: PRT
<213> ORGANISM: Mycobacterium tuberculosis

<400> SEQUENCE: 164

Arg Asn Trp Leu Gln Lys Gly Asp Leu Ala Ala
1 5 10

<210> SEQ ID NO 165
<211> LENGTH: 13
<212> TYPE: PRT
<213> ORGANISM: Mycobacterium tuberculosis

<400> SEQUENCE: 165

Asn Lys Gly Asp Leu Ala Ala Ala Val Asp Lys Asp Gly
1 5 10

<210> SEQ ID NO 166
<211> LENGTH: 13
<212> TYPE: PRT
<213> ORGANISM: Mycobacterium tuberculosis

<400> SEQUENCE: 166

Ala Ala Val Asp Lys Asp Gly Thr Ala Phe Leu Arg Val
1 5 10

<210> SEQ ID NO 167
<211> LENGTH: 13
<212> TYPE: PRT
<213> ORGANISM: Mycobacterium tuberculosis

<400> SEQUENCE: 167

Gly Thr Ala Phe Leu Arg Val Leu Asn Arg Asp Arg Asn
1 5 10

<210> SEQ ID NO 168
<211> LENGTH: 13
<212> TYPE: PRT
<213> ORGANISM: Mycobacterium tuberculosis

<400> SEQUENCE: 168

Val Leu Asn Arg Asp Arg Asn Tyr Thr Ala Pro Gly Gly
1 5 10

<210> SEQ ID NO 169
<211> LENGTH: 13
<212> TYPE: PRT
<213> ORGANISM: Mycobacterium tuberculosis

<400> SEQUENCE: 169

Asn Tyr Thr Ala Pro Gly Gly Gly Gln Phe Thr Leu Pro
1 5 10

<210> SEQ ID NO 170
<211> LENGTH: 13
<212> TYPE: PRT
<213> ORGANISM: Mycobacterium tuberculosis

```
<400> SEQUENCE: 170

Gly Gly Gln Phe Thr Leu Pro Gly Arg Ser Leu Met Phe
1               5                   10

<210> SEQ ID NO 171
<211> LENGTH: 13
<212> TYPE: PRT
<213> ORGANISM: Mycobacterium tuberculosis

<400> SEQUENCE: 171

Pro Gly Arg Ser Leu Met Phe Val Arg Asn Val Gly His
1               5                   10

<210> SEQ ID NO 172
<211> LENGTH: 13
<212> TYPE: PRT
<213> ORGANISM: Mycobacterium tuberculosis

<400> SEQUENCE: 172

Phe Val Arg Asn Val Gly His Leu Met Thr Asn Asp Ala
1               5                   10

<210> SEQ ID NO 173
<211> LENGTH: 13
<212> TYPE: PRT
<213> ORGANISM: Mycobacterium tuberculosis

<400> SEQUENCE: 173

His Leu Met Thr Asn Asp Ala Ile Val Asp Thr Asp Gly
1               5                   10

<210> SEQ ID NO 174
<211> LENGTH: 13
<212> TYPE: PRT
<213> ORGANISM: Mycobacterium tuberculosis

<400> SEQUENCE: 174

Ala Ile Val Asp Thr Asp Gly Ser Glu Val Phe Glu Gly
1               5                   10

<210> SEQ ID NO 175
<211> LENGTH: 13
<212> TYPE: PRT
<213> ORGANISM: Mycobacterium tuberculosis

<400> SEQUENCE: 175

Gly Ser Glu Val Phe Glu Gly Ile Met Asp Ala Leu Phe
1               5                   10

<210> SEQ ID NO 176
<211> LENGTH: 13
<212> TYPE: PRT
<213> ORGANISM: Mycobacterium tuberculosis

<400> SEQUENCE: 176

Gly Ile Met Asp Ala Leu Phe Thr Gly Leu Ile Ala Ile
1               5                   10

<210> SEQ ID NO 177
<211> LENGTH: 13
<212> TYPE: PRT
<213> ORGANISM: Mycobacterium tuberculosis

<400> SEQUENCE: 177
```

```
Phe Thr Gly Leu Ile Ala Ile His Gly Leu Lys Ala Ser
1               5                   10
```

<210> SEQ ID NO 178
<211> LENGTH: 13
<212> TYPE: PRT
<213> ORGANISM: Mycobacterium tuberculosis

<400> SEQUENCE: 178

```
Ile His Gly Leu Lys Ala Ser Asp Val Asn Gly Pro Leu
1               5                   10
```

<210> SEQ ID NO 179
<211> LENGTH: 13
<212> TYPE: PRT
<213> ORGANISM: Mycobacterium tuberculosis

<400> SEQUENCE: 179

```
Ser Asp Val Asn Gly Pro Leu Ile Asn Ser Arg Thr Gly
1               5                   10
```

<210> SEQ ID NO 180
<211> LENGTH: 13
<212> TYPE: PRT
<213> ORGANISM: Mycobacterium tuberculosis

<400> SEQUENCE: 180

```
Leu Ile Asn Ser Arg Thr Gly Ser Ile Tyr Ile Val Lys
1               5                   10
```

<210> SEQ ID NO 181
<211> LENGTH: 13
<212> TYPE: PRT
<213> ORGANISM: Mycobacterium tuberculosis

<400> SEQUENCE: 181

```
Gly Ser Ile Tyr Ile Val Lys Pro Lys Met His Gly Pro
1               5                   10
```

<210> SEQ ID NO 182
<211> LENGTH: 13
<212> TYPE: PRT
<213> ORGANISM: Mycobacterium tuberculosis

<400> SEQUENCE: 182

```
Lys Pro Lys Met His Gly Pro Ala Glu Val Ala Phe Thr
1               5                   10
```

<210> SEQ ID NO 183
<211> LENGTH: 13
<212> TYPE: PRT
<213> ORGANISM: Mycobacterium tuberculosis

<400> SEQUENCE: 183

```
Pro Ala Glu Val Ala Phe Thr Cys Glu Leu Phe Ser Arg
1               5                   10
```

<210> SEQ ID NO 184
<211> LENGTH: 13
<212> TYPE: PRT
<213> ORGANISM: Mycobacterium tuberculosis

<400> SEQUENCE: 184

```
Thr Cys Glu Leu Phe Ser Arg Val Glu Asp Val Leu Gly
```

```
                1               5                   10
```

<210> SEQ ID NO 185
<211> LENGTH: 13
<212> TYPE: PRT
<213> ORGANISM: Mycobacterium tuberculosis

<400> SEQUENCE: 185

```
Arg Val Glu Asp Val Leu Gly Leu Pro Gln Asn Thr Met
1               5                   10
```

<210> SEQ ID NO 186
<211> LENGTH: 13
<212> TYPE: PRT
<213> ORGANISM: Mycobacterium tuberculosis

<400> SEQUENCE: 186

```
Gly Leu Pro Gln Asn Thr Met Lys Ile Gly Ile Met Asp
1               5                   10
```

<210> SEQ ID NO 187
<211> LENGTH: 13
<212> TYPE: PRT
<213> ORGANISM: Mycobacterium tuberculosis

<400> SEQUENCE: 187

```
Met Lys Ile Gly Ile Met Asp Glu Glu Arg Arg Thr Thr
1               5                   10
```

<210> SEQ ID NO 188
<211> LENGTH: 13
<212> TYPE: PRT
<213> ORGANISM: Mycobacterium tuberculosis

<400> SEQUENCE: 188

```
Asp Glu Glu Arg Arg Thr Thr Val Asn Leu Lys Ala Cys
1               5                   10
```

<210> SEQ ID NO 189
<211> LENGTH: 13
<212> TYPE: PRT
<213> ORGANISM: Mycobacterium tuberculosis

<400> SEQUENCE: 189

```
Thr Val Asn Leu Lys Ala Cys Ile Lys Ala Ala Ala Asp
1               5                   10
```

<210> SEQ ID NO 190
<211> LENGTH: 13
<212> TYPE: PRT
<213> ORGANISM: Mycobacterium tuberculosis

<400> SEQUENCE: 190

```
Cys Ile Lys Ala Ala Ala Asp Arg Val Val Phe Ile Asn
1               5                   10
```

<210> SEQ ID NO 191
<211> LENGTH: 13
<212> TYPE: PRT
<213> ORGANISM: Mycobacterium tuberculosis

<400> SEQUENCE: 191

```
Asp Arg Val Val Phe Ile Asn Thr Gly Phe Leu Asp Arg
1               5                   10
```

```
<210> SEQ ID NO 192
<211> LENGTH: 13
<212> TYPE: PRT
<213> ORGANISM: Mycobacterium tuberculosis

<400> SEQUENCE: 192

Asn Thr Gly Phe Leu Asp Arg Thr Gly Asp Glu Ile His
1               5                   10

<210> SEQ ID NO 193
<211> LENGTH: 13
<212> TYPE: PRT
<213> ORGANISM: Mycobacterium tuberculosis

<400> SEQUENCE: 193

Arg Thr Gly Asp Glu Ile His Thr Ser Met Glu Ala Gly
1               5                   10

<210> SEQ ID NO 194
<211> LENGTH: 13
<212> TYPE: PRT
<213> ORGANISM: Mycobacterium tuberculosis

<400> SEQUENCE: 194

His Thr Ser Met Glu Ala Gly Pro Met Val Arg Lys Gly
1               5                   10

<210> SEQ ID NO 195
<211> LENGTH: 13
<212> TYPE: PRT
<213> ORGANISM: Mycobacterium tuberculosis

<400> SEQUENCE: 195

Gly Pro Met Val Arg Lys Gly Thr Met Lys Ser Gln Pro
1               5                   10

<210> SEQ ID NO 196
<211> LENGTH: 13
<212> TYPE: PRT
<213> ORGANISM: Mycobacterium tuberculosis

<400> SEQUENCE: 196

Gly Thr Met Lys Ser Gln Pro Trp Ile Leu Ala Tyr Glu
1               5                   10

<210> SEQ ID NO 197
<211> LENGTH: 13
<212> TYPE: PRT
<213> ORGANISM: Mycobacterium tuberculosis

<400> SEQUENCE: 197

Pro Trp Ile Leu Ala Tyr Glu Asp His Asn Val Asp Ala
1               5                   10

<210> SEQ ID NO 198
<211> LENGTH: 13
<212> TYPE: PRT
<213> ORGANISM: Mycobacterium tuberculosis

<400> SEQUENCE: 198

Glu Asp His Asn Val Asp Ala Gly Leu Ala Ala Gly Phe
1               5                   10

<210> SEQ ID NO 199
```

```
<211> LENGTH: 13
<212> TYPE: PRT
<213> ORGANISM: Mycobacterium tuberculosis

<400> SEQUENCE: 199

Ala Gly Leu Ala Ala Gly Phe Ser Gly Arg Ala Gln Val
1               5                   10

<210> SEQ ID NO 200
<211> LENGTH: 13
<212> TYPE: PRT
<213> ORGANISM: Mycobacterium tuberculosis

<400> SEQUENCE: 200

Phe Ser Gly Arg Ala Gln Val Gly Lys Gly Met Trp Thr
1               5                   10

<210> SEQ ID NO 201
<211> LENGTH: 13
<212> TYPE: PRT
<213> ORGANISM: Mycobacterium tuberculosis

<400> SEQUENCE: 201

Val Gly Lys Gly Met Trp Thr Met Thr Glu Leu Met Ala
1               5                   10

<210> SEQ ID NO 202
<211> LENGTH: 13
<212> TYPE: PRT
<213> ORGANISM: Mycobacterium tuberculosis

<400> SEQUENCE: 202

Thr Met Thr Glu Leu Met Ala Asp Met Val Glu Thr Lys
1               5                   10

<210> SEQ ID NO 203
<211> LENGTH: 13
<212> TYPE: PRT
<213> ORGANISM: Mycobacterium tuberculosis

<400> SEQUENCE: 203

Ala Asp Met Val Glu Thr Lys Ile Ala Gln Pro Arg Ala
1               5                   10

<210> SEQ ID NO 204
<211> LENGTH: 13
<212> TYPE: PRT
<213> ORGANISM: Mycobacterium tuberculosis

<400> SEQUENCE: 204

Lys Ile Ala Gln Pro Arg Ala Gly Ala Ser Thr Ala Trp
1               5                   10

<210> SEQ ID NO 205
<211> LENGTH: 13
<212> TYPE: PRT
<213> ORGANISM: Mycobacterium tuberculosis

<400> SEQUENCE: 205

Ala Gly Ala Ser Thr Ala Trp Val Pro Ser Pro Thr Ala
1               5                   10

<210> SEQ ID NO 206
<211> LENGTH: 13
<212> TYPE: PRT
```

<213> ORGANISM: Mycobacterium tuberculosis

<400> SEQUENCE: 206

Trp Val Ser Pro Thr Ala Ala Thr Leu His Ala Leu
1               5                   10

<210> SEQ ID NO 207
<211> LENGTH: 13
<212> TYPE: PRT
<213> ORGANISM: Mycobacterium tuberculosis

<400> SEQUENCE: 207

Ala Ala Thr Leu His Ala Leu His Tyr His Gln Val Asp
1               5                   10

<210> SEQ ID NO 208
<211> LENGTH: 13
<212> TYPE: PRT
<213> ORGANISM: Mycobacterium tuberculosis

<400> SEQUENCE: 208

Leu His Tyr His Gln Val Asp Val Ala Ala Val Gln Gln
1               5                   10

<210> SEQ ID NO 209
<211> LENGTH: 13
<212> TYPE: PRT
<213> ORGANISM: Mycobacterium tuberculosis

<400> SEQUENCE: 209

Asp Val Ala Ala Val Gln Gln Gly Leu Ala Gly Lys Arg
1               5                   10

<210> SEQ ID NO 210
<211> LENGTH: 13
<212> TYPE: PRT
<213> ORGANISM: Mycobacterium tuberculosis

<400> SEQUENCE: 210

Gln Gly Leu Ala Gly Lys Arg Arg Ala Thr Ile Glu Gln
1               5                   10

<210> SEQ ID NO 211
<211> LENGTH: 13
<212> TYPE: PRT
<213> ORGANISM: Mycobacterium tuberculosis

<400> SEQUENCE: 211

Arg Arg Ala Thr Ile Glu Gln Leu Leu Thr Ile Pro Leu
1               5                   10

<210> SEQ ID NO 212
<211> LENGTH: 13
<212> TYPE: PRT
<213> ORGANISM: Mycobacterium tuberculosis

<400> SEQUENCE: 212

Gln Leu Leu Thr Ile Pro Leu Ala Lys Glu Leu Ala Trp
1               5                   10

<210> SEQ ID NO 213
<211> LENGTH: 13
<212> TYPE: PRT
<213> ORGANISM: Mycobacterium tuberculosis

<400> SEQUENCE: 213

Leu Ala Lys Glu Leu Ala Trp Ala Pro Asp Glu Ile Arg
1               5                   10

<210> SEQ ID NO 214
<211> LENGTH: 13
<212> TYPE: PRT
<213> ORGANISM: Mycobacterium tuberculosis

<400> SEQUENCE: 214

Trp Ala Pro Asp Glu Ile Arg Glu Glu Val Asp Asn Asn
1               5                   10

<210> SEQ ID NO 215
<211> LENGTH: 13
<212> TYPE: PRT
<213> ORGANISM: Mycobacterium tuberculosis

<400> SEQUENCE: 215

Arg Glu Glu Val Asp Asn Asn Cys Gln Ser Ile Leu Gly
1               5                   10

<210> SEQ ID NO 216
<211> LENGTH: 13
<212> TYPE: PRT
<213> ORGANISM: Mycobacterium tuberculosis

<400> SEQUENCE: 216

Asn Cys Gln Ser Ile Leu Gly Tyr Val Val Arg Trp Val
1               5                   10

<210> SEQ ID NO 217
<211> LENGTH: 13
<212> TYPE: PRT
<213> ORGANISM: Mycobacterium tuberculosis

<400> SEQUENCE: 217

Gly Tyr Val Val Arg Trp Val Asp Gln Gly Val Gly Cys
1               5                   10

<210> SEQ ID NO 218
<211> LENGTH: 13
<212> TYPE: PRT
<213> ORGANISM: Mycobacterium tuberculosis

<400> SEQUENCE: 218

Val Asp Gln Gly Val Gly Cys Ser Lys Val Pro Asp Ile
1               5                   10

<210> SEQ ID NO 219
<211> LENGTH: 11
<212> TYPE: PRT
<213> ORGANISM: Mycobacterium tuberculosis

<400> SEQUENCE: 219

Cys Ser Lys Val Pro Asp Ile His Asp Val Met
1               5                   10

<210> SEQ ID NO 220
<211> LENGTH: 11
<212> TYPE: PRT
<213> ORGANISM: Mycobacterium tuberculosis

<400> SEQUENCE: 220

-continued

Ile His Asp Val Met Glu Asp Arg Ala Thr Leu
1               5                   10

<210> SEQ ID NO 221
<211> LENGTH: 13
<212> TYPE: PRT
<213> ORGANISM: Mycobacterium tuberculosis

<400> SEQUENCE: 221

Met Glu Asp Arg Ala Thr Leu Arg Ile Ser Ser Gln Leu
1               5                   10

<210> SEQ ID NO 222
<211> LENGTH: 13
<212> TYPE: PRT
<213> ORGANISM: Mycobacterium tuberculosis

<400> SEQUENCE: 222

Leu Arg Ile Ser Ser Gln Leu Leu Ala Asn Trp Leu Arg
1               5                   10

<210> SEQ ID NO 223
<211> LENGTH: 13
<212> TYPE: PRT
<213> ORGANISM: Mycobacterium tuberculosis

<400> SEQUENCE: 223

Leu Leu Ala Asn Trp Leu Arg His Gly Val Ile Thr Ser
1               5                   10

<210> SEQ ID NO 224
<211> LENGTH: 13
<212> TYPE: PRT
<213> ORGANISM: Mycobacterium tuberculosis

<400> SEQUENCE: 224

Arg His Gly Val Ile Thr Ser Ala Asp Val Arg Ala Ser
1               5                   10

<210> SEQ ID NO 225
<211> LENGTH: 13
<212> TYPE: PRT
<213> ORGANISM: Mycobacterium tuberculosis

<400> SEQUENCE: 225

Ser Ala Asp Val Arg Ala Ser Leu Glu Arg Met Ala Pro
1               5                   10

<210> SEQ ID NO 226
<211> LENGTH: 13
<212> TYPE: PRT
<213> ORGANISM: Mycobacterium tuberculosis

<400> SEQUENCE: 226

Ser Leu Glu Arg Met Ala Pro Leu Val Asp Arg Gln Asn
1               5                   10

<210> SEQ ID NO 227
<211> LENGTH: 13
<212> TYPE: PRT
<213> ORGANISM: Mycobacterium tuberculosis

<400> SEQUENCE: 227

Pro Leu Val Asp Arg Gln Asn Ala Gly Asp Val Ala Tyr
1               5                   10

<210> SEQ ID NO 228
<211> LENGTH: 13
<212> TYPE: PRT
<213> ORGANISM: Mycobacterium tuberculosis

<400> SEQUENCE: 228

Asn Ala Gly Asp Val Ala Tyr Arg Pro Met Ala Pro Asn
1               5                   10

<210> SEQ ID NO 229
<211> LENGTH: 13
<212> TYPE: PRT
<213> ORGANISM: Mycobacterium tuberculosis

<400> SEQUENCE: 229

Tyr Arg Pro Met Ala Pro Asn Phe Asp Asp Ser Ile Ala
1               5                   10

<210> SEQ ID NO 230
<211> LENGTH: 13
<212> TYPE: PRT
<213> ORGANISM: Mycobacterium tuberculosis

<400> SEQUENCE: 230

Asn Phe Asp Asp Ser Ile Ala Phe Leu Ala Ala Gln Glu
1               5                   10

<210> SEQ ID NO 231
<211> LENGTH: 13
<212> TYPE: PRT
<213> ORGANISM: Mycobacterium tuberculosis

<400> SEQUENCE: 231

Ala Phe Leu Ala Ala Gln Glu Leu Ile Leu Ser Gly Ala
1               5                   10

<210> SEQ ID NO 232
<211> LENGTH: 13
<212> TYPE: PRT
<213> ORGANISM: Mycobacterium tuberculosis

<400> SEQUENCE: 232

Glu Leu Ile Leu Ser Gly Ala Gln Gln Pro Asn Gly Tyr
1               5                   10

<210> SEQ ID NO 233
<211> LENGTH: 13
<212> TYPE: PRT
<213> ORGANISM: Mycobacterium tuberculosis

<400> SEQUENCE: 233

Ala Gln Gln Pro Asn Gly Tyr Thr Glu Pro Ile Leu His
1               5                   10

<210> SEQ ID NO 234
<211> LENGTH: 13
<212> TYPE: PRT
<213> ORGANISM: Mycobacterium tuberculosis

<400> SEQUENCE: 234

Tyr Thr Glu Pro Ile Leu His Arg Arg Arg Arg Glu Phe
1               5                   10

-continued

<210> SEQ ID NO 235
<211> LENGTH: 13
<212> TYPE: PRT
<213> ORGANISM: Mycobacterium tuberculosis

<400> SEQUENCE: 235

His Arg Arg Arg Arg Glu Phe Lys Ala Arg Ala Ala Glu
1 5 10

<210> SEQ ID NO 236
<211> LENGTH: 13
<212> TYPE: PRT
<213> ORGANISM: Mycobacterium tuberculosis

<400> SEQUENCE: 236

Phe Lys Ala Arg Ala Ala Glu Lys Pro Ala Pro Ser Asp
1 5 10

<210> SEQ ID NO 237
<211> LENGTH: 13
<212> TYPE: PRT
<213> ORGANISM: Mycobacterium tuberculosis

<400> SEQUENCE: 237

Glu Lys Pro Ala Pro Ser Asp Arg Ala Gly Asp Asp Ala
1 5 10

<210> SEQ ID NO 238
<211> LENGTH: 6
<212> TYPE: PRT
<213> ORGANISM: Artificial Sequence
<220> FEATURE:
<223> OTHER INFORMATION: Linker peptide

<400> SEQUENCE: 238

Asp Asp Lys Asp Trp His
1 5

EARLY DETECTION OF MYCOBACTERIAL DISEASE USING PEPTIDES

This application claims priority from U.S. Provisional Appln 60/309,185 filed Aug. 2, 2001, and is a Continuation-in-part of U.S. application Ser. No. 09/396,347, filed Sep. 14, 1999 (issued as U.S. Pat. No. 6,506,384) which was a Continuation-in-part of U.S. application Ser. No. 09/001,984 filed Dec. 31, 1997 (issued as U.S. Pat. No. 6,245,331) which claimed priority from U.S. Provisional Appln No. 60/034,003 filed Dec. 31, 1996.

STATEMENT OF RIGHTS TO INVENTIONS MADE UNDER FEDERALLY SPONSORED RESEARCH

This invention was funded in part by grants and contracts from the National Institute of Allergy and Infectious Diseases, National Institutes of Health, and from the Department of Veterans Affairs, which provides to the United States government certain rights in this invention.

BACKGROUND OF THE INVENTION

1. Field of the Invention

The invention in the fields of microbiology and medicine relates to methods for rapid early detection of mycobacterial disease in humans based on the presence of antibodies to particular "early" mycobacterial protein antigens, and reactive epitopes thereof, which have not been previously recognized for this purpose. Assay of such antibodies on selected mycobacterial proteins, peptides thereof, or fusion polypeptides (peptide multimers, polyproteins) permits diagnosis of TB earlier than has been heretofore possible. Also provided is a surrogate marker for screening populations at risk for TB, in particular subjects infected with human immunodeficiency virus (HIV).

2. Description of the Background Art

Estimates by the World Health Organization (WHO) in 1995 suggested that approximately 90 million new cases of tuberculosis ("TB") will occur during the coming decade leading to about 30 million deaths (Raviglione, M C et al., 1995, *JAMA*. 273:220-226). The spread of HIV in populations already having a high incidence of TB has resulted in a resurgence of TB all over the world (Raviglione, M C et al., 1992, *Bull WHO* 70:515-526; Harries A. D., 1990, *Lancet*. 335:387-390) and has stimulated renewed interest in improved vaccines, diagnostics, drugs and drug delivery regimens for TB. Furthermore, the immune dysfunction caused by HIV infection leads to a high rate of reactivation of latent TB, increased susceptibility to primary disease, as well as an accelerated course of disease progression (Raviglione et al., 1992, supra; 1995, supra; Shafer R W et al., 1996, *Clin. Infect. Dis.* 22:683-704; Barnes P F et al., 1991, *N. Engl. J. Med.* 324:1644-1650; Selwyn P A et al., 1989, *N. Engl. J. Med.* 320:545-550).

The importance of cellular immunity for protection against TB is well established. Much of the work in this field is focused on defining the antigens of the causative bacterium, *Mycobacterium tuberculosis* (*M. tuberculosis*; also abbreviated herein as "Mtb") that can elicit effective immunity and on understanding the role of various cell populations in host-pathogen interactions (Andersen, P et al., 1992, *Scand. J. Immunol.* 36:823-831; Havlir, D V et al., 1991, *Infect. Immun.* 59:665-670; Orme, I M et al., 1993, *J. Infect. Dis.* 167:1481-1497).

Delayed hypersensitivity measured as cutaneous immune reactivity to a purified protein derivative of Mtb (abbreviated "PPD") has been the only accepted marker available for detection of latent infection with Mtb. However, the sensitivity of the PPD skin test is substantially reduced during HIV infection (Raviglione et al., 1992, supra, 1995, supra; Graham N M H et al., 1991, *JAMA* 267:369-373; Huebner R E et al., 1994, *Clin. Infect. Dis.* 19:26-32; Huebner R E et al., 1992, *JAMA* 267:409-410; Caiaffa W T et al., 1995, *Arch. Intern. Med.* 155:2111-2117). Furthermore, vaccination with a closely related mycobacterium *Bacillus* Calmette-Guerin (BCG) or previous exposure to other mycobacterial species can lead to false positive results in a PPD skin test. Not only does PPD reactivity fail to distinguish active, subclinical disease from latent infection, but the time between a positive skin test and development of clinical disease may range from months to several years (Selwyn P A et al., supra).

Because of the susceptibility of immunocompromised individuals to TB, the U.S. Centers for Disease Control and Prevention has recommended preventive isoniazid therapy for all HIV seropositive (HIV$^+$), PPD-positive (PPD$^+$) individuals. However, the optimal time for such therapy is not clear and, ideally, should coincide with replication of previously latent bacteria. Unnecessary therapy must be minimized because prolonged isoniazid treatment can have serious toxic side effects (Shafer et al., supra). The impact of such treatment on emergence of drug resistant bacteria is still unclear. The use of preventive therapy in developing countries is seriously limited by the high frequency of PPD$^+$ individuals coupled with the lack of adequate medico-social infrastructure and economic resources. High risk populations are also found in the United States, primarily intravenous drug users, homeless people, prison inmates and residents of slum areas (Fitzgerald, J M et al., 1991, *Chest* 100:191-200; Graham et al., supra; Friedman, L N et al., 1996, *New Engl. J. Med.* 334:828-833) as well as household contacts of TB patients. Thus, discovery of additional surrogate markers for early detection and prompt treatment of active, subclinical TB in such high risk populations is urgently required.

Antibody responses in TB have been studied for several decades primarily for the purpose of developing serodiagnostic assays. Although some seroreactive antigens/epitopes have been identified, interest in antibody responses to Mtb has waned because of the lack of progress in simple detection of corresponding antibodies. Studies using crude antigen preparations revealed that healthy individuals possess antibodies that cross-react with several mycobacterial antigens presumably elicited by exposure to commensal and environmental bacteria and vaccinations (Bardana, E J et al., 1973, *Clin. Exp. Immunol.* 13:65-77; Das, S et al., 1992, *Clin. Exp. Immunol.* 89:402-406; Del Giudice, G et al., 1993, *J. Immunol.* 150:2025-2032; Grange, J M, 1984, *Adv. Tuberc. Res.* 21:1-78; Havlir, D V et al., supra; Ivanyi, J et al., 1989, *Brit. Med. Bull.* 44:635-649; Verbon, A et al., 1990, *J. Gen. Microbiol.* 136:955-964). Several mycobacterial antigens have been isolated and characterized (Young, D B et al., 1992, *Mol. Microbiol.* 6:133-145), including the 71 kDa DnaK, 65 kDa GroEL, 47 kDa elongation factor tu, 44 kDa PstA homologue, 40 kDa L-alanine dehydrogenase, 38 kDa PhoS, 23 kDa superoxide dismutase, 23 kDa outer membrane protein, 12 kDa thioredoxin, and the 14 kDa GroES. A majority of these antigens bear significant homology to the analogous proteins in other mycobacteria and non-mycobacterial prokaryotes (Andersen, A B et al., 1992, *Infect. Immun.* 60:2317-2323; Andersen, A B et al., 1989, *Infect. Immun.* 57:2481-2488; Braibant, M et al., 1994, *Infect. Immun.* 62:849-854; Carlin, N et al., 1992, *Infect. Immun.* 60:3136-3142; Garsia, R J et al., 1989, *Infect. Immun.* 57:204-212; Hirschfield, G R et al., 1990, *J. Bacteriol.* 172:1005-1013; Shinnick, T M et al., 1989, *Nucl. Acids Res.* 17:1254; Shinnick, T M et al., 1988, *Infect. Immun.* 56:446-451; Wieles, B et al., 1995, *Infect. Immun.* 63:4946-4948; Young, D B et al., supra; Zhang, Y et al., 1991, *Mol. Microbiol.* 5:381-391). Thus, almost all individuals (healthy or diseased) have antibodies to epitopes of conserved regions of these antigens. These antibodies are responsible for the uninformative (and possibly misleading) cross-reactivity observed with crude Mtb antigen preparations (Davenport, M P et al., 1992, *Infect. Immun.* 60:1170-1177; Grandia, A A et al., 1991, *Immunobiol.* 182:127-134; Meeker, H C et al., 1989, *Infect. Immun.* 57:3689-3694; Thole, J et al., 1987, *Infect. Immun.* 55:1466-1475).

Because such cross-reactive antibodies would mask the presence of antibodies specific for Mtb antigens, some of the purified antigens such as the 38 kDa PhoS, the 30/31 kDa "antigen 85" (discussed in more detail below), 19 kDa lipoprotein, 14 kDa GroES and lipoarabinomannan have been prepared and tested (Daniel, T et al., 1985 *Chest.* 88:388-392; Drowart, L et al., 1991, *Chest.* 100:685-687; Jackett, P S et al., 1988, *J. Clin. Microbiol.* 26:2313-2318; Ma, Y et al., 1986, *Am Rev Respir Dis* 134:1273-1275; Sada, E et al., 1990, *J. Clin. Microbiol.* 28:2587-2590; Sada, E D et al., 1990, *J. Infect. Dis.* 162:928-931; Van Vooren, J P et al., 1991, *J. Clin. Microbiol.* 29:2348-2350). It is noteworthy that the choice of which antigen to test was dictated primarily by (a) its availability, (b) its immunodominance in animal immunizations, or (c) ease of its biochemical purification. None of these criteria take into account the reactivity of the antigen which occurs naturally in the human immune response to mycobacterial diseases. For a time, use of the 38 kDa antigen provided the highest serological sensitivity and specificity (Daniel, T M et al., 1987, *Am Rev Respir Dis* 135:1137-1151; Harboe, M et al., 1992, *J. Infect. Dis.* 166:874-884; Ivanyi, J et al., 1989, supra). However, in contrast to antibodies against the antigens discovered by the present inventors, the presence of anti-38 kDa antibodies is associated primarily with treated, advanced and recurrent TB (Bothamley, G H et al., 1992, *Thorax.* 47:270-275; Daniel et al., supra Ma et al., supra.

One convention in mycobacterial protein nomenclature is the use of MPB and MPT numbers. MPB denotes a protein purified from *M. bovis* BCG followed by a number denoting its relative mobility in 7.7% polyacrylamide gels at a pH of 9.5. MPT denotes a protein isolated from Mtb. In proteins examined prior to this invention, no differences in the N-terminal amino acid sequence were shown between these two mycobacterial species.

Wiker and colleagues have studied a family of secreted Mtb proteins which include a complex of 3 proteins termed antigens 85A, 85B and 85C (also known as the "85 complex" or "85cx") (Wiker, H. G. et al., 1992, *Scand. J. Immunol.* 36:307-319; Wiker, H. G. et al., 1992, *Microbiol. Rev.* 56:648-661). The corresponding components of Mtb are also actively secreted. The 85 complex is considered the major secreted protein constituent of mycobacterial culture fluids though it is also found in association with the bacterial surface. In most SDS-polyacrylamide gel electrophoresis (SDS-PAGE) analyses, 85A and 85C are not properly resolved, whereas isoelectric focusing resolves three distinct bands.

Genes encoding six of the secreted proteins: 85A, 85B, 85C, "antigen 78" (usually referred to as the 38 kDa protein), MPB64 and MPB70 have been cloned. Three separate genes located at separate sites in the mycobacterial genome encode 85A, B and C (Content, J. et al., 1991, *Infect. Immun.* 59:3205-3212). A gene encoding the antigen known as MPT-32 (reported as a 45/47 kDa secreted antigen complex) has been cloned, sequenced and expressed (Laqueyrerie, A. et al., 1995, *Infec. Immun.* 63:4003-4010) and designated as the apa gene. The need continues for further elucidation of the biochemistry and immunochemistry of Mtb proteins and glycoproteins which are potentially important as serodiagnostic tools.

The following list shows the molecular masses of the individual components of antigen 85 complex plus two additional antigens (in SDS-PAGE) as described by Wiker and colleagues, along with alternative nomenclatures:

| | | |
|---|---|---|
| Ag85A | = MPT44 | = 31 kDa |
| Ag85B | = MPT59 | = 30 kDa |
| Ag85C | = MPT45 | = 31.5 kDa |
| MPT64 | = 26 kDa | |
| MPT51 | = 27 kDa | |
| Ag78 | — | = 38 kDa |
| | MPT32 | = 45/47 kDa (found to be 38/42 kDa by the present inventors) |

Wiker's group studied cross-reactions between five actively secreted Mtb proteins by crossed immunoelectrophoresis, SDS-PAGE with immunoblotting and enzyme immunoassay (EIA) using (1) polyclonal rabbit antisera to the purified proteins and (2) a mouse monoclonal antibody ("mAb"). The mAb HBT4 reacted with the MPT51 protein.

The aligned amino acid sequences listed below illustrate the homology of a fragment of 85A, 85B, 85C, 1 and MPT64. The numbers at the top correspond to the part of the sequence shown. The N-terminal sequences were determined on isolated proteins and aligned by visual inspection. The sequence from position 66 to 91 of MPT64 is the sequence deduced from the cloned gene.

| | 1 | 5 | 10 | 15 | 20 | 25 | 30 | 35 | SEQ ID NO |
|---|---|---|---|---|---|---|---|---|---|
| 85A(1-39) | FSRPGLPVEYLQVPS | | | | PSMGRDIKVQFQSGGANSP | | | ALYLL | 1 |
| 85B(1-39) | FSRPGLPVEYLQVPS | | | | PSMGRDIKVQFQSGGNNSP | | | AVYLL | 2 |
| 85C(1-37) | FSRPGLPVEYLQVPSA | | | | SMGRDIKVQFQGGG | | | PHAVYLL | 3 |
| MPT51(1-32) | APYENLMVPS | | | | PSMGRDIPVAFLAGG | | | PHAVYLL | 4 |
| MPT64(66-91) | APYE | | LNITSATYQS | | | AIPPRG | | TQAVVL | 5 |

The N-terminal sequence of MPT51 showed 72% homology with the sequence of the Ag 85 components (when P at position 2 is aligned with P at position 7 of the three Ag 85 components.

Studies of TB patients showed that assays of antibodies to the Ag 85 complex had a sensitivity of about 50%. With regard to specificity, the Ag 85 components are highly cross-reactive so that positive responses are expected (and found) in healthy controls, particularly in geographic areas of high exposure to atypical mycobacteria. The different degree of specificity is thus highly dependent on the kind of control subjects used. It is noteworthy that traditional BCG vaccination does not appear to induce a significant antibody response, though it is interesting that antibodies to mycobacterial antigens increased when anti-TB chemotherapy was initiated. A number of studies have examined antibodies to various Mtb antigen in TB sera or sera of patients with other diseases. See, for example, Espitia, C et al., 1989, *Clin Exp Immunol* 77:373-377; Van Vooren, J P et al., 1991, *J. Clin. Microbiol.* 29:2348-2350; Wiker et al. (supra). C. Espitia et al., 1995, *Infect. Immun.* 63:580-584, found reciprocal cross-reactivity between a Mtb 50/55 kDa protein and a *M. bovis* BCG 45/47 kDa antigen using a rabbit polyclonal antiserum against the *M. bovis* protein and a mAb against the Mtb antigen. Both antigens were secreted glycoproteins. The N-terminal sequences and total amino acid content of these proteins were very similar. 2D gel electrophoresis showed at least seven different components in the Mtb 50/55 kDa antigen. In solid-phase immunoassays, purified Mtb 50/55 kDa protein was recognized by sera from 70% of individuals (n=77) with pulmonary TB. The N-terminus of the Mtb 41 kDa antigen known as MPT32 was very similar to the N-termini of the 50/55 kDa- and the 45-47 kDa proteins. The authors speculated about a diagnostic potential for these antigens based on these observation However, the potential of this antigen as an early diagnostic agent for TB was neither analyzed nor even suggested.

Importantly, there has been a deficiency in the art of analysis of antibodies at different stages of disease, which is one of the primary objectives addressed by this invention. None of the antigens studied so far, with the possible exception of MPT32 (as will be described herein) has emerged as a suitable candidate for development of a diagnostic assay for early stages of TB. Since antigens/epitopes recognized during natural infection and disease progression in humans may differ substantially from those recognized by animals upon artificial immunization (Bothamley, G. et al., 1988, *Eur. J. Clin. Microbiol. Infect. Dis.* 7:639-645; Calle, J. et al., 1992, *J. Immunol.* 149:2695-2701; Hartskeerl, R. A. et al., 1990, *Infect. Immun.* 58:2821-2827; Laal, S. et al., 1991, *Proc. Natl. Acad. Sci. USA.* 88:1054-1058; Meeker, H. C. et al., 1989, *Infect. Immun.* 57:3689-3694; Verbon, A., 1994, *Trop. Geog. Med.* 46:275-279), there is a pressing need in the art for selection of antigens based on their ability to stimulate the human immune system. This would permit the identification of useful protein antigens and peptide epitopes for use in the design of diagnostic assays for early detection of TB and for vaccines.

TB in HIV Infected Subjects

Although the literature on TB infection in subjects not infected with HIV is extensive, reports on antibody responses of HIV/TB patients to Mtb, have been scant and controversial. Farber, C. et al., 1990, *J. Infect. Dis*, 162:279-280, reported the presence of antibodies to the p32 antigen (same as 85A) in 7 of 8 HIV/TB patients. Da Costa, C. et al., 1993, *Clin. Exp. Immunol.* 91:25-29, reported the presence of anti-lipoarabinomannan (LAM) antibodies in 35% of such patients. Barer, L. et al., 1992, *Tuber. Lung. Dis.* 73:187-191, reported anti-PPD antibodies in 36% of HIV/TB patients. Martin-Casabona, N. et al., 1992, *J. Clin. Microbiol.* 30:1089-1093, reported anti-sulfolipid (SLIV) antibodies in 73% of their patients. In addition, van Vooren, P. et al., 1988, *Tubercle.* 69:303-305, reported that anti-p32 antibodies were detectable in an HIV/TB patient for several months prior to clinical manifestation of TB. In contrast, analysis of responses to Ag60 (Saltini C. et al., 1993, *Am Rev Respir Dis* 145:1409-1414; van der Werf, T. S. et al., 1992. *Med Microbiol Immunol* 181:71-76) and Ag85B (McDonough, J. A. et al., 1992, *J. Lab. Clin. Med.* 120:318-322) failed to detect antibodies in these patients.

Hence, there is a particular need in the art for methods to detect TB infections at early stages in HIV patients since they comprise one of the largest populations at risk for TB throughout the world.

Antibodies in Urine

A number of laboratories have reported on antibodies, mainly to infectious agents, in urine. For example, Takahashi S; et al. (*Clin Diagn Lab Immunol*, 1998, 5:24-27) found antibodies to rubella virus in urine and serum samples from healthy individuals who underwent rubella vaccination. Shutov A M et al. *Arkh* (*RUSSIA*) 1996, 68:35-37 detected antibodies in urine to the virus causing hemorrhagic fever with renal syndrome (HFRS) and concluded that detection of antibodies to the virus both in the blood and urine can be used for earlier diagnosis Vereta L A; et al. (*Vopr Virusol* (*RUSSIA*) 1993, 38:18-21) used a commercial diagnostic indirect immunofluorescence assay to detection antibodies to the hantavirus in the urine of patients with HFRS. Koopmans M et al. (*J Med Virol*, 1995, 46:321-328) demonstrated presence of antibodies to human cytomegalovirus (HCMV) in urine samples by ELISA and immunoblot. Zhang X et al. (*J Med Virol*, 1994, 44:187-191) used commercial immunoassays to detect antibodies to hepatitis C virus (HCV) in urine. The same group (Constantine N T et al., *Am J Clin Pathol*, 1994, 101:157-161) detected antibodies to HIV in urine. Perry K R et al., *Med Virol* 1992, 38:265-270, detected IgG and IgM antibodies to hepatitis A and hepatitis B core antigens in urine specimens.

A group of Japanese investigates (Hashida S et al., *J Clin Lab Anal*, 1994, 8:237-246; Hashinaka K et al., *J Clin Microbiol* 1994, 32:819-22; Hashida S et al., *J Clin Lab Anal* 1994, 8:149-156 Hashida S et al., *J Clin Lab Anal* 1994, 8:86-95) diagnosed HIV-1 infection in asymptomatic carriers by detecting IgG antibody to HIV-1 in urine using an ultrasensitive enzyme immunoassay (immune complex transfer enzyme immunoassay) with recombinant proteins as antigen. They reported that sensitivity could be improved by a longer assay of bound enzyme activity by using concentrated urine samples and by the combined use of three different recombinant HIV antigens.

Urnovitz H B et al., (*Lancet* Dec. 11, 1993, 342:1458-9), discovered that 7 individuals who were negative for HIV-1 antibody in a licensed serum EIA were positive in a urine EIA and western blot (WB). Connell J A et al., *J Med Virol* 1993, 41:159-64, described a rapid, simple, and robust IgG-capture enzyme-linked immunosorbent assay (GACELISA) suitable for the detection of anti-HIV 1 and 2 antibodies in saliva and urine. An earlier study from this laboratory (Connell J A et al., *Lancet*, 1990, 335:1366-1369) described anti-HIV antibodies in urine by GACELISA). Gershy-Damet G M et al. *Trans R Soc Trop Med Hyg* 1992, 86:670-671, used these assays successfully for urinary diagnosis of HIV-1 and HIV-2 in Africa, using unprocessed saliva and urine specimens. They found the assay to be as accurate as conventional EIAs on serum tested under similar.

Dr. A. Friedman-Kien and his colleagues have examined paired urine and serum samples in a search for antibodies to hepatitis B surface antigen (HBs), hepatitis B core antigen (HBc), CMV and HIV in paired urine and serum samples from the same HIV-infected individuals (Cao Y et al., 1989, *AIDS. Res. Hum. Retrovir.* 5:311). In all individuals with anti-HIV antibodies in serum, anti-HIV antibodies were found in their urine; no such correlation was observed for HBs and CMV antibodies. The anti-HIV urine antibodies were of the IgG class, and gp160 and gp120 were the most consistently recognized proteins. Based on these observations, a urine based diagnostic assay for HIV-1 was developed.

In view of the prevalence of TB in the HIV-infected individuals, especially in the developing countries, and the risks and costs involved in collection of blood/serum for serodiagnosis, the present inventors evaluated the urine of TB patients for presence of anti-mycobacterial antibodies. They reasoned that since Mtb infects the mucosal surfaces in the lung, it may induce antibodies in mucosal tissues resulting in the presence of antibodies in the urine. The positive results of these studies are presented below. The ability to use urine as the sample material will make the test extremely attractive to public health officials and to industry.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors have systematically analyzed the reactivity of sera and urine from TB patients with antigens from Mtb to delineate the major targets of human antibody responses which occur relatively early in the progression of the infection to disease. They observed that initial immunoadsorption of patient sera with *E. Coli* antigens successfully reduced interference by cross-reactive antibodies, thus allowing a new approach to serological studies. The immunoadsorbed sera allowed identification of a number of antigens of Mtb that are recognized by antibodies in a large proportion of patients, and during earlier stages of disease progression. These antigens are therefore useful tools in methods of diagnosing TB. Prominent among these antigens is a high molecular weight secreted protein of 88 kDa or 85 kDa (depending on conditions as will be described below). This protein is termed "the 88 kDa protein" and, as discovered later, as the product of the glcB gene, is also termed GlcB (see below).

In addition to its utility for early diagnosis of mycobacterial disease in a subject prior to the development of radiographic or bacteriological evidence of the disease, the present invention also provides for the first time a surrogate marker that can be used in an inexpensive screening method in individuals at heightened risk for developing TB. This utility was discovered by applying the approach described herein to analyze antibody responses of HIV-infected TB patients (HIV/TB) to the secreted antigens of Mtb during different stages of disease progression. A majority of the HIV/TB patients had detectable antibodies to the secreted antigens of Mtb for months, even years, prior to the clinical manifestation of active tuberculous disease. These patients are termed "HIV/pre-TB". However, compared to the TB patients not infected with HIV (designated "non-HIV/TB"), HIV/TB patients had significantly lower levels of antibodies which showed specificity for a restricted repertoire of Mtb antigens. Antibodies to the 88 kDa antigen mentioned above were present in about 75% of the HIV/pre-TB sera patients who eventually developed clinical TB. HIV/TB patients who failed to develop anti-Mtb antibodies did not differ in their lymphocyte profiles from those that were antibody-positive. These discoveries led to the invention of a serological surrogate marker for active pre-clinical TB in HIV-infected subjects as well as in any other high risk population. Thus, this invention provides a new method for early detection of Mtb infection in immunocompromised subjects. Exploitation of this discovery should make a significant contribution to the early detection of the tubercular disease and will permit a more rapid institution of therapy.

The present invention is directed to an antigenic composition useful for early detection of *M. tuberculosis* disease or infection or for immunizing a subject against *M. tuberculosis* infection, comprising (a) a peptide selected from the group consisting of (1) CGTD-GAEKGPTYNKVRGDK (SEQ ID NO:108); (2) KIGIM-DEERRTTVNLKAC (SEQ ID NO:109); (3) ELAWAP-DEIREEVDNNC (SEQ ID NO:110); (4) HRRRREFKARAAEKPAPSDRAG (SEQ ID NO:111); (5) ARDELQAQIDKWHRRR (SEQ ID NO:112); (6) LNRDRNYTAPGGGQ (SEQ ID NO:113); (7) GAPQLGRWKWHDPWV (SEQ ID NO:114) (8) VGNL-RIARVLYDF (SEQ ID NO:117); (9) QAQIDKWHR-RRVI (SEQ ID NO:126); (10) WHRRRVIEPIDMD (SEQ ID NO:127); (11) IEPIDMDAYRQFL (SEQ ID NO:128); (12) ITTTAGPQLVVPV (SEQ ID NO:134); (13) PQLV-VPVLNARFA (SEQ ID NO:135); (14) VLNARFAL-NAANA (SEQ ID NO:136); (15) ALNAANARWGSLY (SEQ ID NO:137); (16) ARWGSLYDALYGT (SEQ ID 0:13); (17) SVLLINHGLHIEI (SEQ ID NO:154); (18) HGLHIEILIDPES (SEQ ID NO:155); (19) GGQFTLPGRSLMF (SEQ ID NO:170); (20) FVRN-VGHLMTNDA (SEQ ID NO:172); (21) DRVVFINTG-FLDR (SEQ ID NO:191); (22) NCQSILGYVVRWV (SEQ ID NO:216); and (23) GYVVRWVDQGVGC (SEQ ID NO:217).

with the proviso that the composition is not the full length protein having the sequence SEQ ID NO:106 or SEQ ID NO:107;

(b) a variant or functional derivative of the peptide of (a) which retains reactivity with antibodies specific for the GlcB or MPT51; or (c) a combination of two or more of any of the peptides (1)-(23) of (a) or the variants or functional derivatives of (b).

In one embodiment, the above antigenic composition is a fusion polypeptide that includes:

(a) one or more of the peptides (1)-(23) or the variants, linked to (b) one or more proteins selected from the group consisting of SEQ ID NO:106, SEQ ID NO:107 and another early Mtb antigen.

wherein the fusion polypeptide includes an optional linker or linkers linking any two or more of the proteins or peptides.

Also included is an antigenic composition as above which is:

(a) a peptide multimer having the formula $$P^1_n$$

wherein $P^1$ is any of peptides (1)-(23) or a substitution variant thereof, and n=2-8, (b) a peptide multimer having the formula

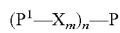

wherein $P^1$ and $P^2$ are any of peptides (1)-(23) or conservative substitution variants thereof, and wherein
(i) $P^1$ and $P^2$ may be the same or different and each occurrence of $P^1$ in the $P^1$—$X_m$ structure may be a different peptide or variant from its adjacent neighbor; and
(ii) X is (A) $C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1 and n=1-7; or (B) $Gly_z$ wherein, z=1-6, and wherein the peptide multimer reacts with an antibody specific for the GlcB or MPT51 protein.

The invention is also directed to an antigenic composition as above which is a recombinant peptide multimer having the formula:

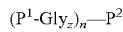

wherein $P^1$ and $P^2$ are any of peptides (1)-(23) or conservative substitution variants thereof, and wherein
(a) $P^1$ and $P^2$ may be the same or different and each occurrence of $P^1$ in the $P^1$-$Gly_z$ structure may be a different peptide or variant from its adjacent neighbor;
(b) n=1-100 and z=0-6, and wherein the peptide multimer reacts with an antibody specific for the GlcB or MPT51 protein.

An antigenic composition useful for early detection of M. tuberculosis disease or infection may comprise one or more peptides in a mixture or linked in a peptide multimer or fusion protein, which one or more peptides are derived from or have a sequence corresponding to a fragment of an early M. tuberculosis antigen which antigen is characterized as being
(i) reactive with antibodies found in tuberculosis patients who are in a stage of disease prior to the onset of sputum smear-positivity and cavitary pulmonary lesions, and
(ii) non-reactive with sera from healthy control subjects or healthy subjects with latent inactive tuberculosis the composition being substantially free of other M. tuberculosis proteins which are not early M. tuberculosis antigens as characterized above.

Also provided are methods using the above antigenic compositions. A preferred method for the early detection of mycobacterial disease or infection in a subject comprises assaying a biological fluid sample from a subject suspected of having active TB for the presence of antibodies specific for the above peptide or variant, fusion protein or peptide multimer, wherein the presence of the antibodies is indicative of the presence of the disease or infection.

In the above methods, the biological fluid sample is preferably taken from a subject having symptoms of active tuberculosis, but before the onset of symptoms identifiable as advanced tuberculosis that is distinguished by (a) smear positivity of sputum or other pulmonary associated fluid for acid-fast bacilli, (b) cavitary pulmonary lesions, or both (a) and (b).

Generally, the method includes, before the assaying, the step of obtaining the biological fluid sample from the subject The above method preferably includes, prior to the assaying step, removing from the sample antibodies specific for cross-reactive epitopes or antigens between proteins present in M. tuberculosis and in other bacterial genera, for example, by immunoadsorption of the sample with E. coli antigens.

The above method may further comprise assaying the sample for the presence of antibodies specific for one or more additional early antigens of M. tuberculosis selected from the group consisting of:
(a) M. tuberculosis protein GlcB protein having an amino acid sequence SEQ ID NO:106;
(b) M. tuberculosis MPT51 having an amino acid sequence SEQ ID NO:107;
(c) a protein characterized as M. tuberculosis antigen 85C;
(d) a glycoprotein characterized as M. tuberculosis antigen MPT32; and
(e) a fusion proteins comprising one or more of (a)-(d).

The preferred subject in the above methods is a human, such as human infected with HIV-1 or at high risk for tuberculosis.

In a preferred embodiment of the above method the biological fluid sample is serum, urine or saliva.

The method may further include performance of a test that detects mycobacterial bacilli in a sample of sputum or other body fluid of the subject.

The invention is also directed to a kit useful for early detection of M. tuberculosis disease, the kit comprising:
(a) an antigenic composition as above, and
(b) reagents necessary for detection of antibodies which bind to the peptides.

The kit may also comprise one or more early antigens of M. tuberculosis, for example, an antigens is selected from the group consisting of:
(a) M. tuberculosis protein GlcB protein having an amino acid sequence SEQ ID NO:106;
(b) M. tuberculosis MPT51 having an amino acid sequence SEQ ID NO:107;
(c) a protein characterized as M. tuberculosis antigen 85C;
(d) a glycoprotein characterized as M. tuberculosis antigen MPT32; and
(e) a fusion protein comprising one or more of (a)-(d).

DESCRIPTION OF THE PREFERRED EMBODIMENTS

Figure 1:
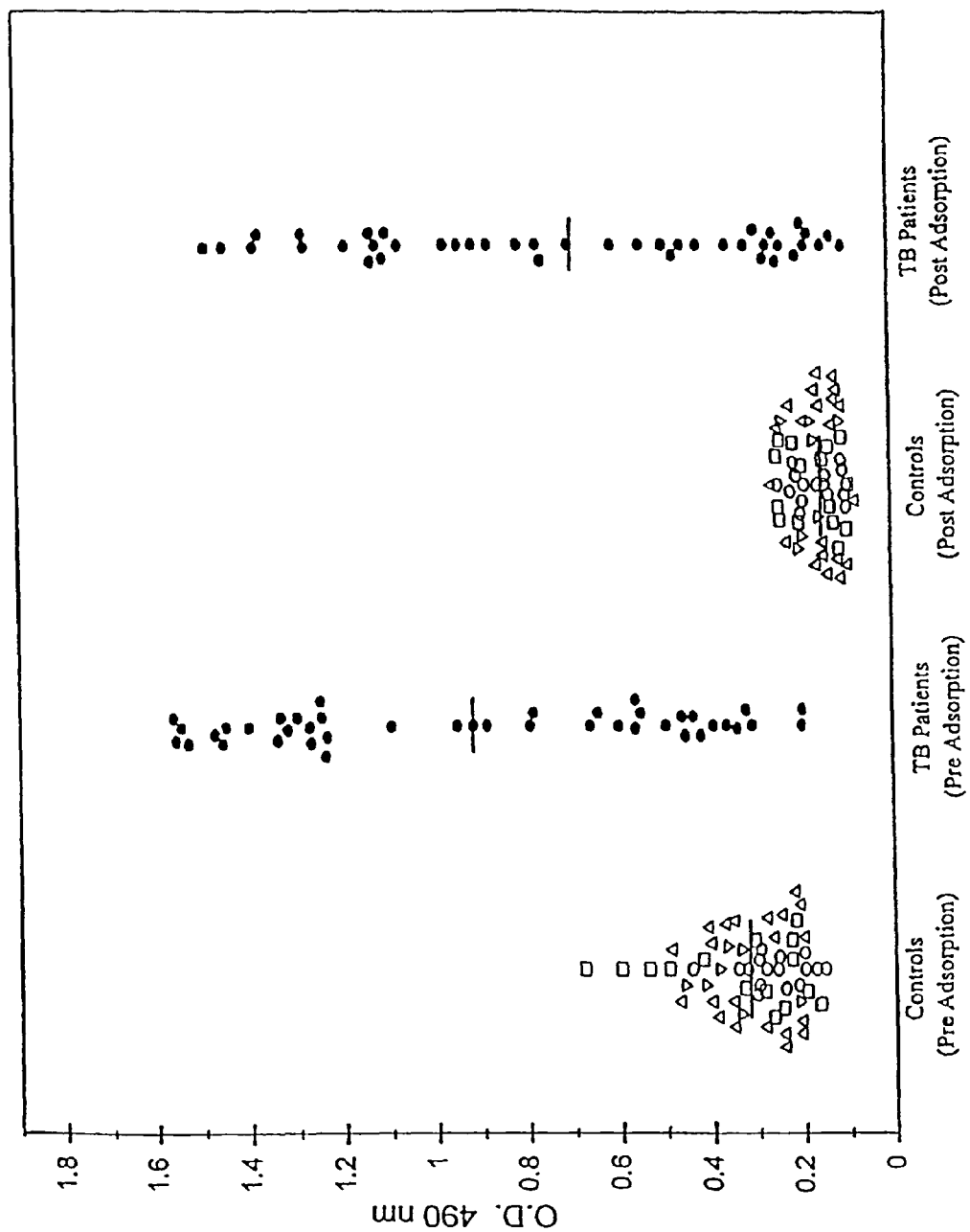
FIG. 1 shows the reactivity of sera from $TB^{neg}$ $HIV^{neg}$ $PPD^+$ controls (◯); $TB^{neg}$ $HIV^{neg}$ $PPD^{neg}$ controls (▽), $TB^{neg}$, $HIV^+$, asymptomatic controls (Δ); and TB patients (●) with LAM-free culture filtrate proteins (LFCFP) of Mtb $H_{37}Rv$, before and after adsorption with E. coli lysate. Values are individuals OD's with the mean shown as a horizontal bar.

In the following description, reference will be made to various methodologies known to those of skill in the art of immunology, cell biology, and molecular biology. Publications and other materials setting forth such known methodologies to which reference is made are incorporated herein by reference in their entireties as though set forth in full. Standard reference works setting forth the general principles of immunology include A. K. Abbas et al., *Cellular and Molecular Immunology* (Fourth Ed.), W.B. Saunders Co., Philadelphia, 2000; C. A. Janeway et al., *Immunobiology. The Immune System in Health and Disease*, Fourth ed., Garland Publishing Co., New York, 1999; Roitt, I. et al., *Immunology*, (current ed.) C.V. Mosby Co., St. Louis, Mo. (1999); Klein, J., *Immunology*, Blackwell Scientific Publications, Inc., Cambridge, Mass., (1990). Monoclonal antibodies (mAbs) and methods for their production and use are described in Kohler and Milstein, *Nature* 256:495-497 (1975); U.S. Pat. No. 4,376,110; Hartlow, E. et al., *Antibodies: A Laboratory Manual*, Cold Spring Harbor Laboratory Press, Cold Spring Harbor, N.Y., 1988); *Monoclonal Antibodies and Hybridomas: A New Dimension in Biological Analyses*, Plenum Press, New York, N.Y. (1980); H. Zola et al., in *Monoclonal Hybridoma Antibodies: Techniques and Applications*, CRC Press, 1982)). Immunoassay methods are also described in Coligan, J. E. et al., eds., *Current Protocols in Immunology*, Wiley-Interscience, New York 1991 (or current edition); Butt, W. R. (ed.) *Practical Immunoassay: The State of the Art*, Dekker, New York, 1984; Bizollon, Ch. A., ed., *Monoclonal Antibodies and New Trends in Immunoassays*, Elsevier, New York, 1984; Butler, J. E., ELISA (Chapter 29), In: van Oss, C. J. et al., (eds), *IMMUNOCHEMISTRY*, Marcel Dekker, Inc., New York, 1994, pp. 759-803; Butler, J. E. (ed.), *Immunochemistry of Solid-Phase Immunoassay*, CRC Press, Boca Raton, 1991; Weintraub, B., *Principles of Radioimmunoassays*, Seventh Training Course on Radioligand Assay Techniques, The Endocrine Society, March, 1986; Work, T. S. et al., *Laboratory Techniques and Biochemistry in Molecular Biology*, North Holland Publishing Company, NY, (1978) (Chapter by T. Chard).

The present invention provides a diagnostic immunoassay method to detect and/or quantitate antibodies specific for mycobacterial antigens, in particular, antibodies developing early in the progression of *M. tuberculosis* infection to disease and before clinical manifestations of that disease. On the basis of such an assay, it is possible to detect TB earlier than ever before and to institute appropriate therapy. The best antigen available prior to this invention for serodiagnosis of TB was the 38 kDa secreted protein also known as Ag 78 (see above). However, the present invention permits detection of serological reactivity in subject who lack detectable antibodies to this 38 kDa antigen.

The immunoassay method is based upon the present inventors' discovery that certain Mtb antigens induce in humans an earlier response than do other antigens which elicit antibodies only after the disease is already clinically advanced. In HIV-infected subjects with dysfunctional immune systems, antibodies to some of these antigens are detectable long before TB is clinically manifest. Five secreted proteins have been identified as early antigens with diagnostic value. In particular a preferred early antigen is a 88 kDa secreted protein of Mtb GlcB, preferably enriched or semipurified (at least 50% pure) or highly purified (at least 95% pure, preferably at least 99% pure).

Also provided are epitope-bearing peptides from GlcB and from MPT51 that are reactive with TB sera and which are used in early diagnosis in the form of peptides (single peptide or mixtures), peptide multimers (synthetic or recombinant) comprising one or more different epitope-bearing peptides, or fusion polyproteins that comprise at least two full length early antigen proteins and may include additional epitopes based on peptides of the same or other Mtb proteins.

The present method is further based on the inventors' conception of the importance of first removing antibodies specific for cross-reactive antigens (which are not Mtb-specific) prior to analyzing the antigenic reactivity and specificity of serum from patients infected with Mtb on crude or semipurified antigenic preparations. However, once purified antigens are provided or epitope-specific competitive ELAs are established based on this invention (see, for example, Wilkins, E. et al., 1991, *Eur. J. Clin. Microbiol. Infect. Dis.* 10:559-563), the need for such prior absorption steps should be obviated.

As used herein, the term "early" and "late" in reference to (1) Mtb infection or disease, or the subject having the infection or disease, (2) the antibody response to an Mtb antigen, (3) an Mtb antigen itself or (4) a diagnostic assay, are defined in terms of the stage of development of TB. Early and late (or advanced) TB are defined in the table below.

Thus, a subject with early TB is asymptomatic or, more typically, has one or more "constitutional symptoms" (e.g., fever, cough, weight loss). In early TB, Mtb bacilli are too few to be detectable as acid-fast bacilli in smears of sputum or other body fluid, primarily those fluids associated with the lungs (such as bronchial washings, bronchioalveolar lavage, pleural effusion). However, in these subjects, Mtb bacilli are present and culturable, i.e., can be grown in culture from the above body fluids. Finally, early TB subjects may have radiographically evident pulmonary lesions which may include infiltration but without cavitation. Any antibody present in such early stages is termed an "early antibody" and any Mtb antigen recognized by such antibodies is termed an "early antigen." The fact that an antibody is characterized as "early" does not mean that this antibody is absent in advanced TB. Rather, such antibodies are expected to persist across the progression of early TB to the advanced stage.

| | |
|---|---|
| Early TB | 1. Smear of sputum, bronchial washing, bronchoalveolar lavage or pleural effusion is negative for acid fast bacilli |
| | 2. Direct culture of sputum, bronchial washing, bronchoalveolar lavage or pleural effusion is positive for acid fast bacilli |
| | 3. Chest x-ray is normal or shows infiltration in the lungs |
| | 4. Constitutional symptoms are present (fever, cough, appetite and weight loss) |
| Late/ Advanced TB | 1. Smear of sputum, bronchial washing, bronchoalveolar lavage or pleural effusion is positive (with possible hemoptysis) |
| | 2. Direct culture of sputum, bronchial washing, bronchoalveolar lavage or pleural effusion is positive |
| | 3. Chest x-ray shows cavitary lesions in the lungs |
| | 4. Constitutional symptoms are present (see above) |

Accordingly, the term "late" or "advanced" is characterized in that the subject has frank clinical disease and more advanced cavitary lesions in the lungs. In late TB, Mtb bacilli are not only culturable from smears of sputum and/or the other body fluids noted above, but also present in sufficient numbers to be detectable as acid-fast bacilli in smears of these fluids. Again, "late TB" or "late mycobacterial disease" is used interchangeably with "advanced TB" or "advanced mycobacterial disease." An antibody that first appears after the onset of diagnostic clinical and other characterizing symptoms (including cavitary pulmonary lesions) is a late antibody, and an antigen recognized by a late antibody (but not by an early antibody) is a late antigen.

To be useful in accordance with this invention, an early diagnostic assay must permit rapid diagnosis of Mtb disease at a stage earlier than that which could have been diagnosed by conventional clinical diagnostic methods, namely, by radiologic examination and bacterial smear and culture or by other laboratory methods available prior to this invention. (Culture positivity is the final confirmatory test but takes two weeks and more)

The present immunoassay typically comprises incubating a biological fluid, preferably serum or urine, from a subject suspected of having TB, in the presence of an Mtb antigen-containing reagent which includes one or more Mtb early antigens. They may be combined as mixtures or as polyproteins or peptide multimers based on units of epitope-bearing peptide. The binding of antibodies in the sample to the mycobacterial antigen(s) is then detected. By the term "biological fluid" is intended any fluid derived from the body of a normal or diseased subject which may contain antibodies, such as blood, serum, plasma, lymph, urine, saliva, sputum, tears, cerebrospinal fluid, bronchioalveolar lavage fluid, pleural fluid, bile, ascites fluid, pus and the like. Also included within the meaning of this term as used herein is a tissue extract, or the culture fluid in which cells or tissue from the subject have been incubated.

Mycobacterial Antigenic Compositions

The mycobacterial antigenic composition or preparation of the present invention may be one or a combination of isolated proteins or peptides of a M. tuberculosis secreted protein. As stated above, the combination may be produced as a mixture or as a polyprotein or peptide multimer.

The antigen composition may be a substantially purified or recombinantly produced preparation of one or more M. tuberculosis proteins or epitope-bearing peptides thereof. Alternatively, the antigen composition may be a partially purified or substantially pure preparation containing one or more M. tuberculosis epitopes which are capable of being bound by antibodies of a subject with TB. Such epitopes may be in the form of peptide fragments of the early antigen proteins or other "functional derivatives" of M. tuberculosis proteins or peptides as described below.

By "functional derivative" is meant a "fragment," "variant," "analogue," or "chemical derivative" of an early antigen protein, which terms are defined below. A functional derivative retains at least a portion of the function of the protein which permits its utility in accordance with the present invention—primarily the capacity to bind to an early antibody. A "fragment" refers to any subset of the molecule, that is, a shorter peptide. A "variant" refers to a molecule substantially similar to either the entire protein or fragment thereof. A variant peptide may be conveniently prepared by direct chemical synthesis or by recombinant means. A "chemical derivative" of the antigenic protein or peptide contains additional chemical moieties not normally part of the native protein (or of a peptide fragment). Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Four proteins or glycoproteins, identified in culture filtrates of Mtb, are the preferred early Mtb antigens (or sources of antigenic peptides) of the present invention. Thus, although these proteins are considered to be secreted proteins, they may also be present in cellular preparations of the bacilli. Thus, these early antigens are not intended to be limited to the secreted protein form. The proteins are characterized as follows:

(1) 88 kDa Protein (GlcB)

This protein was discovered by the present inventors as an Mtb secreted protein having a molecular mass of 88 kDa and an isoelectric point of about pH 5.2 when isolated from the culture filtrate. This protein migrated at a molecular mass range of 82-85 kDa in one co-inventor's laboratory (or 88 kDa in another co-inventor's laboratory) and a pI range of 5.12-5.19. This protein was originally thought to react with both mAb IT-42 and mAb IT-57, but it was later found that a second proteins in this MW range, the catalase/peroxidase (katG gene product) was reactive with those mAbs. Th 88 kDa protein is a major antigenic component of Fraction 15 (Example I) and Fraction 14 (Example II). This protein corresponds to the protein spot designated Ref. No. 124 in 2D gels now shown here (see U.S. Pat. No. 6,245,331 and WO 98/29132 (published 9 Jul. 1998) both incorporated by reference in their entirety; see also Tables 4 and 6, below). Hence, despite a small apparent difference in molecular mass, a single protein is intended (although different isoforms may be found to exist).

As is described in Example IV, the sequence of this protein was identified by the present inventors based on amino acid composition in relation to the Mtb genomic sequence obtained after the filing date of the present inventors' priority application Ser. No. U.S. 60/034,003, filed 31 Dec. 1996. This protein is the product of the Mtb glcB gene which encodes the malate synthase enzyme and is termed the GlcB protein. This protein has the amino acid sequence (SEQ ID NO:106) as shown below:

```
MTDRVSVGNL RIARVLYDFV NNEALPGTDI DPDSFWAGVD

KVVADLTPQN QALLNARDEL QAQIDKWHRR RVIEPIDMDA

YRQFLTEIGY LLPEPDDFTI TTSGVDAEIT TTAGPQLVVP

VLNARFALNA ANARWGSLYD ALYGTDVIPE TDGAEKGPTY

NKVRGDKVIA YARKFLDDSV PLSSGSPGDA TGFTVQDGQL

VVALPDKSTG LANPGQFAGY TGAAESPTSV LLINHGLHIE

ILIDPESQVG TTDRAGVKDV ILESAITTIM DFEDSVAAVD

AADKVLGYRN WLGLNKGDLA AAVDKDGTAF LRVLNRDRNY

TAPGGGQFTL PGRSLMFVRN VGHLMTNDAI VDTDGSEVFE

GIMDALFTGL IAIHGLKASD VNGPLINSRT GSIYIVKPKM

HGPAEVAFTC ELFSRVEDVL GLPQNTMKIG IMDEERRTTV

NLKACIKAAA DRVVFINTGF LDRTGDEIHT SMEAGPMVRK

GTMKSQPWIL AYEDHNVDAG LAAGFSGRAQ VGKGMWTMTE

LMADMVETKI AQPRAGASTA WVPSPTAATL HALHYHQVDV

AAVQQGLAGK RRATIEQLLT IPLAKELAWA PDEIREEVDN

NCQSILGYVV RWVDQGVGCS KVPDIHDVAL MEDRATLRIS

SQLLANWLRH GVITSADVRA SLERMAPLVD RQNAGDVAYR
```

-continued

PMAPNFDDSI AFLAAQELIL SGAQQPNGYT EPILHRRRRE

FKARAAEKPA PSDRAGDDAA R

Subsequent to the discovery of the 88 kDa protein and its utility as an early antigen by the present inventors (see U.S. Pat. No. 6,245,331 and WO 98/29132), Hendrickson R C et al., *J Clin Microbiol* 38:2354-2356 (2000), used serological proteome analysis in conjunction with tandem mass spectrometry to identify and sequence a protein they termed Mtb81 which they concluded may be useful for the diagnosis of TB, especially for patients coinfected with HIV. Recombinant Mtb81 tested by ELISA detected antibodies in 25/27 TB patients (92%) seropositive for HIV as well as in 38/67 individuals (57%) who were TB positive alone. No reactivity was observed in 11/11 individuals (100%) who were HIV seropositive alone. In addition, neither sera from PPD-negative (0/29) nor healthy (0/45) blood donors tested positive with Mtb81. Only 2/57 of PPD-positive individuals tested positive with Mtb81. Sera from individuals with smear-positive TB and seropositive for HIV but who had tested negative for TB using an assay for another antigen were tested for reactivity against Mtb81 as were sera from individuals with lung cancer and pneumonia. Mtb81 reacted with 26/37 HIV+/TB+ sera (70%) in this group, compared to 2/37 (5%) that reacted with a 38-kDa antigen. The authors concluded, as had the present inventors earlier, that Mtb81 may be a promising complementary antigen for the serodiagnosis of TB.

(2) Antigen 85C

This is an Mtb secreted protein having an apparent molecular weight of about 31 kDa and an isoelectric point of about pH 5.17. This protein is reactive with mAb IT-49 and has also been designated MPT45. Ag85C corresponds to the protein spot designated Ref. No. 119 in Table 4 or Table 6.

(3) MPT51

This Mtb secreted protein has an apparent molecular mass of about 27 kDa and an isoelectric point of about 5.91 and the amino acid sequence SEQ ID NO:107.

APYENLMVPS PSMGRDIPVA FLAGGPHAVY LLDAFNAGPD

VSNWVTAGNA MNTLAGKGIS VVAPAGGAYS MYTNWEQDGS

KQWDTFLSAE LPDWLAANRG AAQGGYGAMA LAAFHPDRFG

FAGSMSGFLY PSNTTTNGAI AAGMQQFGGV DTNGMWGAPQ

LGRWKWHDPW VHASLLAQNN TRVWVWSPTN PGASDPAAMI

GQTAEAMGNS RMFYNQYRSV GGHNGHFDFP ASGDNGWGSW

APQLGAMSGD IVGAIR

The full length nucleotide and amino acid sequences of MPT51 have been available in GenBank since 1997. (GenBank Accession number CAA05211: MPT51 *[Mycobacterium tuberculosis]* submitted 17 Oct. 1997 by T. Oettinger). The published GenBank sequence includes the full length gene so that the amino acid sequence includes a 33 residue signal sequence that is cleaved from the protein before it is secreted. Thus, the final protein product is SEQ ID NO:107 as shown.

MPT51 is reactive with mAb IT-52. This protein corresponds to the protein spot designated Ref. No. 170 in 2D gels not shown here (summarized in Table 4 and Table 6).

(4) MPT32

This glycoprotein has an apparent molecular mass (as a doublet peak) of 38 and 42 kDa (42/45 kDa according to Espitia et al. (supra)) and an isoelectric point of about pH 4.51. It is reactive with a polyclonal anti-MPT 32 antiserum. This protein is a major antigenic component of Fraction 13 (see Examples). MPT32 corresponds to the protein spot designated Ref. No. 14 in Table 4 or Table 6.

One additional protein, termed the "49 kDa protein," has an apparent molecular mass of about 49 kDa and an isoelectric point of about pH 5.1. This protein reacts with mAb IT-58 and corresponds to a spot identified as Ref. No. 82 in Table 4 or Table 6.

Mycobacterial Peptides and Functional Derivatives

The present invention also provides peptides of GlcB and of MPT51, early antigenic Mtb proteins. Such peptides are also useful as diagnostic and vaccine compositions. As shown in Examples IX, preferred peptides that were predicted and indeed shown to react with TB sera include, but are not limited to (1) CGTDGAEKGPTYNKVRGDK which corresponds to GlcB residues 151-167 (SEQ ID NO:108) with the addition of the N-terminal C-G;

(2) KIGIMDEERRTTVNLKAC which corresponds to GlcB residues 428-445 (SEQ ID NO:109);

(3) ELAWAPDEIREEVDNNC which corresponds to GlcB residues 586-603 (SEQ ID NO:110);

(4) LHRRRREFKARAAEKPAPSDRAG which corresponds to GlcB residues 715-736 (SEQ ID NO:111);

(5) ARDELQAQIDKWHRRR which corresponds to GlcB residues 56-71 (SEQ ID NO:112);

(6) LNRDRNYTAPGGGQ which corresponds to GlcB residues 314-327 (SEQ ID NO:113);

(7) GAPQLGRWKWHDPWV which corresponds to MPT51 residues 167-181 (SEQ ID NO:114);

From an analysis of overlapping 13-mer peptides with TB sera, the following 16 peptides in which the amino acids are contiguous residues of GlcB (SEQ ID NO:106), were found to include or be part of seroreactive GlcB epitopes.

| | | |
|---|---|---|
| (8) | LRIARVLYDF; | (SEQ ID NO: 117) |
| (9) | QAQIDKWHRRRVI; | (SEQ ID NO: 126) |
| (10) | WHRRRVIEPIDMD; | (SEQ ID NO: 127) |
| (11) | IEPIDMDAYRQFL; | (SEQ ID NO: 128) |
| (12) | ITTTAGPQLVVPV; | (SEQ ID NO: 134) |
| (13) | PQLVVPVLNARFA; | (SEQ ID NO: 135) |
| (14) | VLNARFALNAANA; | (SEQ ID NO: 136) |
| (15) | ALNAANARWGSLY; | (SEQ ID NO: 137) |
| (16) | ARWGSLYDALYGT; | (SEQ ID NO: 138) |
| (17) | SVLLINHGLHIEI; | (SEQ ID NO: 154) |
| (18) | HGLHIEILIDPES; | (SEQ ID NO: 155) |
| (19) | GGQFTLPGRSLMF; | (SEQ ID NO: 170) |
| (20) | FVRNVGHLMTNDA; | (SEQ ID NO: 172) |
| (21) | DRVVFINTGFLDR; | (SEQ ID NO: 191) |
| (22) and | NCQSILGYVVRWV; | (SEQ ID NO: 216) |
| (23) | GYVVRWVDQGVGC. | (SEQ ID NO: 217) |

A peptide which includes an antibody epitopes should have at least about 5 amino acids. A T cell epitope is preferably between about 10 and 15 amino acids. Thus, the present invention includes peptides having between about 5 and 30 residues, having the native sequences of the Mtb early antigenic proteins or being homologues, substitution variants, addition variants or deletion variants thereof.

When the peptide is to be administered to a subject, particularly for the vaccine embodiments of this invention, the peptide may be capped at its N and C termini with an acyl (abbreviated "Ac")- and an amido (abbreviated "Am") group, respectively, for example acetyl ($CH_3CO$—) at the N terminus and amido (—$NH_2$) at the C terminus.

A broad range of N-terminal capping functions, preferably in a linkage to the terminal amino group, is contemplated, for example: formyl; alkanoyl, having from 1 to 10 carbon atoms, such as acetyl, propionyl, butyryl; alkenoyl, having from 1 to 10 carbon atoms, such as hex-3-enoyl; alkynoyl, having from 1 to 10 carbon atoms, such as hex-5-ynoyl; aroyl, such as benzoyl or 1-naphthoyl; heteroaroyl, such as 3-pyrroyl or 4-quinoloyl; alkylsulfonyl, such as methanesulfonyl; arylsulfonyl, such as benzenesulfonyl or sulfanilyl; heteroarylsulfonyl, such as pyridine-4-sulfonyl; substituted alkanoyl, having from 1 to 10 carbon atoms, such as 4-aminobutyryl; substituted alkenoyl, having from 1 to 10 carbon atoms, such as 6-hydroxy-hex-3-enoyl; substituted alkynoyl, having from 1 to 10 carbon atoms, such as 3-hydroxy-hex-5-ynoyl; substituted aroyl, such as 4-chlorobenzoyl or 8-hydroxy-naphth-2-oyl; substituted heteroaroyl, such as 2,4-dioxo-1,2,3,4-tetrahydro-3-methyl-quinazolin-6-oyl; substituted alkylsulfonyl, such as 2-aminoethanesulfonyl; substituted arylsulfonyl, such as 5-dimethylamino-1-naphthalenesulfonyl; substituted heteroarylsulfonyl, such as 1-methoxy-6-isoquinolinesulfonyl; carbamoyl or thiocarbamoyl; substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl; substituted carbamoyl (R'—NH—CO) and substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined.

The C-terminal capping function can either be in an amide or ester bond with the terminal carboxyl. Capping functions that provide for an amide bond are designated as $NR^1R^2$ wherein $R^1$ and $R^2$ may be independently drawn from the following group: hydrogen; alkyl, preferably having from 1 to 10 carbon atoms, such as methyl, ethyl, isopropyl; alkenyl, preferably having from 1 to 10 carbon atoms, such as prop-2-enyl; alkynyl, preferably having from 1 to 10 carbon atoms, such as prop-2-ynyl; substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl; substituted alkenyl having from 1 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl; substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl; aroylalkyl having up to 10 carbon atoms, such as phenacyl or 2-benzoylethyl; aryl, such as phenyl or 1-naphthyl; heteroaryl, such as 4-quinolyl; alkanoyl having from 1 to 10 carbon atoms, such as acetyl or butyryl; aroyl, such as benzoyl; heteroaroyl, such as 3-quinoloyl; OR' or NR'R" where R' and R" are independently hydrogen, alkyl, aryl, heteroaryl, acyl, aroyl, sulfonyl, sulfinyl, or $SO_2$—R'" or SO—R'" where R'" is substituted or unsubstituted alkyl, aryl, heteroaryl, alkenyl, or alkynyl.

Capping functions that provide for an ester bond are designated as OR, wherein R may be: alkoxy; aryloxy; heteroaryloxy; aralkyloxy; heteroaralkyloxy; substituted alkoxy; substituted aryloxy; substituted heteroaryloxy; substituted aralkyloxy; or substituted heteroaralkyloxy.

Judicious choice of capping groups allows the addition of other activities on the peptide. For example, the presence of a sulfhydryl group linked to the N- or C-terminal cap will permit conjugation of the derivatized peptide to other molecules.

Production of Peptides and Derivatives

General Chemical Synthetic Procedures

The peptides of the invention may be prepared using recombinant DNA technology. However, some of the shorter peptides may be prepared using solid-phase synthesis, such as that generally described by Merrifield, *J. Amer. Chem. Soc.*, 85:2149-54 (1963), although other equivalent chemical syntheses known in the art are also useful. Solid-phase peptide synthesis may be initiated from the C-terminus of the peptide by coupling a protected $\alpha$-amino acid to a suitable resin. Such a starting material can be prepared by attaching an $\alpha$-amino-protected amino acid by an ester linkage to a chloromethylated resin or to a hydroxymethyl resin, or by an amide bond to a BHA resin or MBHA resin. Such methods, well-known in the art, are disclosed, for example, in U.S. Pat. No. 5,994,309 (issued Nov. 30, 1999) which is incorporated by reference in its entirety.

Amino Acid Substitution and Addition Variants

Also included in this invention are peptides in which at least one amino acid residue and preferably, only one, has been removed and a different residue inserted in its place compared to the native Mtb sequence. For a detailed description of protein chemistry and structure, see Schulz, G. E. et al., *Principles of Protein Structure*, Springer-Verlag, New York, 1979, and Creighton, T. E., *Proteins: Structure and Molecular Principles*, W.H. Freeman & Co., San Francisco, 1984, which are hereby incorporated by reference. The types of substitutions which may be made in the peptide molecule of the present invention are conservative substitutions, which are typically exchanges within one of the following groups:

1. Small aliphatic, nonpolar or slightly polar residues: e.g., Ala, Ser, Thr, Gly;
2. Polar, negatively charged residues and their amides: e.g., Asp, Asn, Glu, Gln;
3. Polar, positively charged residues: e.g., His, Arg, Lys;

Pro, because of its unusual geometry, tightly constrains the chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Preferred substitutions according to the present invention are those that do not produce radical changes in the characteristics of the peptide molecule. Even when it is difficult to predict the exact effect of a substitution in advance of doing so, one skilled in the art will appreciate that the effect can be evaluated by routine screening assays, preferably biological assays described herein, preferably serological assays using antisera, antisera pools, or monoclonal antibodies. Modifications of peptide properties including redox or thermal stability, hydrophobicity, susceptibility to proteolytic degradation or the tendency to aggregate with carriers (or into multimers) are assayed by methods well known to the ordinarily skilled artisan.

Addition variants of the present Mtb peptides preferably include from 1-4 amino acids, but may include as many as X amino acids, added either at the N-terminus, the C-termins or both. Amino acids that are added to the basic peptide unit are onres that permit the peptide to maintain its biological reactivity in accordance with this invention, namely antigenicity (recognition by antibodies or T lymphocytes) or immunogenicity in the case of vaccine embodiments.

For use as vaccine peptides, preferred variants are those that have increased stability and/or immunogenicity. Conventional approaches of protein engineering are applied. In one embodiment, stability is increased by introducing one or more Cys residues into strategic positions, where the formation of disulfide bonds between two Cys residues increases stability. Another approach is based on introduction of residues that form α helices at sites that do not impede the peptide immunologic activity, for example at the N- and C-termini.

In a peptide or polypeptide having a total of n residues, as many as (n−5) amino acids may be substituted, provided that the characteristic immunoreactivity with early Mtb antibodies is not lost.

Chemical derivatives of the peptides are also included. Lysinyl and amino terminal residues may be derivatized with succinic or other carboxylic acid anhydrides. Derivatization with a cyclic carboxylic anhydride has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups, aspartyl or glutamyl, may be selectively modified by reaction with carbodiimides (R—N═C═N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra, pp. 79-86), acetylation of the N-terminal amine, and amidation of the C-terminal carboxyl groups.

Multimeric Peptides and Fusion Proteins (Polyproteins)

The present invention also includes longer peptides or polypeptides in which a sequence of an Mtb early antigenic peptide or a substitution or addition variant thereof, or a chemical derivative thereof, is repeated from two to about 100 times, with or without intervening spacers or linkers. Such molecules are termed in the art, interchangeably, multimers, concatemers or multiepitope polyproteins and will be referred to herein primarily as peptide multimers. When produced recombinantly, they are also considered to be fusion polypeptides or fusion proteins.

A multimer of the peptide referred to symbolically in this section as "P" is shown by the following formula $(P—X_m)_n—P$ wherein m=0 or 1, n=1-100. X is a spacer group, consisting of 1-20 glycine residues or chemical cross-linking agents. Thus, when m=0, no spacer is added to the peptide. When n=1, the multimer is a dimer, etc.

These multimers may be built from any of the antigenic peptides or variants described herein. Moreover, a peptide multimer may comprise different combinations of peptide monomers (either from the native sequence or variants thereof). Thus a multimer may include several sequential repeats of a first peptide, followed by one or more repeats of a second peptide, etc. Such multimeric peptides can be made by chemical synthesis of individual peptides, recombinant DNA techniques or a combination, e.g., chemical linkage of recombinantly produced multimers.

When produced by chemical synthesis, the multimers preferably have from 2-12 repeats, more preferably 2-8 repeats of the core peptide sequence, and the total number of amino acids in the multimer should not exceed about 110 residues (or their equivalents, when including linkers or spacers).

A preferred synthetic chemical peptide multimer has the formula $$P^1_n$$

wherein $P^1$ is a native Mtb peptide or a substitution or addition variant of such a peptide, and n=2-8, and wherein the peptide alone or in multimeric form has the desired immunologic reactivity.

In another embodiment, a preferred synthetic chemical peptide multimer has the formula $$(P^1—X_m)_n—P^2$$

$P^1$ and $P^2$ are Mtb peptides or addition variants of these peptides, wherein (a) $P^1$ and $P^2$ may be the same or different; moreover, each occurrence of $P^1$ in the multimer may be a different peptide (or variant) from its adjacent neighbor;

(b) X is $C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1 and n=1-7; X may also be $Gly_z$ wherein, z=1-6, and wherein the peptide alone or in multimeric form has the immunological activity of reacting with anti-Mtb antibodies, preferably early antibodies.

When produced recombinantly, spacers are $Gly_z$ as described above, where z=1-6, and the multimers may have as many repeats of the core peptide sequence as the expression system permits, for example from two to about 100 repeats. A preferred recombinantly produced peptide multimer has the formula:

$$P^1\text{-}Gly_z)_n\text{-}P^2$$

wherein:

(a) $P^1$ and $P^2$ are Mtb peptides as described herein or substitution or addition variants of these peptides, wherein $P^1$ and $P^2$ may be the same or different; moreover, each occurrence of $P^1$ in the multimer may be different peptide (or variant) from its adjacent neighbor.

wherein n=1-100 and z=0-6;

and wherein the peptide alone or in multimeric form has the desired immunologic reactivity.

In the foregoing peptide multimers, $P^1$ and $P^2$ is preferably selected from any one of the followings SEQ ID NO's: 108-114; 117; 126-128, 134-138, 154, 155, 170, 172, 191, 216, and 217.

The multimer is optionally capped at its N- and C-termini,

It is understood that such multimers may be built from any of the peptides or variants described herein. Although it is preferred that the addition variant monomeric units of the multimer have the biological activity described above, that is not necessary as long as the multimer to which they contribute has the activity.

The present invention includes as fusion polypeptide which may comprise a linear multimer of two or more repeats of the above peptide monomers linked end to end, directly or with a linker sequences present between the monomer repeats and further fused to another polypeptide sequence which permits or enhances the activity of the antigenic peptides in accordance with this invention.

The present multimers and fusion polypeptides may therefore include more than one epitope from the same or different Mtb proteins that do not occur together, i.e., in a contiguous structure, in a native Mtb protein.

Also included herein are polyproteins or fusion proteins which combine longer polypeptides, even full length Mtb proteins such as GlcB, MPT51 and other Mtb early antigens described herein in various combinations, such as a fusion of GlcB and MPT51 or these two with another one or more early antigenic protein. These full length proteins may be combined in polyproteins with shorter epitope-bearing Mtb peptides or variants thereof or with peptide multimers (homo- or hetero-multimers). Such fusion proteins optionally includes spacers or linkers between some or all of the individual protein or peptide units.

Peptides and multimers may be chemically conjugated to form multimers and larger aggregates. Preferred conjugated multimers include Cys and are made by forming disulfide bonds between the —SH groups of these residues, resulting in branched chains as well as straight chain peptides or polypeptides.

In addition to the linkers described above, the present multimers and fusion polypeptides may include linkers that are cleavable by an enzyme. Preferred enzymes are a matrix metalloprotease, urokinase, a cathepsin, plasmin or thrombin. A preferred linker is a peptide having the sequence VPRGSD (SEQ ID NO:115) or DDKDWH (SEQ ID NO:238).

These peptides may be combined in the form of fusion polypeptides that comprise one or more repeats of a single peptide or mixtures of such peptides fused to other proteins, e.g., carrier molecules or other proteins which would enhance their immunogenicity when used as vaccine compositions.

Additional compositions within the scope of this invention are the foregoing peptides, multimers or fusion polypeptides immobilized to a solid support or carrier for use in immunoassays. By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, polyvinylidene difluoride, agaroses such as Sepharose®, and magnetic beads. The support material may have virtually any possible structural configuration so long as the immobilized peptide or polypeptide is capable of binding to its target molecule, e.g., antibody. Thus, the support configuration can include microparticles, beads, porous and impermeable strips and membranes, the interior surface of a reaction vessel such as a test tube or a microtiter plate, the external surface of a rod, and the like. Those skilled in the art will know many other suitable carriers for binding the peptides or will be able to ascertain these by routine experimentation.

The kits of the present invention described in more detail below may include one or more of the various peptide compositions described herein.

Immunoassays

In a preferred embodiment, the mycobacterial antigen composition is brought in contact with, and allowed to bind to, a solid support or carrier, such as nitrocellulose or polystyrene, allowing the antigen composition to adsorb and become immobilized to the solid support. This immobilized antigen is then allowed to interact with the biological fluid sample which is being tested for the presence of anti-Mtb antibodies, such that any antibodies in the sample will bind to the immobilized antigen. The support to which the antibody is now bound may then be washed with suitable buffers after which a detectably labeled binding partner for the antibody is introduced. The binding partner binds to the immobilized antibody. Detection of the label is a measure of the immobilized antibody.

A preferred binding partner for this assay is an anti-immunoglobulin antibody ("second antibody") produced in a different species. Thus to detect a human antibody, a detectably labeled goat anti-human immunoglobulin "second" antibody may be used. The solid phase support may then be washed with the buffer a second time to remove unbound antibody. The amount of bound label on the solid support may then be detected by conventional means appropriate to the type of label used (see below).

Such a "second antibody" may be specific for epitopes characteristic of a particular human immunoglobulin isotype, for example IgM, $IgG_1$, $IgG_{2a}$, IgA and the like, thus permitting identification of the isotype or isotypes of antibodies in the sample which are specific for the mycobacterial antigen. Alternatively, the second antibody may be specific for an idiotype of the ant-Mtb antibody of the sample.

As alternative binding partners for detection of the sample antibody, other known binding partners for human immunoglobulins may be used. Examples are the staphylococcal immunoglobulin binding proteins, the best know of which is protein A. Also intended is staphylococcal protein G, or a recombinant fusion protein between protein A and protein G. Protein G (of group G and group C streptococci) binds to the Fc portion of Ig molecules as well as to IgG Fab fragment at the $V_H3$ domain. Protein C of *Peptococcus magnus* binds to the Fab region of the immunoglobulin molecule. Any other microbial immunoglobulin binding proteins, for example from Streptococci, are also intended (for example, Langone, J. J., *Adv. Immunol.* 32:157 (1982)).

In another embodiment of this invention, a biological fluid suspected of containing antibodies specific for a Mtb antigen may be brought into contact with a solid support or carrier which is capable of immobilizing soluble proteins. The support may then be washed with suitable buffers followed by treatment with a mycobacterial antigen reagent, which may be detectably labeled. Bound antigen is then measured by measuring the immobilized detectable label. If the mycobacterial antigen reagent is not directly detectably labeled, a second reagent comprising a detectably labeled binding partner for the Mtb antigen, generally a second anti-Mtb antibody such as a murine mAb, is allowed to bind to any immobilized antigen. The solid phase support may then be washed with buffer a second time to remove unbound antibody. The amount of bound label on said solid support may then be detected by conventional means.

By "solid phase support" is intended any support capable of binding a proteinaceous antigen or antibody molecules or other binding partners according to the present invention. Well-known supports, or carriers, include glass, polystyrene, polypropylene, polyethylene, polyvinylidene difluoride, dextran, nylon, magnetic beads, amylases, natural and modified celluloses, polyacrylamides, agaroses, and magnetite. The nature of the carrier can be either soluble to some extent or insoluble for the purposes of the present invention. The support material may have virtually any possible structural configuration so long as it is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads, 96-well polystyrene microplates and test strips, all well-known in the art. Those skilled in the art will know many other suitable carriers for binding antibody or antigen, or will be able to ascertain the same by use of routine experimentation.

Using any of the assays described herein, those skilled in the art will be able to determine operative and optimal assay conditions for each determination by employing routine experimentation. Furthermore, other steps as washing, stirring, shaking, filtering and the like may be added to the assays as is customary or necessary for the particular situation.

A preferred type of immunoassay to detect an antibody specific for a mycobacterial antigen according to the present invention is an enzyme-linked immunosorbent assay (ELISA) or more generically termed an enzyme immunoassay (EIA). In such assays, a detectable label bound to either an antibody-binding or antigen-binding reagent is an enzyme. When exposed to its substrate, this enzyme will react in such a manner as to produce a chemical moiety which can be detected, for example, by spectrophotometric, fluorometric or visual means. Enzymes which can be used to detectably label the reagents useful in the present invention include, but are not limited to, horseradish peroxidase, alkaline phosphatase, glucose oxidase, β-galactosidase, ribonuclease, urease, catalase, malate dehydrogenase, staphylococcal nuclease, asparaginase, Δ-5-steroid isomerase, yeast alcohol dehydrogenase, α-glycerophosphate dehydrogenase, triose phosphate isomerase, glucose-6-phosphate dehydrogenase, glucoamylase and acetylcholinesterase. For descriptions of EIA procedures, see Voller, A. et al., J. Clin. Pathol. 31:507-520 (1978); Butler, J. E., *Meth. Enzymol.* 73:482-523 (1981); Maggio, E. (ed.), *Enzyme Immunoassay*, CRC Press, Boca Raton, 1980; Butler, J. E., In: *Structure of Antigens*, Vol. 1 (Van Regenmortel, M., CRC Press, Boca Raton, 1992, pp. 209-259; Butler, J. E., In: van Oss, C. J. et al., (eds), *Immunochemistry*, Marcel Dekker, Inc., New York, 1994, pp. 759-803; Butler, J. E. (ed.), *Immunochemistry of Solid-Phase Immunoassay*, CRC Press, Boca Raton, 1991)

In another embodiment, the detectable label may be a radiolabel, and the assay termed a radioimmunoassay (RIA), as is well known in the art. See, for example, Yalow, R. et al., Nature 184:1648 (1959); Work, T. S., et al., *Laboratory Techniques and Biochemistry in Molecular Biology*, North Holland Publishing Company, NY, 1978, incorporated by reference herein. The radioisotope can be detected by a gamma counter, a scintillation counter or by autoradiography. Isotopes which are particularly useful for the purpose of the present invention are $^{125}$I, $^{131}$I, $^{35}$S, $^{3}$H and $^{14}$C.

It is also possible to label the antigen or antibody reagents with a fluorophore. When the fluorescently labeled antibody is exposed to light of the proper wave length, its presence can then be detected due to fluorescence of the fluorophore. Among the most commonly used fluorophores are fluorescein isothiocyanate, rhodamine, phycoerythrin, phycocyanin, allophycocyanin, o-phthal-dehyde, fluorescamine or fluorescence-emitting metals such as $^{152}$Eu or other lanthanides. These metals are attached to antibodies using metal chelators.

The antigen or antibody reagents useful in the present invention also can be detectably labeled by coupling to a chemiluminescent compound. The presence of a chemiluminescent-tagged antibody or antigen is then determined by detecting the luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound such as a bioluminescent protein may be used to label the antigen or antibody reagent useful in the present invention. Binding is measured by detecting the luminescence. Useful bioluminescent compounds include luciferin, luciferase and aequorin.

Detection of the detectably labeled reagent according to the present invention may be accomplished by a scintillation counter, for example, if the detectable label is a radioactive gamma emitter, or by a fluorometer, for example, if the label is a fluorophore. In the case of an enzyme label, the detection is accomplished by colorimetry to measure the colored product produced by conversion of a chromogenic substrate by the enzyme. Detection may also be accomplished by visual comparison of the colored product of the enzymatic reaction in comparison with appropriate standards or controls.

The immunoassay of this invention may be a "two-site" or "sandwich" assay. The fluid containing the antibody being assayed is allowed to contact a solid support. After addition of the mycobacterial antigen(s), a quantity of detectably labeled soluble antibody is added to permit detection and/or quantitation of the ternary complex formed between solid-phase antibody, antigen, and labeled antibody. Sandwich assays are described by Wide, *Radioimmune Assay Method*, Kirkham et al., Eds., E. & S. Livingstone, Edinburgh, 1970, pp 199-206.

Alternatives to the RIA and EIA are various types of agglutination assays, both direct and indirect, which are well known in the art. In these assays, the agglutination of particles containing the antigen (either naturally or by chemical coupling) indicates the presence or absence of the corresponding antibody. Any of a variety of particles, including latex, charcoal, kaolinite, or bentonite, as well as microbial cells or red blood cells, may be used as agglutinable carriers (Mochida, U.S. Pat. No. 4,308,026; Gupta et al., J. Immunol. Meth. 80:177-187 (1985); Castelan et al., J. Clin. Pathol. 21:638 (1968); Singer et al., Amer. J. Med. (December 1956, 888; Molinaro, U.S. Pat. No. 4,130,634). Traditional particle agglutination or hemagglutination assays are generally faster, but much less sensitive than RIA or EIA. However, agglutination assays have advantages under field conditions and in less developed countries.

In addition to detection of antibodies, the present invention provides methods to detect and enumerate cells secreting an antibody specific for a mycobacterial antigen. Thus, for example, any of a number of plaque or spot assays may be used wherein a sample containing lymphocytes, such as peripheral blood lymphocytes, is mixed with a reagent containing the antigen of interest. As the antibody secreting cells of the sample secrete their antibodies, the antibodies react with the antigen, and the reaction is visualized in such a way that the number of antibody secreting cells (or plaque forming cells) may be determined. The antigen may be coupled to indicator particles, such as erythrocytes, preferably sheep erythrocytes, arranged in a layer. As antibodies are secreted from a single cell, they attach to the surrounding antigen-bearing erythrocytes. By adding complement components, lysis of the erythrocytes to which the antibodies have attached is achieved, resulting in a "hole" or "plaque" in the erythrocyte layer. Each plaque corresponds to a single antibody-secreting cell. In a different embodiment, the sample containing antibody-secreting cells is added to a surface coated with an antigen-bearing reagent, for example, a mycobacterial antigen alone or conjugated to bovine serum albumin, attached to polystyrene. After the cells are allowed to secrete the antibody which binds to the immobilized antigen, the cells are gently washed away. The presence of a colored "spot" of bound antibody, surrounding the site where the cell had been, can be revealed using modified EIA or other staining methods well-known in the art. (See, for example, Sedgwick, J D et al., *J. Immunol. Meth.* 57:301-309 (1983); Czerkinsky, C C et al., *J. Immunol. Meth.* 65:109-121 (1983); Logtenberg, T. et al., Immunol. Lett. 9:343-347 (1985); Walker, A. G. et al., J. Immunol. Meth. 104:281-283 (1987).

The present invention is also directed to a kit or reagent system useful for practicing the methods described herein. Such a kit will contain a reagent combination comprising the essential elements required to conduct an assay according to the disclosed methods. The reagent system is presented in a commercially packaged form, as a composition or admixture (where the compatibility of the reagents allow), in a test device configuration, or more typically as a test kit. A test kit is a packaged combination of one or more containers, devices, or the like holding the necessary reagents, and usually including written instructions for the performance of assays. The kit may include containers to hold the materials during storage, use or both. The kit of the present invention may include any configurations and compositions for performing the various assay formats described herein.

For example, a kit for determining the presence of anti-Mtb early antibodies may contain one or more early Mtb antigens, either in immobilizable form or already immobilized to a solid support, and a detectably labeled binding partner capable of recognizing the sample anti-Mtb early antibody to be detected, for example. a labeled anti-human Ig or anti-human Fab antibody. A kit for determining the presence of an early Mtb antigen may contain an immobilizable or immobilized "capture" antibody which reacts with one epitope of an early Mtb antigen, and a detectably labeled second ("detection") antibody which reacts with a different epitope of the Mtb antigen than that recognized by the (capture) antibody. Any conventional tag or detectable label may be part of the kit, such as a radioisotope, an enzyme, a chromophore or a fluorophore. The kit may also contain a reagent capable of precipitating immune complexes.

A kit according to the present invention can additionally include ancillary chemicals such as the buffers and components of the solution in which binding of antigen and antibody takes place.

The present invention also provides an approach to the identification, isolation and characterization of early Mtb antigens. For example, an adsorbed patient serum or pool of sera containing antibody for one or more antigens can be used in initial stages of antigen preparation and purification, as well as in the process of cloning of a protein antigen. This antiserum can be further adsorbed with an Mtb or other mycobacterial preparation to render it functionally monospecific or oligospecific. This "enriched" antiserum can be used along with standard biochemical purification techniques to assay for the presence of the antigen it recognizes in fractions obtained during the purification process. The antiserum can also be used in immobilized form as an immunoadsorbent in affinity purification of the antigen in accordance with standard methods in the art. In addition, the antiserum can be used in an expression cloning method to detect the presence of the antigen in bacterial colonies or phage plaques where the antigen is expressed.

Once an antigen has been purified, for example by using patient early antibodies that have been determined to be specific fore the subject antigen, the antigen can be used to immunize animals to prepare high titer antisera or, preferably, to obtain a mAb specific for that antigen. Such an animal antiserum or mAb can be employed advantageously in place of the patient antiserum or in combination with a test body fluid sample in a competition immunoassay. Thus, the antiserum or mAb can be used for antigen production or purification, or in an immunoassay for detecting the antigen, for example as a binding partner (either the capture antibody or the detection antibody) in a sandwich immunoassay.

The present invention provides an immunoassay for detecting the presence of an Mtb early antigen in a body fluid or in a bacterial culture grown from a body fluid of a subject suspected of being infected with Mtb. A sensitive immunoassay, such as a direct sandwich EIA or a competitive EIA can detect an Mtb protein (early antigen) in picogram amounts. A competitive assay allows detection of specific epitopes of the Mtb antigen without the necessity of starting with a purified antigen preparation. Such assays permits detection of Mtb in the patient sample at an earlier time than standard bacteriological analysis (i.e., appearance of colonies on agar). This method therefore provides a basis for clinical decisions to initiate therapy after several hours or days if the antigen can be detected in a body fluid. In any case, this is a major advantage over the conventional two to four (or more) weeks commonly needed to grow out Mtb organisms from a patient sample. The earlier the stage of the infection, the lower would be the titer of Mtb in a given body fluid, and the greater would be the advantage of the present assay over conventional diagnosis. A number of immunoassays for various Mtb antigens are known in the art and can serve as the basis for development of assays for the early antigens of the present invention (Wilkins et al., supra; Verbon, 1994, supra; Benjamin, R G et al., 1984, *J. Med. Micro.* 18:309-318; Yanez, M A et al., 1986, *J. Clin. Microbiol.* 23:822-825; Ma et al., supra; Daniel et al., 1986, 1987, supra; Watt, G et al., 1988, *J. Infec. Dis.* 158:681-686; Wadee, A A et al., 1990, *J. Clin. Microbiol.* 23:2786-2791). For an example of a competition EIA for a Mtb antigen, see Jackett et al., supra).

In a preferred sandwich immunoassay, a human antisera (or pool) or a mAb, preferably murine, serving as the capture antibody, is immobilized to a solid phase, preferably a microplate. The test antigen preparation, for example an Mtb culture supernatant or extract is added to the immobilized antibody. After appropriate washing, a second "detection" antibody, such as a murine mAb specific for the same antigen or preferably for a different epitope of the same protein, allowed to bind in the presence of a fixed amount of a mAb, preferably of murine origin, specific for the epitope of interest. The detection mAb may be enzyme-conjugated. Alternatively, a second step reagent such as an enzyme-labeled antibody specific for murine immunoglobulin may be used for detection of antigen which has become immobilized.

The present invention permits isolation of an Mtb early antigen which is then used to produce one or more epitope-specific mAbs, preferably in mice. Screening of these putative early Mtb-specific mAbs is done using known patient sera which have been characterized for their reactivity with the early antigen of interest. The murine mAbs produced in this way are then employed in a highly sensitive epitope-specific competition immunoassay for early detection of TB. Thus, a patient sample is tested for the presence of antibody specific for an early epitope of Mtb by its ability to compete with a known mAb for binding to a purified early antigen. For such an assay, the mycobacterial preparation may be less than pure because, under the competitive assay conditions, the mAb provides the requisite specificity for detection of patient antibodies to the epitope of choice (for which the mAb is specific).

In addition to the detection of early Mtb antigens or early antibodies, the present invention provides a method to detect immune complexes containing early Mtb antigens in a subject using an EIA as described above. Circulating immune complexes have been suggested to be of diagnostic value in TB. (See, for example, Mehta, P K et al, 1989, *Med. Microbiol. Immunol.* 178:229-233; Radhakrishnan, V V et al., 1992, *J. Med. Microbiol.* 36:128-131). Methods for detection of immune complexes are well-known in the art. Complexes may be dissociated under acid conditions and the resultant antigens and antibodies detected by immunoassay. See, for example, Bollinger, R C et al, 1992, *J Infec. Dis.* 165:913-916. Immune complexes may be precipitated for direct analysis or for dissociation using known methods such as polyethylene glycol precipitation.

Purified Mtb early antigens as described herein are preferably produced using recombinant methods. See Example IV. Conventional bacterial expression systems utilize Gram negative bacteria such as *E. coli* or *Salmonella* species. However, it is believed that such systems are not ideally suited for production of Mtb antigens (Burlein, J E, In: *Tuberculosis: Pathogenesis, Protection and Control*, B. Bloom, ed., Amer Soc Microbiol, Washington, D.C., 1994, pp. 239-252). Rather, it is preferred to utilize homologous mycobacterial hosts for recombinant production of early Mtb antigenic proteins or glycoproteins. Methods for such manipulation and gene expression are provided in Burlein, supra. Expression in mycobacterial hosts, in particular *M. bovis* (strain BCG) or *M. smegmatis* are well-known in the art. Two examples, one of mycobacterial genes (Rouse, D A et al., 1996, *Mol. Microbiol.* 22:583-592) and the other of non mycobacterial genes, such as HIV-1 genes (Winter, N et al., 1992, *Vaccines 92*, Cold Spring Harbor Press, pp. 373-378) expressed in mycobacterial hosts are cited herein as an example of the state of the art. The foregoing three references are hereby incorporated by reference in their entirety.

Urine-Based Antibody Assay

The present invention also provides a urine based diagnostic method for TB that can be used either as a stand-alone test, or as an adjunct to the serodiagnostic methods described herein. Such a method enables the practitioner to (1) determine the presence of anti-mycobacterial antibodies in urine from TB patients with early disease (non-cavitary, smear negative TB patients) and from HIV-infected TB patients; (2) determine the profile of specific mycobacterial antigens, such as those in the culture filtrate, that are consistently and strongly reactive with the urine antibodies; and (3) obtain the antigens that are recognized by the urine antibodies.

Smear positive (=late) cases constitute only about 50% of the TB cases, and patients with relatively early disease are generally defined as being smear negative. Moreover, as the HIV-epidemic spreads in developing countries, the numbers and proportions of HIV-infected TB patients increases.

Serum and urine samples from non-cavitary and/or smear negative, culture positive TB patients and from HIV-infected TB patients are obtained Cohorts comprising PPD-positive and PPD-negative healthy individuals, non-tuberculous HIV-infected individuals, or close contacts of TB patients can serve as negative controls.

The reactivity of the serum samples with culture filtrate proteins of *M. tuberculosis*, and the purified antigens (MPT 32, Ag 85C and the 88 kDa, as described herein) is preferably determined by ELISA as described herein. All sera are preferably depleted of cross-reactive antibodies prior to use in ELISA.

The following description is of a preferred assay method and approach, and is not intended to be limiting to the particular steps (or their sequence), conditions, reagents and amounts of materials.

Briefly, 200 µl of *E. coli* lysates (suspended at 500 µg/ml) are coated onto wells of ELISA plates (Immulon 2, Dynex, Chantilly, Va.) and the wells are blocked with 5% bovine serum albumin (BSA). The serum samples (diluted 1:10 in PBS-Tween-20) are exposed to 8 cycles of absorption against the *E. coli* lysates. The adsorbed sera are then used in the ELISA assays.

Fifty µl of the individual antigens, suspended at 2 µg/ml in coating buffer (except for the total culture filtrate proteins which is used at 5 µg/ml), are allowed to bind overnight to wells of ELISA plates. After 3 washes with PBS (phosphate buffered saline), the wells are blocked with 7.5% FBS (fetal bovine serum, Hyclone, Logan, Utah) and 2.5% BSA in PBS for 2.5 hr at 37° C. Fifty ul of each serum sample are added per well at predetermined optimal dilutions (1:1000 for the culture filtrate proteins, 1:50 for Ag 85C, 1:150 for the MPT32, and 1:200 for the 88 kDa antigen). The antigen-antibody binding is allowed to proceed for 90 min at 37° C. The plates are washed 6 times with PBS-Tween 20 (0.05%) and 50 µl/well of alkaline phosphatase-conjugated goat anti-human IgG (Zymed, Calif.), diluted 1:2000 in PBS/Tween 20 is added. After 60 min the plates are washed 6 times with Tris buffered saline (50 mM Tris, 150 mM NaCl) and the Gibco BRL Amplification System (Life Technologies, Gaithersburg, Md.) used for development of color. The absorbance is read at 490 nm after stopping the reaction with 50 µl of 0.3M $H_2SO_4$. The cutoff in all ELISA assays is determined by using mean absorbance (=Optical Density O.D.)+3 standard deviations (SD) of the negative control group comprising PPD positive and PPD negative healthy individuals.

The reactivity of the urine samples with the various antigens is determined initially with undiluted urine samples as described above. For the urine ELISA, results obtained by the present inventors (see Example VII) showed that the optimal concentration of the culture filtrate protein preparation is 125 µl/well of 4 µg/ml suspension, and for MPT 32 is 125 µl/well of 2 µg/ml. Also, the urine is left overnight in the antigen coated wells. However, if urine antibody titers of smear-negative and HIV-infected patients are lower than those observed in smear positive patients, it may be necessary to first concentrate the urine samples. For concentration, Amicon concentrators with a molecular weight cut off of 30 kDa is preferred. Concentrated urine samples are evaluated for the presence of antibodies to the above mentioned antigens. Optimal conditions for these assays are determined readily. The sensitivity and specificity of antibody detection by use of one or more of the antigens, with both urine and serum samples is also readily determined.

Investigations described in Example VII, with the ELISA and ID SDS-PAGE fractionated culture filtrate proteins suggested that the urine antibodies are directed against the same antigens that are recognized by the serum antibodies, although, the urine antibody titers are lower. A 2D map of the culture filtrate proteins has been prepared on which several proteins have been identified on the basis of their reactivity with different anti-mycobacterial monoclonal antibodies, or peptide sequencing (as described herein; see also Sonnenberg, M. G. et al., 1997, *Infect. Immun.* 65:4515)

Based on this map, the present inventors generated a 2-D map of the antigens that are recognized by the early serum antibodies (from smear-negative patients), antibodies from advanced, smear-positive HIV-uninfected TB patients, and from HIV-infected TB patients (described in the Examples). Screening permits the determination of whether additional antigens besides the MPT 32, Ag 85C and the 88 kDa protein are to be included in the assay for its optimization. It is preferred to determine if the anti-MPT 51 antibodies are well represented in the urine since this protein is highly recognized by serum antibodies during both early and late stages of TB, and its identity and sequence are known.

Culture filtrate antigens of Mtb are fractionated on 2-D gels and transferred to obtain 2-D blots as described below. Briefly, 70 μg of culture filtrate proteins are resuspended in 30 μl of isoelectric focusing sample buffer (e.g., 9M urea, 2% NP-40, 5% β-mercaptoethanol, and 5% ampholytes at pH 3-10 or pH 4-6.5). The ampholytes used in the Examples below from Pharmacia, are designated "Pharmalytes™" and are co-polymers of glycine, glycylglycine, amines and epichlorhydrin. Two different Pharmalytes™ with different pH ranges were used in the isoelectric focusing step of the 2-D gel analysis (pH 3-10 and pH 4-6.5) of the Examples. (As used in the Example, the Pharmacia catalog numbers for these two osmolytes were 17-0456-01 and 17-0452-01, respectively.) The above samples are incubated for 3 hrs at 20° C. A 25 μl aliquot of this preparation is applied to a 6% polyacrylamide IEF tube gel containing 5% ampholytes pH 3-10 and pH 4-6.5 at a 1:4 ratio and focused for 3 hrs at 1kV. After focusing, the tube gels are soaked in sample transfer buffer for 30 min and then electrophoresed in the second dimension by using a 15% SDS-polyacrylamide gel. This is carried out at 20 mA per gel for 0.3 hrs followed by 30 mA per gel for 1.8 hrs. The separated proteins are then transferred for subsequent immunoblotting. The 2-D western blots are washed with PBS, and blocked for 2-2.5 hr. with 5% BSA. After washing the blots again, they are exposed to the individual urine samples (undiluted, or concentrated) overnight with shaking. After subsequent washing with PBS-Tween, the blots are exposed to alkaline-phosphatase conjugated anti-human IgG, and then to the appropriate substrate. The antigens that are reactive with the urine samples are identified on the basis of the 2-D maps already generated. The antigens that are recognized by urine antibodies from smear negative, non-cavitary (=early) TB patients, smear positive (=late) TB patients, as well as HIV-infected TB patients are thus delineated.

Antigens that are strongly recognized by the urine antibodies, as well as by serum antibodies, are candidates for inclusion in the preferred diagnostic assay. Preferred antigens are the 88 kDa protein GlcB described above or is MPT 51 and epitopes thereof, such those present in the various peptides described above. DNA encoding these proteins or fragments or variants thereof are cloned and expressed.

As described herein, the Mtb culture filtrate preparation contains >100 different proteins (205 protein spots), and most of the proteins in the 49-76 kDa range are expressed in low abundance in the culture medium (Sonnenberg et al., supra). This may be a result of growing Mtb is in minimal medium to obtain these proteins, to avoid difficulties associated with the proteins of enriched media (BSA, casein digests, etc.). If the immunoreactive protein is well-expressed in the culture filtrate, and reasonably isolated on the gel, it can be excised from the PVDF blot and sequenced. Since the entire genomic sequence of Mtb is known, the peptide sequence is used to identify the protein with complete precision.

The nucleotide sequence of the gene (i.e., open reading frame) encoding that protein then becomes the basis for PCR amplification of the relevant DNA from genomic DNA, followed by cloning into an expression vector. Since many of the culture filtrate proteins are present in small quantities, an alternative, possibly more reliable, approach would utilize the urine antibodies to immunoscreen an expression library of Mtbs to obtain the gene(s) encoding the relevant protein(s).

These approaches may be used, for example, to clone the MPT 51 gene or to identify the immunoreactive proteins in the 49-76 kDa region. For expression of MPT 51, the shuttle vector pVV16 is preferred; this vector has an $E.$ $coli$ origin of replication, the mycobacterial pAL5000 origin of replication, a gene for hygromycin resistance and the hsp60 promoter. It has been modified to encode six His residues at the C terminus. This vector can be used for expression in $E.$ $coli$ or in $M.$ $smegmatis$. Since mycobacterial proteins expressed in $E.$ $coli$ host often show poorer immunological reactivity than the same proteins expressed in the mycobacterial host, it would be preferred to express the antigen in $M.$ $smegmatis$. The methods for expression of genes in mycobacterial hosts are well described (Gaora, P O et al., 1997, Med. Principles Pract. 6:91).

Briefly, for cloning of the specific gene into the expression vector, PCR amplification of the target gene using primers that contain restriction sites to generate in-frame fusions is performed. The PCR product is purified, and digested with the appropriate restriction enzymes and purified again. The vector DNA is cut with the appropriate restriction enzymes and purified. The PCR product and the vector are ligated, electroporated into DH5α, and grown in the presence of hygromycin overnight. Several antibiotic-resistant colonies are grown in a small volume of medium, and the plasmid DNA isolated by miniprep. The size of the insert is checked in these colonies. Inserts from one or more colonies are sequenced.

For electroporation into $M.$ $smegmatis$, the bacteria are grown shaking in 7H9 medium till they reach an absorbance of 0.8-1.0. The bacteria are harvested, washed twice with ice cold water, once with ice-cold 10% glycerol and suspended in the same. An aliquot of the cells are electroporated with the plasmid DNA from the colony whose insert was sequenced. The electroporated cells are grown for 3-4 hrs in 7H9, and plated on antibiotic containing plates. Several resistant colonies are grown in minimal media for 48-72 hrs. The $M.$ $smegmatis$ cell pellets are sonicated, the lysates fractionated by SDS-PAGE and the presence of the immunoreactive protein confirmed by reactivity with the antibody-containing urine samples. Colonies which express the desired protein are expanded, and the His-tagged recombinant protein is purified using of commercially available Nickel-agarose columns (Qiagen).

The reactivity of the recombinant protein with the entire cohort of urine samples is evaluated by ELISA as described herein. Combinations of antigens, preferably of individual epitopes, that provide the best sensitivity and specificity are delineated.

To produce one or more of the proteins in the 49-67 kDa range, an expression library of Mtb genomic DNA is screened with the antibody-positive urine samples. A pool of TB patient urine samples (which show strong reactivity on western blots with culture filtrate proteins of Mtb) from 10-15 TB patients is adsorbed against $E.$ $coli$ lysate, and used at an appropriate dilution to screen the library.

Briefly, $E.$ $coli$ Y1090, infected with appropriate plaque forming units of the phage from the library are plated in top agar on LB plates. After 2.5 hrs at 42° C., isopropyl β-D thiogalactoside (IPTG) saturated nitrocellulose filters are overlaid on the top of the plates for 2.5 hrs at 37° C. The filters are removed, washed extensively, and exposed to the pooled urine overnight. After washing again, the filters are exposed to 1:1000 dilution of Alkaline Phosphatase conjugated anti-human IgG, followed by BCIP-NBT substrate. The positive plaques (recombinant phages) are located on the original plates, excised and re-screened till purified.

The screening of the library by the urine antibodies can be expected to identify several proteins. To identify the clone(s) that expresses the antigen(s) which is recognized by antibodies from a large proportion of patients, the cloned phages are used to establish lysogens in E. coli Y1089. Single colonies from lysogens are grown in LB medium at 32° C. till an absorbance (at 600 nm) of 0.5 is obtained. The lysogens are induced to express the recombinant proteins by raising the temperature to 45° C. and addition of IPTG (10 mM). The cultures are grown for additional 1.5 hrs at 37° C. to allow accumulation of the recombinant proteins, and the bacterial pellets are obtained. The pellets are sonicated in small volume of PBS and the lysates fractionated on 10% SDS-PA gels and electroblotted onto nitrocellulose membranes. The blots are probed with individual urine samples from 20-25 TB patients, and clones coding for strongly immuno-reactive proteins recognized by all or a vast majority of the urine samples are identified. Lysates from E. coli Y1089 alone or Y1089 lysogenized with lambda gt11 vector are used as controls.

DNA from the recombinant clones encoding strongly immunoreactive proteins is isolated by the commercial Wizard Lambda Preps DNA Purification system (Promega), digested with EcoR1 and the insert obtained. The insert DNA from the clone(s) is subcloned into pGEMEX-1 vector (Promega) whose reading frame at the EcoR1 cloning site is identical to lambda gt11. Competent E. coli JM 109 cells are transformed with the recombinant plasmid (pGEMEX plus insert from the clone(s)). Plasmid DNA is isolated using Wizard Plus Minipreps (Promega), and used for automated sequencing with primers from SP6 and T3 promoter specific primers flanking the multiple cloning site in the PGEMEX-1 followed by 'primer-walking'. The nucleotide sequence is used in similarity searches against the Mtb genomic sequence to identify the protein and to obtain the sequence of the whole gene.

Once the protein has been identified and the sequence of the gene is known, cloning it for expression is done as was described above for the exemplary cloning of the MPT 51 gene.

To summarize, a combination of the antigens or individual epitopes already defined by serological studies, and new antigens/epitopes identified and produced as above, form the basis of a sensitive early diagnostic test for TB. If the sensitivity of antibody detection in urine samples is adequate, blood is no longer needed. If not, the combined serum+urine test provides a very sensitive diagnostic test. Use of the correct, well defined antigens on inexpensive formats (dip stick or flow through cassettes) provide a basis for an inexpensive, rapid diagnostic test for TB.

Vaccines

The foregoing disclosure and the Examples below prove that human subjects infected with Mtb indeed do make antibodies to the early antigens of this invention. Thus the antigens are available to the immune system and are immunogenic. Hence, the vaccine compositions and methods are designed to augment this immunity, and preferably, to induce it a stage wherein the bacterial infection can be prevented or curtailed. The vaccine compositions are particularly useful in preventing Mtb infection in subjects at high risk for such an infection, as discussed above. The vaccine compositions and methods are also applicable to veterinary uses.

Thus, this invention includes a vaccine composition for immunizing a subject against Mtb infection. An Mtb early antigen preferably one of the four described herein in more detail or a peptide thereof, is prepared as the active ingredient in a vaccine composition. These four proteins are (a) the 88 kDa protein having a pI of about 5.2 and SEQ ID NO:106; (b) the protein characterized as Mtb antigen 85C; (c) the protein characterized as Mtb antigen MPT51 (SEQ ID NO:107); and (d) the glycoprotein characterized as Mtb antigen MPT32. The vaccine may also comprises one or more of the proteins described herein, peptides thereof or functional derivatives as described, or DNA encoding the protein, and a pharmaceutically acceptable vehicle or carrier.

Preferred peptides for use in a vaccine composition, alone, in combination, or in linear multimers, include the 23 peptide described above in the context of diagnostic compositions.

In one embodiment, the vaccine comprises a fusion protein or peptide multimer which includes an Mtb early antigen, e.g., a full length protein and/or one or more of the above peptides, as described above.

The vaccine composition may further comprise an adjuvant or other immune stimulating agent. For use in vaccines, the Mtb early antigen protein or epitope-bearing peptide thereof is preferably produced recombinantly, preferably in prokaryotic cells.

Full length proteins or longer epitope-bearing fragments of the Mtb early antigen proteins are preferred immunogens, in particular, those reactive with early antibodies. If a shorter epitope-bearing fragment, for example containing 20 amino acids or less, is the active ingredient of the vaccine, it is advantageous to couple the peptide to an immunogenic carrier to enhance its immunogenicity. Such coupling techniques are well known in the art, and include standard chemical coupling techniques using linker moieties such as those available from Pierce Chemical Company, Rockford, Ill. Suitable carriers are proteins such as keyhole limpet hemocyanin (KLH), E. coli pilin protein k99, BSA, or rotavirus VP6 protein.

Another vaccine embodiment is a peptide multimer or fusion protein which comprise the Mtb early antigen protein or an epitope-bearing peptide region fused linearly to an additional amino acid sequence. Because of the ease with which recombinant materials can be manipulated, multiple copies a selected epitope-bearing region may be included in a single fusion protein molecule. Alternatively, several different epitope-bearing regions can be "mixed and matched" in a single multimer or fusion protein.

The active ingredient such, preferably a recombinant product, is preferably administered as a protein or peptide vaccine. In another embodiment, the vaccine is in the form of a strain of bacteria (preferably a known "vaccine strain") which has been genetically transformed to express the protein or epitope-bearing peptide. Some known vaccine strains of Salmonella are described below. Salmonella dublin live vaccine strain SL5928 aroA148fliC(i)::Tn10 and S. typhimurium LB5000 hsdSB121 leu-3121 (Newton S. M. et al., Science 1989, 244: 70

A Salmonella strain expressing the Mtb protein or fragment of this invention may be constructed using known methods. Thus, a plasmid encoding the protein or peptide. The plasmid may first be selected in an appropriate host, e.g., E. coli strain MC1061. The purified plasmid is then introduced into S. typhimurium strain LB5000 so that the plasmid DNA is be properly modified for introduction into Salmonella vaccine strains. Plasmid DNA isolated from LB5000 is introduced into, e.g., S. dublin strain SL5928 by electroporation. Expression of the Mtb protein or fragment encoded by the plasmid in SL5928 can be verified by Western blots of bacterial lysates and antibodies specific for the relevant antigen or epitope.

The active ingredient, or mixture of active ingredients, in protein or peptide vaccine composition is formulated conventionally using methods well-known for formulation of such vaccines. The active ingredient is generally dissolved or suspended in an acceptable carrier such as phosphate buffered saline. Vaccine compositions may include an immunostimulant or adjuvant such as complete or incomplete Freund's adjuvant, aluminum hydroxide, liposomes, beads such as latex or gold beads, ISCOMs, and the like. For example, 0.5 ml of Freund's complete adjuvant or a synthetic adjuvant with less undesirable side effects is used for intramuscular or subcutaneous injections, preferably for all initial immunizations; this can be followed with Freund's incomplete adjuvant for booster injections. General methods to prepare vaccines are described in *Remington's Pharmaceutical Science*; Mack Publishing Company Easton, Pa. (latest edition).

Liposomes are pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Adjuvants, including liposomes, are discussed in the following references, incorporated herein by reference: Gregoriades, G. et al., *Immunological Adjuvants and Vaccines*, Plenum Press, New York, 1989 Michalek, S. M. et al., "Liposomes as Oral Adjuvants," *Curr. Top. Microbiol. Immunol.* 146:51-58 (1989).

The vaccine compositions preferably contain (1) an effective amount of the active ingredient, that is, the protein or peptide together with (2) a suitable amount of a carrier molecule or, optionally a carrier vehicle, and, if desired, (3) preservatives, buffers, and the like. Descriptions of vaccine formulations are found in Voller, A. et al., *New Trends and Developments in Vaccines*, University Park Press, Baltimore, Md. (1978).

As with all immunogenic compositions for eliciting antibodies, the immunogenically effective amounts of the proteins or peptides of the invention must be determined empirically. Factors to be considered include the immunogenicity of the native peptide, whether or not the peptide will be complexed with or covalently attached to an adjuvant or carrier protein or other carrier and the route of administration for the composition, i.e., intravenous, intramuscular, subcutaneous, etc., and the number of immunizing doses to be administered. Such factors are known in the vaccine art, and it is well within the skill of the immunologists to make such determinations without undue experimentation.

The vaccines are administered as is generally understood in the art. Ordinarily, systemic administration is by injection; however, other effective means of administration are known. With suitable formulation, peptide vaccines may be administered across the mucus membrane using penetrants such as bile salts or fusidic acids in combination, usually, with a surfactant. Transcutaneous administration of peptides is also known. Oral formulations can also be used. Dosage levels depend on the mode of administration, the nature of the subject, and the nature of carrier/adjuvant formulation. Preferably, an effective amount of the protein or peptide is between about 0.01 µg/kg-1 mg/kg body weight. Subjects may be immunized systemically by injection or orally by feeding, e.g., in the case of vaccine strains of bacteria, $10^8$-$10^{10}$ bacteria on one or multiple occasions. In general, multiple administrations of the vaccine in a standard immunization protocol are used, as is standard in the art. For example, the vaccines can be administered at approximately two to six week intervals, preferably monthly, for a period of from one to four inoculations in order to provide protection.

Vaccination with the vaccine composition will result in an immune response, either or both of an antibody response and a cell-mediated response, which will block one or more steps in the Mtb bacterium's infective cycle, preferably the steps of binding to and entry into host cells in which it grows.

Having now generally described the invention, the same will be more readily understood through reference to the following examples which are provided by way of illustration, and are not intended to be limiting of the present invention, unless specified.

EXAMPLE I

Immunodominance of High Molecular Weight Antigens in Human Antibody Responses to Mtb Antigens Materials and Methods The study population included 58 $HIV^{neg}$ individuals with confirmed pulmonary TB. Of these, 16 were individuals attending the Infectious Disease Clinic at the Veterans Affairs Medical Center, New York. All patients were Mtb culture-positive, 9/16 patients were smear-negative, 14/16 showed minimal to no radiological lesions, and all were bled either prior to, or within 1-2 weeks of initiation of chemotherapy for TB. Eight sera were obtained from Leonid Heifitz and Lory Powell (National Jewish Center, Denver, Colo.). An additional 20 sera were provided by J. M. Phadtare (Grant Medical College, Bombay, India). Fourteen serum samples obtained from Lala Ram Sarup Tuberculosis Hospital, Mehrauli, New Delhi, India were provided by S. Singh. A majority of these 42 patients were smear-positive, had radiological appearance of moderate to advanced pulmonary lesions and were bled 4-24 weeks after initiation of chemotherapy. The control populations consisted of the following groups:

(a) 16 $HIV^{neg}$, $TB^{neg}$, $PPD^{+}$ healthy individuals (either recent immigrants from endemic countries or staff members involved in the care of TB patients in the VA Medical Center (b) 23 $HIV^{neg}$, $TB^{neg}$ healthy controls, 7 of whom were PPD skin test negative ($PPD^{neg}$), and the PPD reactivity of the remaining 16 individuals was unknown.

(c) 48 $HIV^{+}$, $PPD^{?}$, asymptomatic healthy individuals with CD4 cell numbers >800/$mm^3$.

Group (b) subjects were included because TB has emerged as a major opportunistic disease in the HIV-infected population.

Antigens

The antigen preparations were total cellular sonicate (CS), total culture filtrate (CF), lipoarabinomannan (LAM), LAM-free culture filtrate proteins (LFCFP), whole cell walls (CW), SDS-soluble cell wall proteins (SCWP), and cell wall core (CWC), all isolated from Mtb $H_{37}$Rv. CS was obtained from Mtb grown in Middlebrook 7H9 broth (Difco Laboratories, Detroit, Mich.) for 2-3 weeks. The bacilli were harvested by centrifugation at 1000 rpm for 30 min and the pellet resuspended in phosphate buffered saline (PBS) containing PMSF, EDTA and DTT at a final concentration of 1 mM each. The suspension was frozen in liquid nitrogen and thawed (several times) to weaken the cell walls, followed by sonication for 20 min at 4° C. The sonicate was centrifuged for 10 min at 10,000 rpm and the supernatant collected.

To obtain the remaining antigens, Mtb was grown to mid-logarithmic phase (14 days) in glycerol-alanine-salts medium. The cells were removed by filtration through a 0.22 μm membrane, and the culture supernatant was concentrated by ultrafiltration using an Amicon apparatus (Beverly, Mass.) with a 10,000 MW cut-off membrane. The concentrated material (CF) was dialyzed against 100 mM ammonium bicarbonate and dried by lyophilization.

To obtain the LFCFP, CF was suspended (7 mg/ml) in a buffer containing 50 mM Tris HCl (pH 7.4), and 150 mM NaCl, following which 20% Triton X-114 was added to obtain a final concentration of 4%. The suspension was allowed to rock overnight at 4°. A biphasic partition was set up by warming the 4% Triton X-114 suspension to 37° for 40 minutes, followed by centrifugation at 12,000×g. The aqueous phase was re-extracted twice with 4% Triton X-114 to ensure complete removal of the lipoarabinomannan, lipomannan (LM) and phosphatidyl-inositol-mannoside (PIM). The final aqueous phase was precipitated with 10 volumes of cold acetone, and the pellet washed several times with cold acetone to remove residual Triton X-114. The LAM-free aqueous phase CFPs were suspended in 100 mM ammonium bicarbonate, aliquoted and dried by lyophilization.

LAM, LM and PIM were extracted from whole cells by mechanical lysis of the bacilli in PBS (pH 7.4) containing 4% Triton-X 114 in a Bead Beater (Biospec Products, Bartelsville, Okla.). Unbroken cells and cell wall material were removed by centrifugation at 12000 g, 4° for 15 min. The supernatant was collected and a biphasic partition set up. The detergent phase was obtained, back-extracted several times with cold PBS and the macromolecules in the final detergent phase were precipitated with 10 volumes of cold acetone. The precipitate was collected by centrifugation and allowed to air dry. This material (which contained the lipoglycans) was suspended in PBS and residual proteins were removed by extraction with PBS-saturated phenol. The aqueous phase was collected and, after dialyses against distilled water, the lipoglycans were lyophilized. LAM was further purified away from LM and PIM by size exclusion chromatography as previously described (Chatterjee, D. et al., 1992, *J. Biol. Chem.* 269:66228-66233).

To isolate total CW, Mtb cells were inactivated by isothermal killing at 80° for 1 h and suspended at a concentration of 0.5 g cells/ml, in a buffer containing PBS, pH 7.4, 4% Triton X-114, PMSF, pepstatin, EDTA, and DNase. The cells were disrupted in a Bead Beater using 0.1 mm Zirconia beads. The lysed cells were first centrifuged at 3000×g for 5 min to remove unbroken cells followed by centrifugation at 27,000× g, 4° for 20 min. The resulting pellet was washed three times with cold PBS at room temperature. This final pellet was termed the CW.

The SCWP were obtained by washing the CW twice with 2% SDS in PBS, pH 7.4 at room temperature. The tightly associated proteins were isolated by extracting the CW pellet three times with 2% SDS in PBS, pH 7.4, at 55°. The 55°, 2% SDS extract was recovered, and the SDS was removed by using an Extracti Gel column (Pierce, Rockford, Ill.). The eluate from the column was dialyzed against twice-distilled $H_2O$, aliquoted and dried by lyophilization.

The CWC (mycolyl-arabinogalactan-peptidoglycan complex) was generated as described (Daffe, M. et al., 1990, *J. Biol. Chem.* 265:6734-6743) with minor modifications. The SDS-insoluble material obtained after extraction of the SCWP was suspended in PBS, 1% SDS, 0.1 mg/ml proteinase K and incubated for 20 h at 50°. The insoluble material was pelleted by centrifugation, washed twice with 2% SDS at 95° for 1 h and collected by centrifugation. This was washed several times with water and 80% acetone to remove SDS.

Fractionation of LFCFP by size was performed by using a preparative SDS-PAGE system (model 491 Prep cell, Bio-Rad, Hercules, Calif.). CFP (20-25 mg) was loaded directly onto a 30 ml 10% preparative polyacrylamide tube gel containing a 6% stacking gel, that was poured in a casting tube with a 37 mm internal diameter. The running buffer used consisted of 25 mM Tris, pH 8.3, 192 mM glycine, 0.1% SDS. The proteins were separated by electrophoresis using an increasing wattage gradient of 8 W for 3.13 h, 12 W for 2.5 h, and finally 20 W for 11.1 h. Proteins were eluted from the bottom of the tube gel with a constant flow of 5 mM sodium phosphate, pH 6.8. The initial 65 ml of eluant were collected as the void volume, after which 80 fractions of 4.2 ml were collected at a rate of 0.4 ml/min. Individual fractions were assayed by one dimensional SDS-PAGE and were pooled accordingly. SDS was removed from the pooled concentrated fractions by elution through an Extracti-Gel (Pierce) column. The pooled fractions were dried and stored frozen until testing.

Adsorption of Sera with *E. coli* Sonicate

Overnight cultures of *E. coli* (Y1090) grown in Luria-Bertani medium were centrifuged to obtain bacterial pellets that were treated as described for the Mtb sonicate, except that sonication was performed for 30 sec. Two hundred μl of *E. coli* lysate suspended at 500 μg/ml in 20 mM carbonate buffer, pH 9.6, was coated into each well of an Immulon 2® ELISA plate (Dynatech, Alexandria, Va.) overnight. The plates were washed and blocked with 5% BSA (bovine serum albumin, Sigma Immunochemicals, St. Louis) in PBS for 90 min. HIV was inactivated by addition of Triton X-100 (1% final concentration) to each serum sample, followed by heating at 55° for 60 min. Samples from non-HIV infected individuals were treated in the same manner to maintain consistency in sample preparation. Serum from each individual (20 μl) was diluted to 200 μl in PBS/Tween 20 (0.05%) in a 96-well tissue culture plate. The diluted serum samples were transferred to the *E. coli*-coated, blocked ELISA plate by using a multichannel pipetter. The sera samples were exposed to the bound *E. coli* antigens for 90 min after which they were transferred to another ELISA plate that had been coated with *E. coli* and blocked as above. The serum samples were exposed to 8 cycles of adsorption with *E. coli* antigens, following which they were transferred to a 96-well tissue culture plate where sodium azide (1 mM final concentration) was added to each well. This protocol allows rapid and efficient processing of small volumes of multiple samples. Adsorbed serum samples were used within one week.

ELISA with Mtb Antigens

Fifty μl of antigen, suspended at 5 μg/ml (except CS and SCWP, which were used at 15 μg/ml and 1 μg/ml respectively) in coating buffer were allowed to bind overnight to wells of ELISA plates. After 3 washes with PBS, the wells were blocked with 7.5% FBS (fetal bovine serum, Hyclone, Logan, Utah) and 2.5% BSA in PBS for 2.5 h at 37°. Following this, sera were diluted to 1:1000 final dilution in PBS/Tween 20 (0.05%, PBST) containing 1% FCS and 0.25% BSA, and 50 μl of each serum sample was added per well. The antigen-antibody binding was allowed to proceed for 90 min at 37°, following which the plates were washed 6 times with PBST. Fifty µl of alkaline phosphatase-conjugated goat anti-human IgG (Zymed, Calif.), diluted 1:2000 (in the same diluent as the serum samples) were added to each well. After 60 min the plates were washed 6 times with Tris-buffered saline (50 mM Tris, 150 mM NaCl) and the Gibco BRL Amplification System (Life Technologies, Gaithersburg, Md.) used for development of color. The plates were read at 490 nm after stopping the reaction with 50 µl of 0.3M $H_2SO_4$.

The optimal antigen and antibody concentrations for each antigen were determined by checkerboard titration with limited numbers of control and non-TB sera prior to performing the ELISA with the total serum panel.

The ELISA with each of the sized fractions generated by preparative polyacrylamide gel electrophoresis was performed as described as above, except that antigen was coated at 2 µg/ml and the sera were tested at a final dilution of 1:200. Forty-two TB sera and 44 non-TB controls (16 $PPD^+$; 7 $HIV^{neg}$, $PPD^{neg}$; and 21 $HIV^+$, asymptomatic individuals) were included in these assays.

Characterization of Known Antigens of *M. tuberculosis* in the Sized Fractions of LAM-Free CFP The following mAbs were obtained from the World Health Organization (courtesy of Dr. Thomas M. Shinnick, Centers for Disease Control, Atlanta):

| | | | | | | |
|---|---|---|---|---|---|---|
| IT-53 | IT-13 | IT-46 | IT-63 | IT-61 | IT-51 | MLO4-A2 |
| IT-45 | IT-64 | IT-15 | IT-49 | IT-52 | IT-69 | SAID2D |
| IT-42 | IT-70 | IT-23 | IT-48 | IT-67 | IT-4 | CS-01 |
| IT-41 | IT-43 | IT-62 | IT-59 | IT-68 | IT-1 | |
| IT-56 | IT-58 | IT-47 | IT-60 | IT-19 | IT-20 | |

The "IT" designations are World Health Organization standards for its collection of anti-Mtb antibodies. The alternative names of the mAbs, the antigens they recognize and the laboratory of origin are provided in Engers, H. et al., 1986, *Infect. Immun.* 51:718-720; Khanolkar-Young, S. et al., 1992, *Infect. Immun.* 60:3925-3925; Young et al., supra, which are incorporated by reference in their entirety. Antiserum to the 50/55 kDa antigen, MPT32, was obtained from the NIH, Contract 1-AI-25147. The table below summarizes these antibodies and their reactivities.

The composition of the sized fractions was probed with the antibodies in an ELISA, similar to what was used for assessment of reactivity with human sera, except that 50 µl/well of each antibody defined above was used at a concentration recommended by the contributing laboratory. For these ELISAs, the second antibody was an alkaline phosphatase-conjugated rabbit anti-mouse IgG or goat anti-rabbit IgG (1:2000, Sigma Immunochemicals) added in a volume of 50 µl well.

SDS-PAGE and Immunoblotting

All fractionations (LFCFP and fractions thereof) were done on 10% SDS-PA mini-gels, and the proteins transferred to nitrocellulose membranes before probing with the antibodies. To better identify the antigens in fraction 15 recognized in ELISA by the test sera, blots of total LFCFP and fractions 10 and 15, were probed with (a) a pool of 6 TB sera that were positive for reactivity with LFCFP by ELISA;

(b) a pool of 6 TB sera that were negative by ELISA; and (c) a pool of 6 sera from $PPD^+$ healthy controls.

All blots were screened for antibody binding by use of alkaline phosphatase-conjugated rabbit anti-human IgG and subsequently developing the color reaction with BCIP/NBT substrate (Kirkegaard & Perry Laboratories, Gaithersburg, Md.).

Statistical Analyses

The cutoff for positivity in all ELISA assays was set to be the mean absorption or optical density (OD)±3 standard deviations (SD) of the control group. The Wilcoxon signed rank test for paired samples was used to compare reactivity of sera pre- and post-adsorption. The SD of the above two groups were compared by using the F test. The reactivity of TB sera with LFCFP was compared to the reactivity with the other antigen preparations by using McNemar's paired test. The Graphpad Instat program was used for all statistical analyses.

Results

A. Effect of Adsorption of Test Sera with *E. coli* Lysate

The reactivity of sera from 38 $HIV^{neg}$, (16 $PPD^+$, 7 $PPD^{neg}$, 15 PPD unknown) non-tuberculosis individuals, 21 HIV-infected asymptomatic individuals, and 42 TB patients with the LFCFP was evaluated before and after depletion of cross-reactive antibodies by adsorption with *E. coli* lysate (FIG. 1). There was no difference in the reactivity of the different subgroups of the control sera. The mean absorption (O.D.±SD) of the unadsorbed control sera was 0.316±0.111, and of the same sera after adsorption was 0.165±0.05 (Table 1). This reduction in reactivity was statistically significant ($p<0.0001$). In addition, the variance (expressed as SD) of the control sera samples post-adsorption was significantly lower ($p<0.0001$) when compared to the SD of the same sera preadsorption (FIG. 1, Table 1). The mean O.D. for the preadsorbed TB sera was 0.911±0.454, and the same sera post-adsorption had a mean O.D. of 0.694±0.440 (FIG. 1). Although the reactivity of the adsorbed TB sera was also reduced significantly as compared to preadsorbed sera ($p<0.0001$), the SD of the pre-adsorbed and post-adsorbed TB samples were similar. Thus, significant levels of cross-reactive antibodies that were adsorbable to the *E. coli* lysate were present both in the control and test sera. For the control group, removal of these antibodies reduced the baseline sera reactivity. However, as expected, despite the decreased antibody levels, the variability between individual TB sera was unaffected. Three S.D. above the mean of the respective control sera was set as the threshold values for positive reactivity.

Antibodies reactive with LFCFP were detectable in 25/42 (60%) of the unadsorbed TB sera (FIG. 1). When tested postadsorption, anti-mycobacterial antibodies were detectable in 4/17 (24%) additional, previously negative sera, raising the sensitivity to 69% (FIG. 1).

TABLE 1

Comparison of preadsorbed sera with *E. coli*-adsorbed sera

| | Mean O.D. ± S.D. | | | |
|---|---|---|---|---|
| Sera | Pre Adsorption | Post Adsorption | p value[a] | p value[b] |
| Controls | 0.316 ± 0.111 | 0.165 ± 0.050 | <0.0001 | <0.001 |
| TB Patients | 0.911 ± 0.454 | 0.694 ± 0.440 | <0.0001 | NS |

[a]Wilcoxon signed rank test comparing the preadsorbed and post adsorbed sera.
[b]F test comparing the standard deviations of the preadsorbed and post adsorbed sera. NS: not significant.

These experiments were also analyzed by using the highest O.D. in the control sera group as the cutoff, as has been done by others (Ivanyi et al., 1989, supra). Prior to adsorption, O.D.s obtained with 59 control sera ranged from 0.16 to 0.68 (FIG. 1). Twenty-four of the 42 (57%) TB sera had O.D.s greater than the highest control value. After adsorption, the range of O.D.s with the same control sera was 0.08 to 0.25, and 31/42 (74%) TB sera were found to be antibody positive. Thus, antibodies to Mtb antigens were now detectable in 7/18 (39%) additional, previously negative sera. In view of the increased sensitivity obtained with adsorbed sera, all sera were hereafter preadsorbed prior to use in any assay.

EXAMPLE II

Antibodies to an 88 kDa Secreted Antigen of *M. tuberculosis* Serve as a Surrogate Marker of Pre-Clinical TB in HIV-Infected Subjects A. Materials and Methods 1. Sera:

The study population included 49 HIV-infected individuals attending the Infectious Disease Clinic at the V.A. Medical Center, New York, who developed or presented with TB (HIV/TB) during the last several years. A total of 259 serum samples were available from these individuals. Of these samples:

(a) 136 were obtained from 38 patients on several occasions prior to manifestation of clinical TB ("HIV/pre-TB");
(b) 37 samples were obtained from 37 patients at the time of clinical and bacteriological diagnosis of TB ("HIV/at-TB") and included several patients from group (a); and
(c) 86 sera were obtained from 35 patients within a few months of initiation of therapy for TB ("HIV/post-TB"). A majority of patients in group (c) were also members of groups (a) and/or (b).

The diagnosis of TB was based on positive cultures for Mtb.

Sera from 20 non-HIV TB patients (non-HIV/TB), 19 of whom were smear-positive, and all of whom showed radiological evidence of moderate to advanced cavitary disease, were included as positive controls. Sera from 19 non-HIV/PPD skin test-positive individuals were included as negative controls. To rule out nonspecific reactivity, the study included (i) sera from 35 HIV-infected, asymptomatic individuals, with CD4 cell counts >800 and (ii) 48 serum samples from 16 HIV-infected subjects whose blood cultures were positive for *Mycobacterium avium*-intracellulare ("HIV/MAI"). Of these, 28 HIV/MAI serum samples were obtained during the months preceding advent of MAI bacteremia.

The secreted antigens of Mtb H37Rv (referred to as LAM-free culture filtrate proteins (LFCFP) were prepared as described in Example I. This antigen mixture was subsequently fractionated based on the molecular weight of the proteins using a BioRad 491 Prep Cell (Hercules, Calif.) with a 30 ml 10% preparative polyacrylamide tube gel containing a 6% stacking gel as above. Fractions were pooled according to molecular weights (as determined by SDS-PAGE) and dried.

The LFCFP and the sized fractions thereof, were resolved on 10% SDS-PA mini gel and transferred onto a nitrocellulose membrane prior to probing with sera. The second antibody used was alkaline-phosphatase conjugated rabbit anti-human IgG and the substrate was BCIP/NBT (Kirkegaard and Perry Laboratories, Gaithersburg, Md.).

All sera were adsorbed with *E. coli* lysates prior to use in ELISA assays. Adsorptions and ELISAs were performed as described in Example I.

2. Staining of Lymphocytes and Flow Cytometric Analyses

Staining of cells was done by standard procedures (Gordin F. M. et al., 1994, *J. Infect. Dis.* 169:893-897) using the Simultest CD3/CD4 and CD3/CD8 (Becton Dickinson Immunocytochemistry systems, San Jose, Calif.) reagents. Flow cytometry was carried out with a Becton Dickinson FACScan.

3. Statistical analysis: performed as above.

B. Results

1. Reactivity of Sera from HIV/TB Patients with *M. tuberculosis* Antigens

Figure 2:
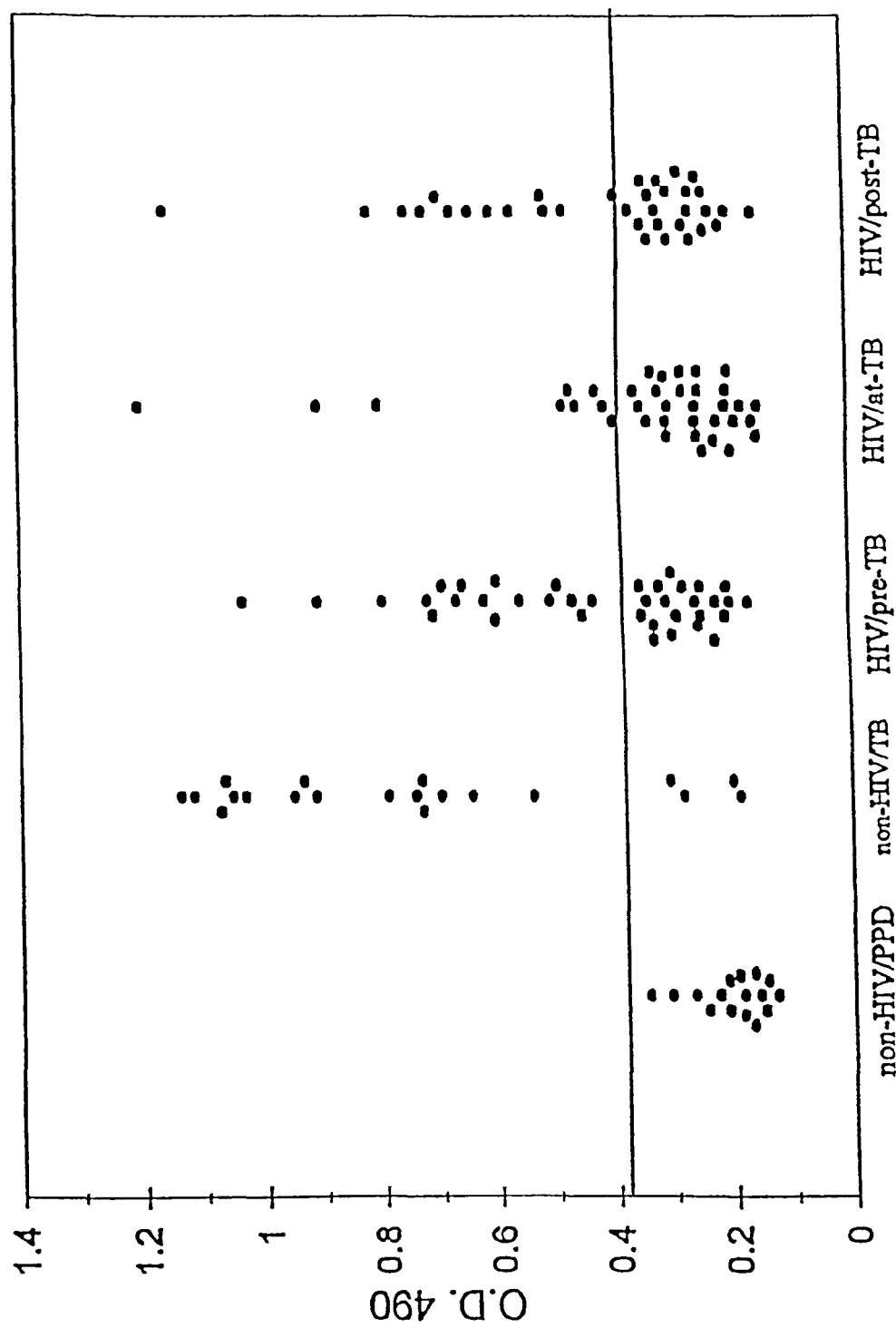
FIG. 2 shows reactivity of sera from non-HIV, PPD skin test positive ($PPD^+$) healthy controls (non-HIV/PPD), non-HIV TB patients (non-HIV/TB) and HIV-infected TB patients (HIV/pre-TB, HIV/at-TB and HIV/post-TB) with total LFCFP of Mtb. The cut-off was determined by the mean optical density (OD)±3 standard deviations, obtained with the healthy control sera.

The reactivity of 259 sera from 49 HIV/TB patients with the total LFCFP of Mtb was compared to reactivity of sera from 16 non-HIV/PPD$^+$ individuals (negative controls) and 20 non-HIV/TB patients (positive controls). Each serum sample from each subject was evaluated at least three times for presence of anti-Mtb antibodies. A representative ELISA assay showing the antibody levels for each of these groups is presented in FIG. 2. With the cutoff set as the mean OD±3SD of the 16 sera from non-HIV/PPD$^+$ individuals, antibodies to the LFCFP were found in 16/20 (80%) of non-HIV/TB sera. In contrast, only 9/37 (24%) of the HIV/at-TB sera had such antibody reactivity. However, HIV/pre-TB sera from 17/38 (45%) of HIV/TB patients were positive, as were 13/35 (34%) HIV/post-TB sera.

In general, sera of HIV$^+$ subjects had lower levels of antibody than did non-HIV subjects (in all three groups). The difference between mean O.D. of the non-HIV/TB and the mean O.D. of the HIV/at-TB group was statistically significant (in comparisons of either all sera (p=0.0001), or of only antibody-positive sera (p=0.0165)). Antibody levels measured as OD in HIV/pre-TB sera were significantly lower than in non-HIV/TB sera (p=0.0001 for all sera; p=0.0007 for antibody-positive sera).

The specificity of the anti-Mtb antibody responses in the HIV/TB patients was evaluated. Sera from 35 HIV-infected asymptomatic individuals (CD4$^+$ cell counts>800) and 48 sera from 16 HIV/MAI patients were tested along with 19 non-HIV/PPD$^+$ healthy controls and 20 non-HIV/TB patients. Using the mean OD±3SD of the 19 non-HIV/PPD$^+$ control sera as the cutoff, 2/35 sera from the HIV-$^+$ group and 7/48 sera from the HIV/MAI group showed minimal reactivity with the Mtb secreted antigens. These results confirmed the specificity of the reactivity of HIV/TB sera with Mtb antigens.

2. Time Course of Appearance of Anti-Mtb Antibodies in HIV/TB Patients

Since antibodies to the secreted antigens of Mtb were present in about half of the HIV/pre-TB sera, the presence of these antibodies in the years preceding the clinical presentation of TB was determined. Anti-Mtb antibodies were tested in multiple sera from 6 antibody-positive, 3 antibody-negative HIV/TB patients, and 3 HIV/MAI patients. All 6 antibody-positive individuals had circulating antibodies for different intervals during the years preceding the clinical manifestation of TB. One of the six patients developed anti-Mtb antibodies about 1.5 yr before clinical diagnosis of TB, and another about 4.5 yr prior to that time. The remaining 4 patients had circulating antibodies for the preceding 5-6 yr. In contrast, similar samples from 3 antibody-negative HIV/TB patients and 3 HIV/MAI bacteremia patients were consistently negative.

3. Reactivity of HIV/TB Sera with Fractionated Secreted Antigens

To determine if the profile of antigens (in the LFCFP preparation) reactive with antibodies of HIV/TB patients was different from the profile of antigens recognized by antibodies of non-HIV/TB patients, Western blots prepared from SDS-PAGE-fractionated LFCFP were probed with sera from nine ELISA$^+$ (two HIV/at-TB, seven HIV/pre-TB) and three non-HIV/TB patients. These results were compared to the antibody reactivity of six HIV-$^+$ asymptomatic controls and five non-HIV/PPD$^+$ healthy controls (ELISA$^{neg}$). As described in Example I, all sera (healthy and disease) reacted with antigens of 65 kDa and 30-32 kDa. The sera from non-HIV/TB patients reacted with multiple antigens (approximately 20) ranging in size from about 26 kDa to about 115 kDa. Of these, the strongest reactivity was seen with the 38 kDa antigen, which is present in large amounts, and with an 88 kDa antigen, present in lower amounts. Reactivity was also observed with several antigens of molecular weights of 32-38, 45-65, 72-78 and 80-115 kDa.

In contrast, 8/9 of the HIV/TB sera showed no reactivity with the 38 kDa antigen, although the reactivity with the antigens in the 45-65 kDa range was detectable, albeit very low in some patients. The reactivity with the 72-78 kDa antigens was also reduced or completely lost. Reactivity to the 80-115 kDa antigens was maintained in two patients, but was significantly reduced in the remaining patients. Reactivity with the 88 kDa antigen appeared to be maintained at higher levels in most HIV/TB sera than was reactivity with the other antigens in this molecular weight range. None of the sera from the asymptomatic HIV-infected individuals or from PPD$^+$ healthy controls showed any significant parallel reactivity at similar dilutions. Thus, it was concluded that the repertoire of antigens recognized by the HIV/TB sera was more limited than that recognized by non-HIV/TB sera.

4 Reactivity of HIV/TB Sera with Sized Fractions of LFCFP

In order to narrow the search for the antigens in the LFCFP that were recognized by HIV/TB patients, the LFCFP material was fractionated into 14 overlapping fractions based on molecular weight. Identification of fractions containing strongly seroreactive proteins was achieved by probing Western blots with pooled sera from six ELISA$^+$ non-HIV/TB or six HIV/TB patients. Besides the 65 kDa and 30-32 kDa antigens which were previously shown (Example I) to be reactive with all sera (healthy and disease), the non-HIV/TB serum pool reacted primarily with antigens with molecular weights above 30-32 kDa in fractions 6-14.

More specifically, reactivity was observed with antigens of approximately 32-38 kDa in fractions 6, 7 and 8. A very strong band at 38 kDa was reactive in fractions 9 and 10. In addition, antigens of 45, 50 and 58-60 kDa were also reactive in fraction 10. Although small amounts of the 38 kDa antigen and the 30-32 kDa were found to contaminate fractions 11-14, the dominant seroreactive proteins in fraction 11 ranged from 56-68 kDa, in fraction 12 from 58-76 kDa, in fraction 13 from 65-76 kDa and in fraction 14 from 65-88 kDa. A strong band at 88 kDa was seen exclusively in fraction 14.

When pooled sera from 6 ELISA$^+$ HIV/TB patients (5 HIV/pre-TB and 1 HIV/at-TB) was used to probe a similar blot, antigens in fractions 6-9 reacted poorly. In accordance with the results from tests of individual HIV/TB sera (, little or no reactivity was found with the 38 kDa antigen in fractions 9-14. However, reactivity with antigens of 45, 50 and the 58-60 kDa doublet in fraction 10 was discernible, though it was relatively weak. Except for the 68 kDa antigen in fractions 11 and 12 (which reacted strongly with the non-HIV/TB sera pool), reactivity with the other antigens in fractions 11-14 was also maintained. The reactivity with the 88 kDa antigen in fraction 14 was strong and clear.

These results suggest that reactivity with antigens in fractions 10-14 is better maintained in HIV/TB sera than with the antigens in the remaining fractions. Thus, of the antigens recognized by non-HIV/TB patients, HIV/TB patients recognize only a subset. For example, antibodies to the 38 kDa antigen are not found in HIV/TB, whereas antibodies to antigens in fraction 10-fraction 14, and in particular to the 88 kDa antigen are maintained despite HIV infection.

5. Reactivity of Mtb Antigen Fractions with Individual Sera.

To determine precisely which antigens of Mtb are recognized with high frequency by HIV/TB patients, reactivity with antigens in fractions 7 through 14, and with total LFCFP (as positive control) was tested with 145 sera from 42 HIV/TB patients. Because the goal of these studies was to identify Mtb antigens that may be used for developing a surrogate marker for subclinical TB, or as an aid to diagnosis of patients presenting with suspected TB, mostly HIV/pre-TB and HIV/TB sera were used. Sera from 18 non-HIV/PPD$^+$ (negative controls) and 20 non-HIV/TB patients (positive controls) were included.

As shown above (e.g., FIG. 2), using the mean OD±3SD obtained with the non-HIV/PPD$^+$ control sera as cutoff, 16/20 (80%) non-HIV/TB sera had antibodies to the total LFCFP. Fifty percent (21/42) of the HIV/TB patients had antibodies to the unfractionated LFCFP. However, 74% (31/42) of the same patients showed positive reactivity with antigens in fraction 14. Sixty two percent (26/42) patients were reactive with antigens in fraction 13, and 38% (16/42) with fraction 12 (though the O.D. values for fraction 12 and 13 antigens were lower). About 50-60% of sera reacted with antigens in fractions 9 and 10, albeit at lower levels than with fraction 14. As was shown in Example I, the non-HIV/TB patients who were reactive with the unfractionated LFCFP were also reactive with the antigens in fraction 14 in this study The reactivity of HIV/TB sera with the unfractionated LFCFP and antigens in fraction 14 was also analyzed by comparing HIV/pre-TB and HIV/at-TB groups. Thirty-one percent of the HIV/at-TB were reactive with the total LFCFP, as were 55% of the HIV/pre-TB sera. In contrast, 66% of the HIV/at-TB, and 74% of the HIV/pre-TB sera had antibodies which bound fraction 14 antigens.

To follow the time course of appearance of antibodies to fraction 14 antigens, the reactivity of multiple serum samples from individual patients was tested with fraction 14 and with LFCFP. Antibodies to these antigens were present in the sera of individual (antibody-positive) patients for several years before, and at the time of, clinical manifestation of TB. In contrast, multiple serum samples from antibody-negative patients were consistently negative.

6. Cellular Profiles of Antibody-Positive and Negative HIV/TB Patients

The T cell profiles of HIV/TB patients who were antibody-positive with fraction 14 antigens were compared with those who were antibody-negative, both during the HIV/pre-TB and HIV/at-TB stages. There was no significant differences between the two groups of HIV/TB patients.

C. Discussion

This foregoing results prove that antibodies to secreted antigens of Mtb are present in about 74% of the HIV/TB patients for several months to years preceding the clinical manifestation of TB. Prior depletion of cross-reactive antibodies allows the detection in a serum sample of such "early" anti-mycobacterial antibodies, because of their lower levels compared to non-HIV/TB patients and the "unmasking" of their reactivity as a result of the depletion.

The repertoire of Mtb antigens which elicit antibodies in the HIV/TB patients is limited in comparison to non-HIV/TB patients: antibodies to several antigens with molecular weights of 32-45 kDa are absent in these HIV/TB patients. Antibodies to a strongly seroreactive 38 kDa antigen, which are present in 50-60% of non-HIV/TB TB patients, were absent from most HIV/TB patients. (Example I; Daniel et al., 1987, supra; Bothamley, 1992, supra; Espitia C. et al., 1989, supra; Verbon A. et al., 1993, *Am Rev Respir Dis* 148:378-384) Most noteworthy, among the antigens recognized by antibodies in HIV/TB sera were antigens present in fraction 14, which comprises primarily an 88 kDa reactive antigen. Such antibodies specific for the 88 kDa antigen were detected in pre-TB sera from 74% of the HIV$^+$ individuals who went on to develop clinical TB.

Example I shows that the 88 kDa antigen (GlcB) (present in Fraction 15 in that study, but present in Fraction 14 in the study of Example II) is one of the secreted antigens of Mtb that elicits antibodies during early stages of disease progression (in non-HIV TB patients). Thus, the detection of anti-88 kDa antibodies in the high risk HIV-infected population can serve as a diagnostic test, and the antibody as a surrogate marker, for identifying individuals with active pre-clinical TB. At the time TB appears clinically, only about one-third of the HIV/TB patients are PPD$^+$ (Fitzgerald J. M. et al., *Chest* 100:191-200), a measure of T cell-mediated immunity. In contrast, 66% of these HIV/TB patients have antibodies to the 88 kDa antigen (GlcB). The discovery of this new surrogate marker, as well as others based on other "early" antibodies, for identifying individuals who are at increased risk of developing TB or have active TB, is a significant contribution to the effort to slow the impending global TB epidemic.

In the U.S., only about 3% of the TB patients are HIV-infected. However, in the developing countries, seroprevalence for HIV ranges from 17% to 66% (Raviglione et al., 1992, supra; Shafer et al., supra). The proportion of HIV patients who are anergic to PPD is large, ranging from 33% in Zaire to over 90% in Brazil, and ranges from 43% in early HIV infection to 100% in advanced HIV disease (Raviglione et al., 1992, supra).

Delayed hypersensitivity skin test reactivity is known to be unstable in HIV$^+$ individuals. Since development of PPD reactivity and production of anti-mycobacterial antibodies do not necessarily occur simultaneously (Das, S. et al., *Clin. Exp. Immunol.* 1992; 89:402-06; Kardjito, T. et al., *Tubercle.* 1988, 63:269-274; Balestrino, E. A. et al., *Bull. World Health Org.* 1984, 62:755-761), the simultaneous use of both markers will enhance early detection and our ability to institute timely therapy in such patients.

A number of investigators presented controversial results in their attempts at serological diagnosis of TB in HIV-infected patients. For example, van Vooren et al., supra, reported that antibodies to total secreted antigens of Mtb were present for several months in a patient who subsequently developed TB. They also reported that 7 of 8 HIV/TB patients had circulating antibodies to antigen p32 (Ag85A). This antigen would be in fractions 6 to 9 in the studies described herein. Indeed, the reactivity of the HIV/TB sera with these fractions might be attributable to the presence of this antigen, given that antibodies specific for the 38 kDa antigen and the Ag85B antigen (McDonough et al., supra, are lacking in these patients. Da Costa et al., supra, found anti-LAM antibodies in about 35% of their HIV/TB patients, as did Barer et al. (supra) using PPD as the antigen (*Tuber Lung Dis* 1992, 73:187-91). The results reported herein are similar in that, at the time clinical TB is manifest, antibodies to unfractionated LFCFP were detectable in about 25% of the HIV/at-TB sera. However, sera from 66% of these patients were reactive with the fraction 14 antigens. The inability of McDonough et al. (supra) to detect antibodies to Ag85B in sera of HIV/TB patients may be due to the limited numbers of antigens recognized by the HIV/TB patients. The A-60 antigen used by some investigators (Saltini et al., supra; van der Werf et al., supra) provides poor sensitivity and poor specificity even in the non-HIV/TB patients, a group known to have higher antibody levels (Charpin D et al., *Am Rev Respir Dis* 1990, 142:380-384; Qadri, S. et al., *Can J Microbiol* 1991, 38:804-806).

It is not clear why about 25-30% of the HIV/TB patients appear to lack antibodies to the 88 kDa antigen GlcB. No correlation was found between the CD4$^+$ cell counts and antibody levels in the HIV/TB patients. Similarly, a lack of correlation between CD4$^+$ cell counts and delayed hypersensitivity responses has also been reported (Huebner et al., 1994, supra), suggesting not only quantitative alterations but also functional differences between T cell subpopulations contributing to the immune status of HIV-infected individuals.

The presence of circulating antibodies to secreted antigens of Mtb long before the development of clinical disease in the HIV/TB patients suggests some replication of Mtb in vivo before the immune system becomes sufficiently dysfunctional to allow the progression to clinical disease. Epidemiological studies show rapid progression of primary infection to clinical disease in HIV-infected individuals (Small, P M et al., *N Engl J Med* 1993, 328:1137-1141; Daley, C L et al., *N Eng. J Med* 1992, 326:231-235; Edlin B R et al., *N Engl J Med* 1992, 326:1514-1521; Coronado V G et al., *J Infect Dis* 1993, 328:1137-1155). It is therefore possible that only patients who are reactivating latent TB and are therefore mounting a secondary immune response, have anti-Mtb antibodies. Interesting recent studies analyzing Restriction Fragment Length Polymorphisms (RFLP) of the Mtb strains (Alland D et al., *N Engl J Med* 1994, 330:1710-1716; Small et al., supra) suggest that about 60-70% of the TB cases in New York (and San Francisco) are due to reactivation of latent infection.

Anti-mycobacterial antibodies in seemingly antibody-negative patients may be circulating in the form of immune complexes with the antigens, thereby obscuring the presence of antibody in the assay used. That this may occur in at least a proportion of the patients is suggested by the increased frequency of antibodies detected in HIV/post-TB sera.

The present results suggest that patients with persistently circulating antibodies to the Mtb 88 kDa antigen, GlcB, may benefit from preventive anti-TB therapy, as has been found to be the case with PPD$^+$ HIV-infected individuals (Shafer, et al., supra; Pape, J. W. et al., *Lancet* 1993, 342:268-272). The patients in the present inventors' cohort were chosen on the basis of clinical confirmation of TB. Their PPD reactivity is not known. The length of time from a positive PPD skin test to the development of clinical disease ranges from 1-7 years in HIV-infected individuals (Selwyn et al., supra; Huebner et al., supra. There is no parameter which assists in determining the most appropriate time and duration of prophylactic anti-TB therapy. Further analyses of antibody responses in HIV/PPD$^+$ individuals who progress to clinical TB may provide further insight into the most appropriate timing for prophylactic therapy in these individuals.

EXAMPLE III

Definition of Mtb Culture Filtrate Proteins by 2-D Polyacrylamide Gel Electrophoresis Mapping, N-terminal Amino Acid Sequencing and Electrospray Mass Spectrometry As described above, in vitro cultivation of Mtb results in the accumulation of a complex set of proteins in the extracellular milieu, collectively termed the culture filtrate proteins (CFPs). The most notable feature of this protein fraction is its immunodominance. CFP has been suggested to be a major repository of antigens involved in the protective immune response and to provide biochemical definition of this fraction. More recently, it has been contended that the dichotomous immune responses engendered by vaccination of experimental animals with live versus heat killed bacilli are attributable to the active secretion of such antigens by viable Mtb. This hypothesis is supported by the demonstration of the ability of Mtb CFP to induce a protective T-cell response. Attempts to define the immunologically active components within this fraction has led to the purification and characterization of several proteins including the 6 kDa ESAT6, 24 kDa MPT64, the Ag85 complex and MPT32. A strong antibody response against some of the CFPs has been noted, including the MPT32, 38 kDa PstS homologue and the 88 kDa protein GlcB. The present inventors have found these antigens and others described herein to be useful tools for early serodiagnosis of TB.

In the most extensive characterization of the Mtb CFPs prior to this invention, Nagai and colleagues purified twelve major proteins, partially characterized them and mapped them by 2-D PAGE. Several other proteins, primarily those defined by mAb reactivity, have been located within culture filtrate preparations. Culture filtrates include not only actively secreted proteins but also somatic molecules that are released into the medium during replication or by autolysis. As demonstrated by Andersen et al. (supra) the protein profile of the culture filtrate is highly dependent on cultivation time. Further, the medium used and the means of incubation (static vs. shaking) may also impact on the profile of CFP. Thus, due to variations in the protocols used for CFP preparation, a clear understanding of the protein composition of this fraction is difficult to obtain from the current literature.

In this Example, the present inventors have combined 2-D PAGE, western blot analysis, N-terminal amino acid sequencing and liquid chromatography-mass spectrometry-mass spectrometry (LC-MS-MS) to develop a detailed map of culture filtrate proteins and have obtained the partial amino acid sequences for five previously undefined, relatively abundant proteins within this fraction which are found to be useful as early antigens for serodiagnosis of TB.

Additionally, a comparative analysis of 2-D PAGE maps of the CFP of three Mtb laboratory strains, H37Ra, H37Rv and Erdman, demonstrated only minor differences. The results reported below provide a detailed portrait of the protein profile of this newly appreciated immunologically important fraction and a spectrum of proteins to which proteins from clinical isolates of Mtb can be compared. The definition of these proteins as the major early antigens of TB recognized by circulating antibodies in TB patients early in the disease process is presented in Examples V and VIII, below.

A. Materials and Methods

1. Growth of Mtb and Preparation of Culture Filtrate Proteins

Mtb strains H37Rv (ATCC 27294) and H37Ra (ATCC 25177) were obtained from American Type Culture Collection (Manassas, Va.). Mtb strain Erdman (TMC 107) was obtained from the Trudeau Mycobacterial Collection. Initially, each Mtb strain was inoculated from a 1 ml frozen stock into 10 ml of glycerol alanine salts (GAS) media; three such cultures were prepared for each strain. After incubation at 37° C. for 14 days with gentle agitation each 10 ml culture was passed two more times increasing the volume of media by ten times for each pass. The resulting one liter cultures were termed pass number four. For each Mtb strain, three liters of pass number four cultures were used to inoculate 30 liters of GAS media. After 14 days of growth at 37° C. with gentle agitation, the culture supernatant was removed from the cells by filtration and the CFPs concentrated and processed as described. Protein content of the concentrated culture filtrate was quantitated by the bicinchoninic acid protein assay.

To establish growth curves for Mtb strains H37Ra, H37Rv, and Erdman, culture tubes (13 by 100 mm) containing 3 ml of GAS media with 0.05% Tween 80 were inoculated with actively growing Mtb cultures to an optical density of 0.1 at 600 nm. These cultures were incubated at 37° C. with stirring and optical densities at A600 were obtained every 12 hours for a 22 day period.

2. Antibodies

The mAbs IT-69 (HBT11) and IT-67 (L24.b4) were obtained from Dr. A. B. Andersen, Statens Seruminstitut, Copenhagen, Denmark. The mAb A3h4 was obtained from Drs. P. K. Das and A. Rambukana, University of Amsterdam, Amsterdam, The Netherlands and mAbs F126-2 and HYB 76-8 were obtained from Dr. A. Kolk, Royal Tropical Institute, Amsterdam, The Netherlands, and Dr. I. Rosenkrands, Statens Seruminstitut, Copenhagen, Denmark, respectively. All other mAbs were supplied through the WHO Monoclonal Antibody Bank then maintained by Dr. T. Shinnick, CDC, Atlanta, Ga. Anti-MPT63 polyclonal serum was provided by Dr. H. Wiker, University of Oslo, Norway. Dr. S, Nagai provided polyclonal sera specific for MPT 32, MPT 35, MPT 46, MPT 53, and MPT 57.

3. SDS-PAGE and 2-D PAGE of Culture Filtrate Proteins

Standard SDS-PAGE was performed under reducing conditions with gels (7.5×10 cm×0.75 mm) containing a 6% stack over a 15% resolving gel. Each gel was run at 10 mA for 15 min followed by 15 mA for 1.5 h.

2-D PAGE separation of proteins was achieved by the method of O'Farrell with minor modifications. Specifically, 70 µg of CFP was dried and suspended in 30 µl of isoelectric focusing (IEF) sample buffer (9M urea, 2% NP-40, 5% β-mercaptoethanol, and 5% ampholytes pH 3-10 (Pharmacia Biotech, Piscataway, N.J.)), and incubated for 3 h at 20° C. An aliquot of 25 µg of protein was applied to a 6% polyacrylamide IEF tube gel (1.5 mm by 6.5 cm) containing 5% Pharmalytes pH 3-10 and 4-6.5 in a ratio of 1:4. The proteins were focused for 3 h at 1 kV using 10 mM $H_3PO_4$ and 20 mM NaOH as the catholyte and anolyte, respectively. The tube gels were subsequently imbibed in sample transfer buffer for 30 min and placed on a preparative SDS-polyacrylamide gel (7.5×10 cm×1.5 mm) containing a 6% stack over a 15% resolving gel. Electrophoresis in the second dimension was carried out at 20 mA per gel for 0.3 h followed by 30 mA per gel for 1.8 h. Proteins were visualized by staining with silver nitrate.

4. Computer Aided Analysis of Two-Dimensional Gels

Silver stained 2-D PAGE gels were imaged using a cooled CCD digitizing camera and analyzed with MicroScan 1000 2-D Gel Analysis Software (Technology Resources, Inc., Nashville, Tenn.). Protein peak localization and analysis was conducted with the spot filter on, a minimum allowable peak height of 1.0, and minimum allowable peak area of 2.0.

5. Western Blot Analyses

Proteins, subjected to 2-D or SDS-PAGE, were transferred to nitrocellulose membranes (Schleicher and Schuell, Keene, N.H.) which were blocked with 0.1% bovine serum albumin in 0.05 M Tris-HCl, pH 7.5, 0.15 M NaCl, and 0.05% Tween 80 (TBST). These membranes were incubated for 2 h with specific antibodies diluted with TBST to the proper working concentrations (Table 2). After washing, the membranes were incubated for 1 h with goat anti-mouse or -rabbit alkaline phosphatase-conjugated antibody (Sigma) diluted in TBST. The substrates nitro-blue-tetrazolium and 5-bromo-4-chloro-3-indoyl phosphate (BCIP) were used for color development.

Mapping of proteins reactive to specific antibodies within the 2-D PAGE gel was accomplished using 0.1% India ink as a secondary stain for the total protein population after detection by immunoblotting. Alternatively, the Digoxigenin (DIG) Total Protein/Antigen Double Staining Kit (Boehringer Mannheim, Indianapolis, Ind.) was employed for those antibody-reactive proteins that could not be mapped using India ink as the secondary stain. Briefly, after electroblotting, the membranes were washed three times in 0.05 M $K_2HPO_4$, pH 8.5. The total protein population was conjugated to digoxigenin by incubating the membrane for one hour at room temperature in a solution of 0.05 M $K_2HPO_4$, pH 8.5 containing 0.3 ng/ml digoxigenin-3-O-methylcarbonyl-ε-amino-caproic acid N-hydroxysuccinimide ester and 0.01% Nonidet-P40. The membranes were subsequently blocked with a solution of 3% bovine serum albumin in 0.05 M Tris-HCl, pH 7.5, 0.15 M NaCl (TBS) for 1 h followed by washing with TBS. Incubation with specific antibodies was performed as described, followed by incubation of the membranes with mouse anti-DIG-Fab fragments conjugated to alkaline phosphatase diluted 1:2000 in TBS, for 1 h. The membranes were washed three times with TBS and probed with goat anti-mouse or -rabbit horse radish peroxidase-conjugated antibody. Color development for the proteins reacting to the specific anti-Mtb protein antibodies was obtained with the substrates 4-(1,4,7,10-tetraoxadecyl)-1-naphthol and 1.8% $H_2O_2$. Secondary color development of the total protein population labeled with digoxigenin utilized BCIP and [2-(4-iodophenyl)-3-(4-nitrophenyl)-5-phenyl-tetrazolium chloride] as the substrates.

6. Amino Acid Sequence Analysis

To obtain N-terminal amino acid sequence for selected proteins, CFPs (200 μg) were resolved by 2-D PAGE and transferred to polyvinylidene difluoride membrane (Millipore, Milford, Mass.) by electroblotting at 50 V for 1 h, using CAPS buffer with 10% methanol. The membrane was stained with 0.1% Coomassie brilliant blue in 10% acetic acid and destained with a solution of 50% methanol and 10% acetic acid. Immobilized proteins were subjected to automated Edman degradation on a gas phase sequencer equipped with a continuous-flow reactor. The phenylthiohydantoin amino acid derivatives were identified by on-line reversed-phase chromatography as described previously.

7. LC-MS-MS Analysis

Selected CFP were subjected to LC-MS-MS to determine the sequence of internal peptide fragments. CFPs (200 mg) were resolved by 2-D PAGE and the gel stained with 0.1% Coomassie brilliant blue and destained as described for proteins immobilized to PVDF membranes. The protein of interest was excised from the gel, washed several times with distilled water to remove residual acetic acid and subjected to in-gel proteolytic digestion with trypsin. Peptides were eluted from the acrylamide and separated by C18 capillary RP-HPLC. The microcapillary RP-HPLC effluent was introduced directly into a Finnigan-MAT (San Jose, Calif.) TSQ-700 triple sector quadrupole mass spectrometer. Mass spectrometry and analysis of the data was performed as described by Blyn et al.

C. Results

1. Definition of Proteins Present in the Culture Filtrate of Mtb H37Rv.

Through the efforts of the World Health Organization (WHO) Scientific Working Groups (SWGs) on the Immunology of Leprosy (IMMLEP) and Immunology of Tuberculosis (IMMTUB) an extensive collection of mAbs against mycobacterial proteins has been established. This library as well as mAbs and polyclonal sera not included in these collections allowed for the identification of known mycobacterial proteins in the culture filtrate of Mtb. A detailed search of the literature identified mAbs and/or polyclonal sera reactive against 35 individual Mtb CFP (Table 2). Initially, the presence or absence of these proteins in the culture filtrate of Mtb H37Rv, prepared for these studies, was determined by Western blot analyses. Of the antibodies and sera tested, all but one (IT-56) demonstrated reactivity to specific proteins of this preparation (Table 2). The mAb IT-56 is specific for the 65 kDa Mtb GroEL homologue; a protein primarily associated with the cytosol. Additionally the mAb IT-7 reacted with a 14 kDa and not a 40 kDa CFP.

2. 2-D PAGE Mapping of Known CFP of Mtb H37Rv

Using 2-D western blot analysis coupled with secondary staining (either India ink or Dig total protein/antigen double staining) the proteins reactive to specific mAbs or polyclonal sera were mapped within the 2-D PAGE profile of CFP of Mtb H37Rv. In all, 32 of the reactive antibodies detected specific proteins resolved by 2-D PAGE (Table 2). However, two antibodies (IT-1 and IT-46), that were reactive by conventional western blot analysis, failed to detect any protein within the 2-D profile (Table 2) presumably due to the absence of linear epitopes exposed by the denaturing conditions used to resolve the molecules.

The majority of the antibodies recognized a single protein spot. However, several (IT-3, IT-4, IT-7, IT-20, IT-23, IT-41, IT-42, IT-44, IT-49, IT-57, IT-58, IT-61 and MPT 32) reacted with multiple proteins. Five of these, IT-23, IT-42, IT-44, IT-57 and IT-58 reacted with protein clusters centered at 36 kDa, 85 kDa, 31 kDa, 85 kDa and 50 kDa, respectively. Additionally the proteins in each of these clusters migrated within a narrow pI range; suggesting that the antibodies were reacting with multiple isoforms of their respective proteins. In the case of the protein cluster at 85 kDa (which includes "88 kDa" GlcB early antigen of this invention) detected by IT-57, the most dominant component was also recognized by IT-42.

Polyclonal sera against MPT 32 recognized a 45 and 42 kDa protein of relatively similar pI. While defining sites of glycosylation on MPT 32 (see above) we observed that this protein was prone to autoproteolysis and formed a 42 kDa product. Thus, the 42 kDa protein detected with the anti-MPT 32 sera was a breakdown product of the 45 kDa MPT 32 glycoprotein. The mAb (T-49 specific for the Antigen 85 (Ag85) complex clearly identified the three gene products (Ag85A, B and C) of this complex. The greatest region of antibody cross-reactivity was at molecular masses below 16 kDa. The most prominent protein in this region reacted with mAb IT-3 specific for the 14 kDa GroES homolog. This mAb also recognized several adjacent proteins at approximately 14 kDa. Interestingly, various members of this same protein cluster reacted with anti-MPT 57 and anti-MPT 46 polyclonal sera, and the mAbs IT-4, IT-7, and IT-20.

3. N-Terminal Amino Acid Sequencing of Selected CFPs

The N-terminal amino acid sequences or complete gene sequences and functions of several of the CFPs of Mtb, mapped with the available antibodies, are known. However, such information is lacking for the proteins that reacted with IT-42 IT-43, IT-44, IT-45, IT-51, IT-52, IT-53, IT-57, IT-59 and IT-69, as well as several dominant proteins not identified by these means. Of these, the most abundant proteins (IT-52, IT-57, IT 42, IT-58 and proteins labeled A-K) were selected and subjected to N-terminal amino acid sequencing (Table 3).

Three of these proteins were found to correspond to previously defined products. The N-terminal amino acid sequence of the protein labeled D was identical to that of Ag85 B and C. This result was unexpected given that the IT-49 mAb failed to detect this protein and N-terminal amino acid analysis confirmed that those proteins reacting with IT-49 were members of the Ag85 complex. Second, the protein labeled E had an N-terminal sequence identical to that of glutamine synthetase. A third protein which reacted with IT-52 was found to be identical to MPT 51.

However, five of the proteins analyzed appeared to be novel. Three of these, those labeled B, C and IT-58 did not demonstrate significant homology to any known mycobacterial or prokaryotic sequences. The protein labeled I possessed an N-terminal sequence with 72% identity to the amino terminus of an α-hydroxysteroid dehydrogenase from a *Eubacterium* species, and the protein labeled F was homologous to a deduced amino acid sequence for an open reading frame identified in the Mtb cosmid MTCY1A11.

TABLE 2

Reactivity of CFPs of *M. tuberculosis* $H_{37}Rv$
to reported specific mAbs and polyclonal antisera

| Antibody[1] | MW (kDa) | Dilution Used | REACTIVITY 1-D | 2-D |
|---|---|---|---|---|
| IT-1 (F23-49-7) | 16 kDa | 1:2000 | + | − |
| IT-3 (SA-12) | 12 kDa | 1:8000 | + | + |
| IT-4 (F24-2-3) | 16 kDa | 1:2000 | + | + |
| IT-7 (F29-29-7) | 40 kDa | 1:1000 | + | + |
| IT-10 (F29-47-3) | 21 kDa | 1:1000 | + | + |
| IT-12 (HYT6) | 17-19 kDa | 1:50 | + | + |
| IT-17 (D2D) | 23 kDa | 1:8000 | + | + |
| IT-20 (WTB68-A1) | 14 kDa | 1:250 | + | + |
| IT-23 (WTB71-H3) | 38 kDa | 1:250 | + | + |
| IT-40 (HAT1) | 71 kDa | 1:50 | + | + |
| IT-41 (HAT3) | 71 kDa | 1:50 | + | + |
| IT-42 (HBT1) | 82 kDa | 1:50 | + | + |
| IT-43 (HBT3) | 56 kDa | 1:50 | + | + |
| IT-44 (HBT7) | 32 kDa | 1:50 | + | + |
| IT-45 (HBT8) | 96 kDa | 1:50 | + | + |
| IT-46 (HBT10) | 40 kDa | 1:50 | + | − |
| IT-49 (HYT27) | 32-33 kDa | 1:50 | + | + |
| IT-51 (HBT2) | 17 kDa | 1:50 | + | + |
| IT-52 (HBT4) | 25 kDa | 1:50 | + | + |
| IT-53 (HBT5) | 96 kDa | 1:50 | + | + |
| IT-56 (CBA1) | 65 kDa | 1:50 | − | ND* |
| IT-57 (CBA4) | 82 kDa | 1:50 | + | + |
| IT-58 (CBA5) | 47 kDa | 1:50 | + | + |
| IT-59 (F67-1) | 33 kDa | 1:100 | + | + |
| IT-61 (F116-5) | 30 (24) kDa | 1:100 | + | + |
| IT-67 (L24.b4) | 24 kDa | 1:50 | + | + |
| IT-69 (HBT 11) | 20 kDa | 1:6 | + | + |
| F126-2 | 30 kDa | 1:100 | + | + |
| A3h4 | 27 kDa | 1:50 | + | + |
| HYB 76-8 | 6 kDa | 1:100 | + | + |
| anti-MPT 32 | 50 kDa | 1:100 | + | + |
| anti-MPT 46 | 10 kDa | 1:100 | + | + |
| anti-MPT 53 | 15 kDa | 1:100 | + | + |
| anti-MPT 57 | 12 kDa | 1:100 | + | + |
| anti-MPT 63 - K64 | 18 kDa | 1:200 | + | + |

*ND: Not done
[1]Original designations for the World Health Organization cataloged Mab are given in parentheses.

Examples I and II show that a high molecular weight fraction of CFP of Mtb reacted with a preponderance of sera from TB patients and that this fraction was distinguished from other native fractions in that it possessed the product reactive to mAb IT-57. In view of this, the protein cluster (including the 88 kDa protein GlcB) defined by IT-42 and IT-57 was excised from a 2-D polyacrylamide gel, digested with trypsin and the resulting peptides analyzed by LC-MS-MS. Ten of the peptides from the digest yielded molecular masses and fragmentation patterns consistent with those predicted for tryptic fragments of the Mtb katG-encoded catalase/peroxidase (Table 3). Hence, the portion of the protein not reactive with IT 57 appears to be the katG product. However, the IT 57-reactive part of the 88 kDa protein cluster did not have sequence homology (following LC-MS-MS analysis) to an identified Mtb protein.

TABLE 3

N-terminal amino acid sequences or internal peptide fragments identified by LC-MS-MS of selected CFPs of *M. tuberculosis* $H_{37}Rv$.

| Protein | N-terminal AA Sequence | SEQ ID | Homology |
|---|---|---|---|
| A | None[1] | | |
| B | APPSCAGLD/GCTV | 56 | |
| C | XXAVXVT | 57 | |
| D | FSRPGLPVEYLQVPSP | 58 | Mtb Antigen 85 A and C |
| E | TEKTPDDVFKLADDEKVEYVD | 59 | Mtb Glutamine synthetase |
| F | XPVM/LVXPGXEXXQDN | 60 | Mtb cosmid MTCY1A11 |
| G | None[1] | | |
| H | None[1] | | |

TABLE 3-continued

N-terminal amino acid sequences or internal peptide fragments identified by LC-MS-MS of selected CFPs of *M. tuberculosis* H₃₇Rv.

| | | | |
|---|---|---|---|
| I | XVYDVIMLTAGP | 61 | *Eubacterium* sp. VPI 12708 α-hydroxysteroid dehydrogenase |
| J | None[1] | | |
| K | None[1] | | |
| IT-43 | None[1] | | |
| IT-52 | APYENLMVP | 62 | Mtb MPT 51 |
| IT-58 | K/NVIRIXGXTD | 63 | |
| F126-2 | None[1] | | |

| Protein | INTERNAL PEPTIDES MAPPED | | SEQ ID | HOMOLOGY |
|---|---|---|---|---|
| IT-42 | FAPLNSWPDNASLDK | (129-143) | 64 | *M t.* catalase/peroxidase |
| | EATWLGDER | (201-209) | 65 | |
| | DAITSGIEVVWTNTPTK | (311-327) | 66 | |
| | SPAGAWQYTAK | (346-356) | 67 | |
| | DGAGAGTIPDPFGGPGR | (357-373) | 68 | |
| | RWLEHPEELADEFAK | (396-410) | 69 | |
| | TLEEIQESFNSAAPGNIK | (519-536) | 70 | |
| | AGHNITVPFTPGR | (556-569) | 71 | |
| | TDASQEQTDVESFAVLEPK | (569-588) | 72 | |
| | GNPLPAEYMLLDK | (599-611) | 73 | |
| | ANLLTLSAPEMTVLVGGLR | (612-630) | 74 | |
| | VDLVFGSNSELR | (692-703) | 75 | |
| | ALVEVYGADDAQPKF | (704-718) | 76 | |

[1]"None" indicates that proteins were refractory to sequencing by Edman degradation.

TABLE 4

Summary of Protein Spots Detected by Computer-aided Analysis of Silver Nitrate Stained 2-D Gels

| Ref #. | H37Rv | H37Ra | Erdman | MW(kDa) | pI | Antibody Reactivity | Function/ Designation | N-terminal Sequence[1] | SEQ ID NO |
|---|---|---|---|---|---|---|---|---|---|
| 1 | 1 | 1 | 1 | 22.39 | ≧3 | | | | |
| 2 | 2 | 2 | 2 | 17.18 | ≧3 | | | | |
| 3 | 3 | 3 | 3 | 13.72 | ≧3 | | | | |
| 4 | 4 | 4 | 4 | 11.75 | ≧3 | | | | |
| 5 | 5 | 5 | 5 | 23.99 | 3.09 | | | | |
| 6 | 6 | 6 | 6 | 16.98 | 3.45 | | | | |
| 7 | 7 | 7 | 7 | 11.75 | 3.52 | HYB 76-8 | ESAT 6 | TEQQWDFAGI | 77 |
| 8 | 8 | 8 | NM | 27.23 | 3.63 | | | | |
| 9 | 9 | NM | NM | 20.30 | 3.82 | | | | |
| 10 | 10 | 10 | 10 | 21.63 | 4.14 | | IT-69 | | |

TABLE 4-continued

Summary of Protein Spots Detected by Computer-aided Analysis of Silver Nitrate Stained 2-D Gels

| Ref #. | H37Rv | H37Ra | Erdman | MW(kDa) | pI | Antibody Reactivity | Function/ Designation | N-terminal Sequence[1] | SEQ ID NO |
|---|---|---|---|---|---|---|---|---|---|
| 11 | 11 | 11 | 11 | 38.90 | 4.31 | anti-MPT 32 | MPT 32 | DPAPAPPVPT | 78 |
| 12 | 12 | 12 | 12 | 20.07 | 4.31 | IT-51 | | | |
| 13 | 13 | 13 | 13 | 13.49 | 14.46 | | | | |
| 14 | 14 | 14 | 14 | 42.17 | 4.51 | anti-MPT 32 | MPT 32 | DPALPAPPVPT | 78 |
| 15 | 15 | 15 | 15 | 31.44 | 4.53 | | | | |
| 16 | 16 | 16 | 16 | 32.36 | 4.55 | | | | |
| 17 | 17 | 17 | 17 | 11.61 | 4.55 | | | | |
| 18 | 18 | 18 | 18 | 35.48 | 4.62 | | | | |
| 19 | 19 | 19 | 19 | 25.85 | 4.65 | | | | |
| 20 | 20 | 20 | 20 | 21.38 | 4.68 | | | | |
| 21 | 21 | 21 | 21 | 19.72 | 4.69 | | | | |
| 22 | 22 | 22 | 22 | 31.44 | 4.75 | IT-44 | | | |
| 23 | 23 | 23 | 23 | 13.57 | 4.76 | | | | |
| 24 | 24 | 24 | 24 | 48.70 | 4.79 | | | | |
| 25 | 25 | 25 | 25 | 32.55 | 4.79 | IT-44 | | | |
| 26 | 26 | 26 | 26 | 15.67 | 4.79 | anti-MPT 53 | MPT 53 | DECIQ | 79 |
| 27 | 27 | 27 | 27 | 22.26 | 4.81 | | | | |
| 28 | 28 | 28 | 28 | 28.35 | 4.83 | | | | |
| 29 | 29 | 29 | 29 | 26.15 | 4.83 | IT-67 | MPT64 | RIKIF | 80 |
| 30 | 30 | 30 | 30 | 23.58 | 4.84 | | | | |
| 31 | 31 | 31 | 31 | 16.88 | 4.84 | anti-MPT 63 | MPT63 | AYPITGKLGSELT | 81 |
| 32 | 32 | 32 | 32 | 38.02 | 4.87 | | | | |
| 33 | 33 | 33 | 33 | 29.85 | 4.87 | | | | |
| 34 | 34 | 34 | 34 | 19.05 | 4.88 | | | | |
| 35 | 35 | 35 | 35 | 22.26 | 4.92 | | | | |
| 36 | 36 | 36 | 36 | 35.08 | 4.93 | | | | |
| 37 | 37 | 37 | 37 | 31.44 | 4.93 | IT44/F126-2 | | | |
| 38 | 38 | 38 | 38 | 14.45 | 4.93 | anti-MPT 57/IT-3 | GroES homolog MPT 57 | MAKVNIKPLE | 82 |
| 39 | 39 | 39 | NM | 20.87 | 4.99 | | | | |
| 40 | 40 | 40 | 40 | 28.67 | 5.00 | | | | |
| 41 | 41 | 41 | 41 | 18.62 | 5.00 | | | | |
| 42 | 42 | 42 | 42 | 19.50 | 5.00 | | | | |
| 43 | 43 | 43 | 43 | 40.74 | 5.02 | | | | |
| 44 | 44 | 44 | 44 | 29.68 | 5.02 | | | | |
| 45 | 45 | 45 | 45 | 14.96 | 5.02 | IT-3/4/7/20 | | | |
| 46 | 46 | 46 | 46 | 35.48 | 5.03 | IT-23 | PstS | CGSKPPSPET | 83 |

TABLE 4-continued

Summary of Protein Spots Detected by Computer-aided Analysis of Silver Nitrate Stained 2-D Gels

| Ref #. | H37Rv | H37Ra | Erdman | MW(kDa) | pI | Antibody Reactivity | Function/ Designation | N-terminal Sequence[1] | SEQ ID NO |
|---|---|---|---|---|---|---|---|---|---|
| 47 | 47 | 47 | 47 | 32.36 | 5.04 | | | | |
| 48 | 48 | 48 | 48 | 28.35 | 5.04 | | | | |
| 49 | 49 | 49 | 49 | 26.00 | 5.04 | | | | |
| 50 | 50 | 50 | 50 | 17.78 | 5.04 | | | | |
| 51 | 51 | 51 | 51 | 46.51 | 5.05 | | | | |
| 52 | 52 | 52 | 52 | 35.89 | 5.06 | IT-23 | PstS | CGSKPPSPET | 84 |
| 53 | 53 | 53 | 53 | 60.60 | 5.06 | | | | |
| 54 | 54 | 54 | 54 | 22.78 | 5.06 | | | | |
| 55 | 55 | 55 | 55 | 47.32 | 5.07 | | | | |
| 56 | 56 | 56 | 56 | 20.18 | 5.07 | | A | | |
| 57 | 57 | 57 | 57 | 31.62 | 5.08 | | | | |
| 58 | 58 | 58 | 58 | 18.62 | 5.08 | | | | |
| 59 | 59 | 59 | 59 | 29.68 | 5.08 | | | | |
| 60 | 60 | 60 | 60 | 14.54 | 5.09 | anti-MPT 46 IT-3/4/7/20 | MPT46 | RDSEK | 85 |
| 61 | 61 | 61 | 61 | 47.86 | 5.09 | | | | |
| 62 | 62 | 62 | NM | 31.26 | 5.09 | | | | |
| 63 | 63 | 63 | 63 | 25.56 | 5.09 | | | | |
| 64 | 64 | 64 | 64 | 13.11 | 5.09 | | | | |
| 65 | 65 | 65 | 65 | 72.86 | 5.09 | IT-40/IT-41 | DnaK homolog | MARAVGIDLG | 86 |
| 66 | 66 | 66 | 66 | 35.69 | 5.09 | IT-23 | PstS | CGSKPPSPET | 87 |
| 67 | 67 | 67 | 67 | 28.84 | 5.09 | | | | |
| 68 | 68 | 68 | 68 | 42.41 | 5.10 | | | | |
| 69 | 69 | 69 | 69 | 30.20 | 5.10 | | | | |
| 70 | 70 | 70 | 70 | 57.54 | 5.10 | | | | |
| 71 | 71 | 71 | NM | 31.62 | 5.10 | | | | |
| 72 | 72 | 72 | 72 | 47.86 | 5.10 | | | | |
| 73 | 73 | 73 | 73 | 38.46 | 5.10 | | | | |
| 74 | 74 | 74 | 74 | 25.56 | 5.10 | | B | *APPSCAGLD/GCTV* | 88 |
| 75 | 75 | 75 | 75 | 22.00 | 5.10 | | | | |
| 76 | 76 | 76 | 76 | 19.61 | 5.10 | IT-12 | 19 kDa lipoprotein | CSSNKSTTG | 89 |
| 77 | 77 | 77 | 77 | 28.18 | 5.10 | | | | |
| 78 | 78 | 78 | 78 | 79.43 | 5.10 | | | | |
| 79 | 79 | 79 | 79 | 66.83 | 5.10 | IT-41 | DnaK homolog | MARAVGIDLG | 90 |
| 80 | 80 | 80 | 80 | 42.17 | 5.10 | | C | *XXAVXVT* | 91 |
| 81 | 81 | 81 | 81 | 29.85 | 5.10 | IT-49/ IT-61 | Antigen 85 B/MPT 59 | FSRPGLPVEY | 92 |

TABLE 4-continued

Summary of Protein Spots Detected by Computer-aided Analysis of Silver Nitrate Stained 2-D Gels

| Ref #. | H37Rv | H37Ra | Erdman | MW(kDa) | pI | Antibody Reactivity | Function/ Designation | N-terminal Sequence[1] | SEQ ID NO |
|---|---|---|---|---|---|---|---|---|---|
| 82 | 82 | 82 | 82 | 49.55 | 5.10 | IT-58 | | K/NVIRIXGXTD | 93 |
| 83 | 83 | 83 | 83 | 32.17 | 5.10 | | | | |
| 84 | 84 | 84 | 84 | 38.46 | 5.11 | | | | |
| 85 | 85 | 85 | 85 | 34.47 | 5.11 | | | | |
| 86 | 86 | 86 | 86 | 58.88 | 5.11 | | | | |
| 87 | 87 | 87 | 87 | 20.89 | 5.11 | IT-10 | | | |
| 88 | 88 | 88 | 88 | 23.04 | 5.11 | | | | |
| 89 | 89 | 89 | 89 | 24.27 | 5.11 | | | | |
| 90 | 90 | 90 | 90 | 42.17 | 5.11 | | | | |
| 91 | 91 | 91 | 91 | 29.17 | 5.11 | | | | |
| 92 | 92 | 92 | 92 | 69.98 | 5.11 | IT-41 | DnaK homolog | MARAVGIDLGT | 94 |
| 93 | 93 | 93 | 93 | 26.15 | 5.11 | A3h4 | | | |
| 94 | 94 | 94 | 94 | 25.12 | 5.11 | | | | |
| 95 | 95 | 95 | 95 | 27.86 | 5.11 | | | | |
| 96 | 96 | 96 | 96 | 56.23 | 5.11 | | | | |
| 97 | 97 | 97 | 97 | 15.22 | 5.11 | IT-3/7 | | | |
| 98 | 98 | 98 | 98 | 29.17 | 5.11 | | | | |
| 99 | 99 | 99 | 99 | 106.05 | 5.12 | | | | |
| 100 | 100 | 100 | 100 | 93.33 | 5.12 | | | | |
| 101 | 101 | 101 | 101 | 82.22 | 5.12 | | | | |
| 102 | 102 | 102 | 102 | 32.73 | 5.12 | IT-59 | | | |
| 103 | 103 | 103 | 103 | 31.08 | 5.12 | | D: Antigen 85 Homolog? | FSRPGLPVEYLQVP SP | 95 |
| 104 | 104 | 104 | 104 | 38.90 | 5.12 | | | | |
| 105 | 105 | 105 | 105 | 58.88 | 5.12 | | | | |
| 106 | 106 | 106 | 106 | 44.41 | 5.12 | | | | |
| 107 | 107 | 107 | 107 | 34.67 | 5.12 | | | | |
| 108 | 108 | 108 | NM | 26.61 | 5.12 | | | | |
| 109 | 109 | 109 | 109 | 20.54 | 5.12 | | | | |
| 110 | 110 | 110 | 110 | 38.90 | 5.13 | | | | |
| 111 | 111 | 111 | 111 | 104.71 | 5.13 | | | | |
| 112 | 112 | 112 | 112 | 66.83 | 5.13 | | | | |
| 113 | 113 | 113 | 113 | 85.11 | 5.14 | | | | |
| 114 | 114 | 114 | 114 | 55.59 | 5.14 | | E: Glutamine synthetase | TEKTPDDVFKLAK DEKVEYVD | 96 |
| 115 | 115 | 115 | 115 | 42.41 | 5.14 | | | | |
| 116 | 116 | 116 | 116 | 26.45 | 5.15 | | | | |
| 117 | 117 | 117 | 117 | 42.17 | 5.17 | | | | |

TABLE 4-continued

Summary of Protein Spots Detected by Computer-
aided Analysis of Silver Nitrate Stained 2-D Gels

| Ref #. | H37Rv | H37Ra | Erdman | MW(kDa) | pI | Antibody Reactivity | Function/ Designation | N-terminal Sequence[1] | SEQ ID NO |
|---|---|---|---|---|---|---|---|---|---|
| 118 | 118 | 118 | 118 | 34.28 | 5.17 | | | | |
| 119 | 119 | 119 | 119 | 31.08 | 5.17 | IT-49 | Antigen 85 C/MLPT 45 | FSRPGLPVEY | 97 |
| 120 | 120 | 120 | 120 | 55.59 | 5.17 | | E: Glutamine synthetase | TEKTPDDVFKLDE VE/T | 98 |
| 121 | 121 | 121 | NM | 25.70 | 5.17 | | | | |
| 122 | 122 | 122 | 122 | 45.71 | 5.18 | | | | |
| 123 | 123 | NM | NM | 20.65 | 5.18 | | | | |
| 124 | 124 | 124 | 124 | 85.11 | 5.19 | IT-42/IT-57 | Catalase/Peroxidase | MPEQHPPITE | 99 |
| 125 | 125 | 125 | 125 | 16.03 | 5.19 | | | | |
| 126 | 126 | 126 | 126 | 39.81 | 5.20 | | | | |
| 127 | 127 | 127 | 127 | 36.94 | 5.21 | | | | |
| 128 | 128 | 128 | 128 | 46.24 | 5.22 | | | | |
| 129 | 129 | 129 | 129 | 27.23 | 5.22 | | | | |
| 130 | 130 | 130 | 130 | 51.29 | 5.22 | | | | |
| 131 | 131 | 131 | 131 | 19.61 | 5.22 | | | | |
| 132 | 132 | 132 | 132 | 42.41 | 5.24 | | | | |
| 133 | 133 | 133 | 133 | 38.02 | 5.24 | | | | |
| 134 | 134 | 134 | 134 | 20.89 | 5.24 | | | | |
| 135 | 135 | 135 | 135 | 46.24 | 5.26 | | | | |
| 136 | 136 | 136 | 136 | 35.48 | 5.26 | | | | |
| 137 | 137 | 137 | 137 | 30.73 | 5.26 | | | | |
| 138 | 138 | 138 | NM | 13.49 | 5.27 | | | | |
| 139 | 139 | 139 | 139 | 31.62 | 5.28 | | | | |
| 140 | 140 | 140 | 140 | 29.17 | 5.30 | | | | |
| 141 | 141 | 141 | 141 | 38.46 | 5.33 | | | | |
| 142 | 142 | 142 | 142 | 42.41 | 5.34 | | | | |
| 143 | 143 | 143 | 143 | 33.50 | 5.34 | | | | |
| 144 | 144 | 144 | 144 | 24.97 | 5.34 | | F | XPVM/LVXPGXEXX QDN | 100 |
| 145 | 145 | 145 | 145 | 22.65 | 5.34 | | | | |
| 146 | 146 | 146 | 146 | 50.12 | 5.35 | | | | |
| 147 | 147 | 147 | 147 | 26.92 | 5.37 | | G | | |
| 148 | 148 | 148 | 148 | 15.67 | 5.37 | | | | |
| 149 | 149 | 149 | 149 | 31.44 | 5.38 | IT-49 | Antigen 85 A/MPT 44 | FSRPGLPVEY | 101 |
| 150 | 150 | 150 | 150 | 69.18 | 5.39 | | | | |
| 151 | 151 | NM | 151 | 94.41 | 5.40 | IT-45 | | | |

TABLE 4-continued

Summary of Protein Spots Detected by Computer-aided Analysis of Silver Nitrate Stained 2-D Gels

| Ref #. | H37Rv | H37Ra | Erdman | MW(kDa) | pI | Antibody Reactivity | Function/ Designation | N-terminal Sequence[1] | SEQ ID NO |
|---|---|---|---|---|---|---|---|---|---|
| 152 | 152 | 152 | 152 | 35.89 | 5.45 | | | | |
| 153 | 153 | 153 | 153 | 21.13 | 5.47 | | | | |
| 154 | 154 | 154 | 154 | 20.07 | 5.47 | | H | | |
| 155 | 155 | 155 | 155 | 58.88 | 5.50 | IT-43 | | | |
| 156 | 156 | 156 | 156 | 48.70 | 5.53 | | | | |
| 157 | 157 | 157 | 157 | 82.22 | 5.61 | | | | |
| 158 | 158 | 158 | 158 | 53.70 | 5.61 | | | | |
| 159 | 159 | 159 | 159 | 34.67 | 5.68 | | | | |
| 160 | 160 | 160 | 160 | 57.54 | 5.70 | | | | |
| 161 | 161 | 161 | 161 | 79.43 | 5.74 | | | | |
| 162 | 162 | 162 | 162 | 31.99 | 5.76 | | | | |
| 163 | 163 | 163 | 163 | 29.17 | 5.80 | | | | |
| 164 | 164 | 164 | 164 | 27.86 | 5.80 | | | | |
| 165 | 165 | 165 | 165 | 52.48 | 5.86 | | | | |
| 166 | 166 | 166 | 166 | 45.71 | 5.86 | | | | |
| 167 | 167 | 167 | 167 | 33.11 | 5.86 | | | | |
| 168 | 168 | 168 | 168 | 58.88 | 5.88 | | | | |
| 169 | 169 | 169 | 169 | 25.85 | 5.88 | | | | |
| 170 | 170 | 170 | 170 | 26.92 | 5.91 | IT-52 | MPT 51 | APYENLMVPS | 102 |
| 171 | 171 | 171 | 171 | 22.13 | 5.93 | | | | |
| 172 | 172 | 172 | 172 | 34.67 | 5.98 | | | | |
| 173 | 173 | 173 | 173 | 31.81 | 5.98 | | | | |
| 174 | 174 | 174 | 174 | 56.23 | 6.02 | | | | |
| 175 | 175 | 175 | 175 | 98.86 | 6.08 | IT-53 | | | |
| 176 | 176 | 176 | 176 | 52.48 | 6.18 | | I | XVYDVIMLTAGP | 103 |
| 177 | 177 | 177 | 177 | 42.17 | 6.18 | | | | |
| 178 | 178 | 178 | 178 | 26.61 | 6.33 | | | | |
| 179 | 179 | 179 | 179 | 45.19 | 6.36 | | | | |
| 180 | 180 | 180 | 180 | 30.90 | 6.39 | | | | |
| 181 | 181 | 181 | 181 | 34.47 | 6.42 | | J | | |
| 182 | 182 | 182 | 182 | 24.83 | 6.42 | | | | |
| 183 | 183 | 183 | 183 | 18.20 | 6.49 | | | | |
| 184 | 184 | 184 | 184 | 38.02 | 6.55 | | | | |
| 185 | 185 | 185 | 185 | 41.93 | 6.73 | | | | |
| 186 | 186 | 186 | 186 | 25.41 | 6.88 | | | | |
| 187 | 187 | 187 | 187 | 133.35 | 7.00 | | | | |
| 188 | 188 | 188 | 188 | 30.20 | 7.17 | | | | |

TABLE 4-continued

Summary of Protein Spots Detected by Computer-aided Analysis of Silver Nitrate Stained 2-D Gels

| Ref #. | H37Rv | H37Ra | Erdman | MW(kDa) | pI | Antibody Reactivity | Function/ Designation | N-terminal Sequence[1] | SEQ ID NO |
|---|---|---|---|---|---|---|---|---|---|
| 189 | 189 | 189 | 189 | 33.50 | 7.30 | | | | |
| 190 | 190 | 190 | 190 | 24.97 | 7.39 | | | | |
| 191 | 191 | 191 | NM | 27.38 | 7.58 | | | | |
| 192 | 192 | 192 | 192 | 40.74 | 8.39 | | K | | |
| 193 | 193 | 193 | 193 | 20.54 | 9.64 | | | | |
| 194 | 194 | 194 | 194 | 41.93 | 10.33 | | | | |
| 195 | 195 | 195 | 195 | 24.97 | 10.41 | | | | |
| 196 | 196 | 196 | 196 | 32.73 | 10.74 | | | | |
| 197 | 197 | 197 | NM | 27.23 | ≦10 | | | | |
| 198 | 198 | 198 | 198 | 50.12 | ≦10 | | | | |
| 199 | 199 | 199 | NM | 38.90 | ≦10 | | | | |
| 200 | 200 | 200 | 200 | 29.68 | ≦10 | | | | |
| 201 | 201 | 201 | 201 | 24.83 | ≦10 | IT-17/ IT-61 | Superoxide dismutase/MPT 58 | MAEYTLPDLD | 104 |
| 202 | 202 | 202 | NM | 60.60 | ≦10 | | | | |
| 203 | 203 | NM | NM | 42.17 | ≦10 | | | | |
| 204 | 204 | 204 | NM | 48.70 | ≦10 | | | | |
| 205 | 205 | 205 | 205 | 38.90 | ≦10 | | | | |
| 206 | NM | 206 | NM | 20.87 | 4.83 | | | | |
| 207 | NM | 207 | NM | 20.40 | 4.79 | | | | |
| 208 | NM | 208 | NM | 15.67 | 5.02 | | | | |
| 209 | NM | 209 | NM | 22.61 | 5.11 | | | | |
| 210 | NM | 210 | 210 | 19.05 | 5.11 | | | | |
| 211 | NM | NM | 211 | 38.95 | 4.93 | | | | |
| 212 | NM | NM | 212 | 59.10 | 5.04 | | | | |
| 213 | NM | NM | 213 | 57.54 | 5.10 | | | | |
| 214 | NM | NM | 214 | 25.85 | 5.22 | | | | |
| 215 | NM | NM | 215 | 26.15 | 5.24 | | | | |
| 216 | NM | NM | 216 | 46.24 | 5.35 | | | | |
| 217 | NM | NM | 217 | 48.70 | 5.40 | | | | |
| 218 | NM | NM | 218 | 53.70 | 5.43 | | | | |
| 219 | NM | NM | 219 | 59.10 | 6.42 | | | | |
| 220 | NM | NM | 220 | 15.80 | 6.90 | | | | |
| 221 | NM | NM | 221 | 32.36 | 9.00 | | | | |
| 222 | NM | NM | 222 | 94.35 | 9.30 | | | | |

[1]N-terminal sequences obtained by present inventors are in italics.

4. Comparative CFP Profiles of Mtb Strains H37Rv, H37Ra and Erdman

Comparative 2-D PAGE analysis of CFPs from three Mtb type strains (H37Rv, H37Ra and Erdman) was performed to identify possible qualitative differences in their protein compositions. Initially, three separate lots of H37Rv CFP were pooled and resolved by 2-D PAGE. The silver stained gel was digitized and the data analyzed using the Microscan 1000 2-D gel analysis software. In all, 205H37Rv protein spots were detected and individual proteins were numbered sequentially from acidic to basic pI and by descending molecular weight (Table 4). Similar maps generated for the CFP of H37Ra and Erdman strains resulted in the recognition of 206 and 203 protein spots, respectively (Table 4). Alignment of these three maps, using the 2-D main software, revealed a striking similarity between these three culture filtrate preparations. The protein spots of H37Ra and Erdman culture filtrate that matched those of the H37Rv culture filtrate were given identical numbers, and proteins characteristic of the H37Ra or Erdman strains were assigned original numbers (Table 4). Proteins present only in one or two of the type strains were relatively minor components of the culture filtrates.

C. Discussion

In contrast to Mtb cell wall, cell membrane and cytoplasmic proteins, the CFPs are well*** defined in terms of function, immunogenicity and composition. However, a detailed analysis of the total proteins, and the molecular definition and 2-D PAGE mapping of the majority of these CFPs has not been performed. Nagai and colleagues identified and mapped by 2-D PAGE the most abundant proteins filtrate harvested after five weeks of culture in Sauton medium. The present study used culture filtrates from mid- to late-logarithmic cultures of three Mtb type strains H37Ra, H37Rv, and Erdman to provide for the first time a detailed analysis understanding of this widely studied fraction.

Computer analysis of the 2-D gels of CFP resolved 205, 203 and 206 individual protein spots from filtrates of strains H37Rv, H37Ra and Erdman, respectively. Of the total spots, 37 were identified using a collection of mAb and polyclonal sera against CFPs. Several of these antibodies recognized more than one spot; several are believed to react with multiple isoforms of the same protein or were previously shown to recognize more then a single gene product. In all, partial or complete amino acid sequences have been reported for 17 of the proteins mapped with the available antibodies (see Table 4).

For greater molecular definition, a number of abundant products observed in the 2-D PAGE were subjected to N-terminal sequence analysis.

One such protein that migrated between Ag85B and Ag85C was found to have 16 residues (FSRPGLPVEY-LQVPSP, [SEQ ID NO:95]) identical to the N-terminus of mature Ag85A and Ag85B, and different from Ag85C by a single residue (position 15). This protein spot was apparently merely a homologue of Ag85A or B. However, its complete lack of reactivity with an Ag85-specific mAb (IT-49), its weight greater than that of Ag85B and its shift in pI in relation to Ag85A suggested that this product may have resulted from post translational modifications. Alternatively, this protein may be a yet unrecognized fourth member of the Ag85 complex. However, members of the Ag85 complex appear to lack post-translational modifications in some reports whereas others report several bands corresponding to Ag85C after isoelectric focusing. However, no direct evidence supports the existence of a fourth Ag85 product.

A second product sequenced was a 25 kDa protein with a pI of 5.34. Its N-terminal sequence (XPVM/LVXPGXEXX-QDN, [SEQ ID NO:100]) showed homology to an internal fragment (DPVLVFPGMEIRQDN, [SEQ ID NO:105]) corresponding to open reading frame 28c of the Mtb cosmid MTCY1A11. Analysis of that deduced sequence revealed a signal peptidase I consensus sequence (Ala-Xaa-Ala) and an apparent signal peptide preceding the N-terminus of the 25 kDa protein sequenced above N-terminal sequencing of selected CFPs identified three novel products:
(1) protein with 72% identity to the N-terminus of a 42 kDa α-hydroxysteroid dehydrogenase of *Eubacterium* sp. VPI 12708;
(2) 27 kDa protein previously defined as MPT-51; and
(3) 56 kDa protein previously identified as glutamine synthetase.

Three proteins showed no significant homology between their N-termini and any known peptides. For these proteins and for others that were refractory to N-group analysis, more advanced methods of protein sequencing (e.g., LC-MS-MS) will permit acquisition of extended sequence information.

The protein cluster which was recognized by mAbs IT-42 and IT-57 was a primary focus of this study. These proteins migrated at a molecular mass range of 82-85 kDa in one co-inventor's laboratory (or 88 kDa in another co-inventor's laboratory) and a pI range of 5.12-5.19. Results described in Examples I, II and V referred to a CFP of approximately 88 kDa that reacted with 70% of sera from TB patients and demonstrated a specificity of 100%. Subsequent 2-D mapping coupled with 2-D western blot analysis showed these dominant antigens which induce early antibody responses in TB patients are the same as the proteins reactive with IT-57 and IT-42. As stated above, this antigen is referred to as the 88 kDa protein GlcB.

Although initial attempts of N-terminal sequencing of the proteins of this cluster were unsuccessful, LC-MS-MS studies demonstrated the presence of one products in this cluster, the katG catalase/peroxidase.

The generation of a detailed map of the culture filtrate of H37Rv through computer aided analysis allowed alignment and comparison of CFPs from other type strains of Mtb which revealed qualitative differences. However, all differences detected were associated with proteins observed in minor quantities. One explanation for these differences was that the growth characteristics of the three strains varied significantly. Several studies have noted the length of incubation of Mtb cultures has a dramatic effect on the profile of proteins released into the culture supernatant by the tubercle bacilli. In particular, the work of Andersen et al. (supra) demonstrates that a small, well defined set of proteins are actively excreted during the first three days of incubation and that the gradual secretion of cell wall proteins occurred during the logarithmic growth phase. Further the release of cytoplasmic proteins, as monitored by the presence of isocitrate dehydrogenase and the 65 kDa GroEL homolog are not observed until the end of logarithmic growth phase.

This type of broad survey of virulent Mtb strains has led to, and will continue to allow, the identification of immunologically important proteins and will lead to identification of novel virulence factors leading to improved approaches to chemotherapy. Thus, not only does the present invention enhance the overall knowledge in the art of the physiology of Mtb, but it also provides immediate tools for early serodiagnosis.

EXAMPLE IV

Further Characterization of the 88 kDa Antigen by Recombinant Methods

A. Determination of Identity of the 88 kDa Antigen Reactive with the mAb IT-57

The 2-D Western blot analysis and the 2-D mapping of the culture filtrates of Mtb (See: U.S. Pat. No. 6,245,331, 12 Jun. 2001, and WO 98/29132, published 9 Jul. 1998) suggested that the serodominant 88 kDa antigen may be the same protein as is recognized by mAbs IT-42 and IT-57 (# 101, 113, 124). In order to determine the identity of these antigens, mass spectrometry of the peptides prepared from the protein cluster that reacted with both IT-57 and IT-42, was performed. The results showed that protein # 124, reactive with both mAbs, was the KatG catalase/peroxidase. Peptide analysis of protein spots # 101 and 113 that reacted with only mAb IT-57 were inconclusive. In order to obtain the protein reactive with mAb IT-57, approximately 20,000 phages of a λgt11 Mtb expression library were screened by plaque blotting using mAb IT-57. The λgt11 clone reactive with mAb IT-57 and encoding a protein with a molecular mass of 88 kDa is designated "λgt11 (IT-57)." The lysates from E. coli lysogenized with λgt11 (IT-57) and the LFCFP were separated by SDS-PAGE polyacrylamide on 10% gels, transferred to nitrocellulose filters and probed with mAb IT-57. The mAb IT-57 recognized an 88 kDa band in the LFCFP and in the lysate of E. coli lysogen of λgt11 (IT-57). No proteins in the lysate from the E. coli 1089 lysogenized with the wild type λgt11 reacted with the mAb B. Hybridization of the Clone Coding for the 88 kDa Antigen with the katG Gene Since the spot on the 2-D blot reactive with mAb IT-57 showed some overlap with the spot reactive with mAb IT-42, it was important to determine if the 88 kDa protein encoded by the clone λgt11 (IT-57) was the katG gene product or if it was a different protein with a similar molecular weight and pI. The Mtb katG gene encoding the catalase/peroxidase enzyme cloned into the mycobacterial shuttle vector pMD31 was obtained from Dr. Sheldon Morris. The katG gene was excised from pMD31 with the enzymes KpnI and XbaI to yield an insert of 2.9 kb. An insert of approximately 3.2 kb obtained after EcoRI digestion of the DNA from % gt11 (IT-57) was used for hybridization with the katG gene. The 3.2 kb insert from λgt11 (IT-57) hybridized with itself and with both the uncut pMD31 vector containing the katG gene and the katG insert DNA itself (2.9 kb). Therefore, the 88 kDa antigen that reacted with mAb IT-57 was in fact the catalase/peroxidase protein.

C. Sequence of the Recombinant 88 kDa Antigen Expressed in E. coli

To confirm that the 88 kDa protein made by λgt11 (IT 57) was indeed the catalase/peroxidase enzyme, the insert DNA from this clone was sequenced and was found to be 99% homologous to the Mtb katG sequence by the NCBI BLAST search (accession number X68081).

D. Reactivity of TB Sera with the Recombinant Catalase/Peroxidase Protein Expressed in E. coli To determine the reactivity of the 88 kDa catalase/peroxidase protein with TB patient sera, fractionated cell lysates of E. coli-λgt11 (IT-57) were probed with sera from 6 advanced TB patients and 4 PPD+ healthy individuals. Neither the healthy control nor the TB sera reacted with the 88 kDa catalase/peroxidase protein. Therefore the 88 kDa catalase/peroxidase protein is not be the seroreactive antigen that was subsequently identified as GlcB.

E. Reactivity of Tuberculosis Sera with the 88 kDa Catalase/Peroxidase Protein Expressed in M. bovis BCG Since TB patient sera did not react with the recombinant catalase/peroxidase expressed in E. coli, the katG-negative BCG strain 35747 transformed with either the pMD31:Mtb katG or with the control pMD31 plasmid (vector control) were tested. The LFCFPs, crude lysates from the lysogen λgt11 (IT-57), lysogenic E. coli 1089 infected with wild-type λgt11, katG negative BCG strain containing pMD31:Mtb katG and the katG-negative BCG containing pMD31, were separated by SDS-PAGE polyacrylamide on 10% gels. The fractionated proteins were transferred to nitrocellulose filters and probed with an anti-catalase/peroxidase polyclonal serum (obtained from Dr. Clifton Barry, Rocky Mountain Laboratories, NIAID, Hamilton, Mont.), mAb IT-57, mAb IT-42 and serum from an advanced TB patient. The anti-catalase/peroxidase polyclonal serum and the mAb IT-57 reacted strongly with an 88 kDa antigen in the LFCFP, in the Mtb katG containing M. bovis BCG and in E. coli λgt11 (IT-57). MAb IT-42 reacted with the same bands in the LFCFP and the Mtb katG BCG, but not with the 88 kDa protein expressed in E. coli. The control lanes containing lysates of E. coli 1089 (λgt11) or of the katG-negative M. bovis BCG (pMD31 alone) failed to react with any of the mAbs.

In contrast to the results obtained with the anti-catalase/peroxidase antibodies, the serum from the TB patient recognized an 88 kDa antigen in the lysates of the katG-negative BCG strain. This is evidence that the seroreactive 88 kDa antigen is a novel protein which has not been previously described.

F. Reactivity of TB Sera with the Mtb 88 kDa Antigen GlcB

In order to confirm the presence in Mtb of a seroreactive 88 kDa antigen distinct from catalase/peroxidase, a katG-negative strain of Mtb (ATCC 35822) was tested. Lysates from this strain failed to react with any of the anti-catalase/peroxidase antibodies. However, when individual sera from healthy controls and TB patients of all three groups were tested with the same lysates, all the group III and group IV sera reacted with the 88 kDa protein.

Identification of the Amino Acid Sequence of the Sero-Reactive 88 kDa Protein GlcB The culture filtrate protein from a katG-negative strain of Mtb (ATCC 35822) was resolved as above by 2-D PAGE. The protein spot ("Spot 1") corresponding to the sero-reactive 88 kDa protein was cut out of the gel and subject to an in-gel digestion with trypsin. The resulting tryptic peptides were extracted, applied to a $C_{18}$ RP-HPLC column, and eluted with an increasing concentration of acetonitrile. The peptides eluted in this manner were introduced directly into a Finnigan LCQ Electrospray mass spectrometer. (See Materials and Methods above for further details.) The molecular mass of each peptide was determined, as was the charge state, with a zoom-scan program.

Identification of the 88 kDa protein GlcB was achieved by entering the mass spectroscopy date obtained above into the MS-Fit computer program and searching it against the Mtb database. The data input into the MS-Fit analysis and the results are shown below.

MS-FIT SEARCH DATA INPUT

| | | |
|---|---|---|
| Database: | NCBInr.07.09.99 | DNA Frame translation: 3 |
| Species: | Mycobacterium | |

-continued

MS-FIT SEARCH DATA INPUT

| | | |
|---|---|---|
| MW of Protein: | (from 65000 Da to 97000 Da) | |
| Protein pI: | (from 3.0 to 10.0) | All ☑ |
| Digest Used: | Trypsin | Max. # Missed Cleavages: 2 |
| Cysteines Modified by: | acrylamide | |
| Peptide N terminus: | Hydrogen (H) | |
| Peptide C terminus: | Free Acid (OH) | |
| Sample ID (comment): | Magic Bullet digest | |
| Max. reported Hits: | 25 | |
| Possible Modifications Mode: | Oxidation of M | |
| Peptide Mass Shift: | ±40.1 Da | |
| Peptide Masses are: | average | |
| Min. # Peptides to Match | 9 | |
| Report MOWSE Score ☑ | Pfa: 0.4 | |

Peptide Masses Input

| Mass (m/z) | Charge (z) |
|---|---|
| 527.9 | +2 |
| 1054.5 | |
| 559.0 | +2 |
| 947.5 | |
| 553.4 | +2 |
| 560.0 | +2 |
| 1105.5 | |
| 696.3 | +2 |
| 866.0 | +2 |
| 1002.3 | |
| 904.7 | +2 |
| 820.6 | +2 |
| 770.0 | +2 |
| 948.1 | +2 |
| 961.8 | +2 |
| 810.7 | +2 |
| 720.5 | +2 |
| 740.5 | +2 |
| 1209.0 | |
| 640.8 | +2 |
| 933.5 | +2 |
| 784.3 | +2 |
| 1545.7 | +2 |
| 1287.0 | +2 |

(mass tolerance: ±1.5 Da)

MS-FIT SEARCH RESULTS

| | |
|---|---|
| Sample ID (comment): | Magic Bullet digest |
| Database searched: | NCBInr.07.09.99 |
| Molecular weight search | (65000-97000 Da) selects 21170 entries. |
| Full pI range: | 324311 entries. |
| Species search | (*MYCOBACTERIUM*) selects 5990 entries. |

Combined molecular weight, pI and species searches select 333 entries.
MS-Fit search selects 80 entries (results displayed for top 10 matches

Result Summary

| Rank | MOWSE Score | # (%) Masses Matched | Protein MW (Da)/pI | Species | NCBInr. 9.7/98 Accession # | Protein Name |
|---|---|---|---|---|---|---|
| 1 | $6.59 \times 10^3$ | 19/26 (73%) | 80403/5.03 | *M. tuberculosis* | 2497795 | (Z78020) glcB |
| 2 | 425 | 7/26 (26%) | 66600/5.66 | *M. tuberculosis* | 3261657 | (Z81368) ggtB |
| 3 | 168 | 8/26 (30%) | 80142/5.09 | *M. leprae* | 2578377 | (AL008609) _G |
| 4 | 52.1 | 10/26 (38%) | 77122/5.39 | *M. tuberculosis* | 2501060 | (Z95387) thrS |
| 5 | 37.9 | 10/26 (38%) | 89926/5.6 | *M. tuberculosis* | 1731250 | Probably cation-trans ATPase CY3 |
| 6 | 32.2 | 7/26 (26%) | 95574/6.25 | *M. leprae* | 2398706 | (Z99125) hypo? protein MLCL |
| 6 | 32.1 | 7/26 (26%) | 95659/6.33 | *M. leprae* | 3024896 | (U00013) pps? B1496_C2_18 |
| 7 | 27.3 | 7/26 (26%) | 95033/5.37 | *M. tuberculosis* | 3261590 | (Z74025) ctpF |
| 8 | 26.4 | 8/26 (30%) | 65877/5.56 | *M. leprae* | 2959407 | (AL022118) re? Helicase DnaB |
| 9 | 21.1 | 7/26 (26%) | 81578/5.52 | *M. tuberculosis* | 1817676 | (Z84724) pkn? |
| 9 | 20.9 | 9/26 (34%) | 85425/5.37 | *M. tuberculosis* | 1781217 | (Z83867) nuo? |
| 10 | 18.5 | 7/26 (26%) | 95486/6.93 | *M. tuberculosis* | 2276335 | (Z97991) hypo? Protein Rv033 |

DETAILED RESULTS 1. 19/26 matches (73%) 80403.4 Da, pI = 5.03. Acc#2497795. *Mycobacterium tuberculosis* (Z78020) glcB (=GlcB)

The protein was identified as GlcB (Z78020) of Mtb, which is believed to be the enzyme malate synthase based on sequence homology to known proteins of other bacteria. This protein has the Accession number CAB01465 on the NCBI Genbank database (based on Cole, S. T. et al., Nature 393:537-544 (1998), which describes the complete genome sequence of Mtb). The sequence of this protein is SEQ ID NO:106 as provided above.

EXAMPLE V

Characterization of Serodominant Antigens of *M. tuberculosis*

The goal of this study was to determine the repertoire of antigens recognized by antibodies in TB patients in order to elucidate the human humoral response to Mtb and to evaluate the potential of these antigens as candidates for serodiagnosis. This was accomplished by immunoblotting Mtb H37Rv secreted antigens, which had been separated by 1- and 2-dimensional electrophoresis, with sera (*E. coli*-absorbed) from TB patients and healthy controls.

Of the more than 200 secreted proteins of Mtb, only 26 elicited antibodies in TB patients. The identity of several of these antigens was determined based on (a) their reactivity with murine mAbs, (b) N-terminal amino acid sequencing and (c) liquid chromatography-mass spectrometry (Example III). Twelve of these 26 antigens were recognized by sera from patients with early, non-cavitary TB and by patients with advanced cavitary TB. Of these twelve antigens, five, including the 88 kDa antigen (Example I), the MPT32 and Ag 85C, reacted strongly with sera from TB; the other two antigens have yet to be identified. The present invention is directed to the development of serodiagnostic assays (as described herein) employing these antigens that elicit antibodies in both early and advanced TB patients.

Materials and Methods

Subjects: (a) Advanced TB Patients

Serum samples from 33 HIV-negative individuals with confirmed pulmonary TB (advanced TB) were included in the study. Twenty of these sera were provided by Dr. J. M. Phadtare (see Example I). Nineteen of these patients were smear-positive and all had radiological evidence of moderate to advanced cavitary lesions. All these patients were bled 4-24 weeks after initiation of therapy.

(b) Early TB Patients: Thirteen TB patients from the Infectious Disease Clinic at the Manhattan VA Medical Center, New York, were culture positive, 6/13 were smear negative and 12/13 had minimal or no radiological lesions. These patients were bled either prior to, or within 1-2 weeks of, initiation of treatment.

(c) Control groups: Twenty-three HIV$^{neg}$, TB$^{neg}$, healthy individuals were included as controls. Sixteen of these were PPD$^+$ (skin test) and the remaining 7 were PPD$^{neg}$.

Antigens

Culture filtrates from log phase Mtb H$_{37}$Rv were used as the source of secreted antigens as described in Example I (LAM-free culture filtrate proteins or CFPs). The LFCFP preparation contained over 200 proteins (Example III, supra). Antigens were size fractionated by loading onto a preparative polyacrylamide tube gel, and proteins were separated by electrophoresis using an increasing wattage gradient (model 491 Prep Cell; Bio-Rad, Hercules, Calif.). Fractions were collected, assayed by SDS-PAGE and pooled according to molecular weights. Contaminating SDS was removed as described above. Reactivity of each fraction with human sera and an extensive panel of murine mAbs to Mtb antigens are described in Example I. Immunoadsorption of sera against *E. coli* lysates was performed as described in Example I. All ELISA assays, described in Example I, were performed using sera previously immunoadsorbed on *E. coli* lysates.

One-Dimensional (1-D) SDS-PAGE and 2-D PAGE of the LFCFPs

The fractionation of the LFCFPs (8 μg/lane) was performed on mini-gels using vertical slab units (SE 250 Mighty Small II, Hoeffer Scientific, San Francisco, Calif.) with a 10% separating gel and 5% stacking gel. The gels were either stained with a silver stain (Bio-Rad Silver Stain Kit, Hercules, Calif.) or used for electrophoretic transfer for immunoblotting. The separated proteins were transferred onto nitrocellulose membranes for 1.5 hrs at a constant 100 V. 2-D PAGE was performed as described in Example III. Proteins resolved by 2-D PAGE were transferred to nitrocellulose membranes as described.

Western Blot Analysis

The 1-D and 2-D blots were blocked with 3% BSA in phosphate buffered saline (PBS) for 2 hrs, and washed for 1 hr with PBS/Tween 2% (wash buffer). Individual lanes containing fractionated LFCFPs were exposed overnight at 4° to individual sera (diluted 1:100 with 1% BSA in PBS). The blots containing the 2-D fractionated LFCFPs were probed with four different serum pools comprised of individual sera whose reactivity with the above antigen preparations were previously determined by ELISA. The pools included (a) 6 PPD positive healthy control sera with no specific reactivity against any of the antigens (group I), (b) 6 TB patients that lacked reactivity to all 3 antigen preparations by ELISA (group II), (c) 6 TB patients reactive with the total LFCFPs and the sized 88 kDa preparation, but not the 38 kDa antigen preparation (group III), and (d) 6 TB patients reactive with both the sized preparations (38 and 88 kDa antigens; group IV). Exposure of the blots to the individual sera or serum pools was followed by washing for 1.5 hrs with the wash buffer, after which alkaline phosphatase-conjugated anti-human IgG (diluted 1:2000, Zymed, Calif.) was added for 1.5 hrs. The blots were washed again for 2 hrs and developed with BCIP/NBT substrate (Kirkegaard & Perry Laboratories, Gaithersburg, Md.).

Results

Reactivity of Sera with Secreted Antigens of Mtb

Sera were grouped according to reactivity by ELISA with total LFCFPs, or the sized fraction containing the 38 kDa PstS or the 88 kDa seroreactive protein (Table 5). Group I includes sera from 16 PPD$^+$ and 7 PPD$^{neg}$ healthy controls, none of whom were positive in ELISA with any of these antigen preparations. Group II includes 9 TB patients who tested antibody negative with all three antigen preparations; five of these patients were smear-positive and had cavitary disease. The remaining four patients lacked cavitary lesions, but two of these four were smear-positive. Group III includes thirteen patients with antibodies to both the LFCFPs and the fraction containing the 88 kDa antigen, but not the fraction containing the 38 kDa antigen. Five of these patients were smear-positive and had pulmonary cavitations. An additional four were smear-positive but lacked any cavitary lesions. The remaining four were smear negative and had no cavitations. Group IV included eleven patients, all of whom had antibodies to all three antigen preparations; 10/11 were smear-positive and all had radiological evidence of moderate to advanced cavitary disease.

TABLE 5

Classification of TB Patients

| Serum Group | n[a] | Smear Positivity | Radiological Cavitations | LAM-free CFP | REACTIVITY WITH: Fraction with 88 kDa Ag | Fraction with 38 kDa Ag |
|---|---|---|---|---|---|---|
| I | 23 | 0 | 0 | 0 | 0 | 0 |
| II | 9 | 7 | 5 | 0 | 0 | 0 |
| III | 13 | 9 | 5 | 11 | 13 | 0 |
| IV | 11 | 10 | 11 | 11 | 11 | 11 |

[a]n = number of individuals in each group

Antigens in LFCFPs Recognized by Sera

Resolution of the LFCFP preparation by SDS-PAGE revealed a broad range of proteins from 14 to >112 kDa, as seen by silver staining. Sera (diluted 1:100) from individuals in all four groups were used to probe Western blots prepared from the fractionated LFCFPs. Because of the large number of individual sera tested, several blots were performed. Consequently, not all antigen bands were exactly matched when the blots were combined to show the reactivities. For standardization, the 65 kDa band was aligned. In sera from group I individuals (PPD[+] and PPD[neg] healthy controls) the major antigens recognized by sera from 6 PPD[neg] healthy individuals have molecular weights of 26, 30-32 kDa and 65 kDa. The 30-32 and 65 kDa antigens were also recognized by sera of the 9 PPD[+] healthy controls, though only 3/9 sera in this group recognized the 26 kDa antigen, and one serum sample recognized an additional 68 kDa antigen.

Group II tuberculosis sera were antibody negative with all 3 antigen preparations by ELISA. Despite some variability among individual tuberculosis sera, all reacted with the 30-32 kDa and 65 kDa antigens, and 5/8 contained antibodies to the 26 kDa antigen that was also recognized by the controls. Serum from one patient showed strong reactivity with 46, 55 and 97 kDa antigens. Four sera, including the latter patient, showed faint reactivity with antigens of 74, 76, 88, 105 and 112 kDa antigens, and with some antigens between 46-55 kDa. Sera from patients with cavitary disease and sera from patients with no cavitations showed no significant difference in reactivity.

Group III patients had antibodies by ELISA to the LFCFPs and the 88 kDa preparation. Ten of the 11 sera showed moderate reactivity with the 88 kDa antigen GlcB. In addition, these sera also recognized antigens of 74, 76, 105, 112 kDa, and some antigens in the region of 46-55 kDa. Although non-reactive by ELISA, 3 of 11 sera reacted with a 38 kDa antigen. This may indicate binding to a recently described 38 kDa antigen (Bigi, F. et al., 1995, *Infect. Immun.* 63:2581-2586) which is distinct from the PstS protein. No differences were observed in the reactivity pattern between (a) sera of patients who lacked pulmonary cavitations (lanes 25-30) and (b) sera from patients with advanced cavitary lesions (lanes 31-35).

The sera of group IV patients who were reactive with all three antigen preparations by ELISA (lanes 36-43), reacted very strongly with the 38 kDa antigen and recognized a 34 kDa antigen that was not recognized by any of the group III sera. Besides these two antigens, the antigens identified by group IV sera were the same as for group III sera, although the reactivity with individual antigens was markedly stronger. The reactivity with the 88 kDa GlcB antigen was strong in 7/8 sera.

In summary, all antibody-positive TB patients (groups III and IV) reacted primarily with antigens having molecule masses >46 kDa. Antigens of 74, 76, 88, 105, 112 kDa and antigens in the 46-55 kDa region are frequent targets of human antibody responses. In contrast, the 38 kDa and 34 kDa antigens were recognized by a more restricted group of patients (group IV).

Identification of Antigens Recognized by TB Patient Sera

2D-PAGE provides enhanced resolution of complex protein mixtures. The LFCFPs preparation resolves into about 200 different proteins by this method. A complete 2-D map of the total CFPs of Mtb is shown in U.S. Pat. No. 6,245,331 and WO 98/29132 (and discussed in Example III). 2D immunoblots of the fractionated LFCFPs were probed with serum pools corresponding to patient groups I-IV. The reactivity of each serum pool was compared with the reactivity of murine mAbs to identify the antigens recognized by TB patients' sera (Table 6).

The results with the four serum pools are described in Table 6A-C. The reference number for each antigen is that assigned in Example III, supra). All four serum pools reacted with 4 secreted antigens and 3 of 4 pools reacted with 2 additional secreted antigens (Table 6A). These six proteins were clearly seen in the 2-D blots reacting with pooled sera from healthy controls (group I). Reactivity with murine mAb IT-49 identified two of them to be the Ag 85B (#81, 29 kDa) and Ag 85A (#149, 31 kDa). These antigens correspond to the 30-32 kDa doublet, observed on 1-D immunoblots. The other two antigens reactive with all serum groups had molecular weights of 55 kDa (#114, 120) and 58 kDa (#86, 96, 105) and failed to react with the murine mAbs. The former antigen has been identified as the glutamine synthetase by N-group analysis (Example III, above). These antigens may correspond to the 65 kDa antigen that was reactive with the individual sera on 1-D blots. A 26 kDa antigen (#19, 29) and a 46 kDa (#51) were reactive with the control sera (group I) and antibody positive TB sera (group III and group IV), but failed to react with the antibody negative TB serum pool (group II). The former antigen (26 kDa, #19, 29) was identified as MPT64 based on reactivity with the murine mAb IT-67 and may be the 26 kDa antigen recognized by several control sera on 1-D blots.

The reactivity of a serum pool of group II TB patients (which sera lack ELISA-reactive antibodies to any of the secreted antigens tested) is described in Table 6A. This serum pool was weakly reactive with the four antigens (29, 31, 55, and 58 kDa) to which the control group (group I) reacted, but failed to show any reactivity with the 25/26 (#19, 29) and 46 kDa (#51) antigens.

The serum pool from TB patients containing antibodies to the 88 kDa (GlcB) but not the 38 kDa antigen (group III), reacted with 18 secreted antigens on 2-D blots (Table 6B). Of these, six were identical to those identified by the healthy control serum pool (group I; Table 6A). Of the remaining twelve antigens, three had molecular masses below 30 kDa: one was a 26 kDa antigen (#170, MPT51), reactive with mAb IT52 and the two others (28 kDa, #77; and 29/30 kDa, #69, 59) did not react with any of the mAbs tested. In the 30-60 kDa range, reactivity with a 31 kDa (#119, mAb IT-49, Ag 85C) and a 38/42 kDa antigen (#11, 14, MPT32) was strong, and a low level of reactivity was discernible with one isomer of the 35 kDa antigen (#66, IT-23, PstS). A 49 kDa protein (#82) was reactive with mAb IT-58). Three antigens, with molecular weights of 31 kDa, (#103), 42 kDa (#68, 80) and 48 kDa (#24) were not identified by any mAbs. These antigens correspond to the multiple bands in the 30 to 60 kDa region on the 1-D blots. In the region of 65-100 kDa, a 85 kDa protein (#113, 124, IT-42, IT-57), was reactive with this serum pool, but no antigens corresponding to the 74 and 76 kDa antigens seen on 1-D blots were discernible on the 2-D blot. The 85 kDa antigen (#113, 124) on the 2-D immunoblots corresponds to the 88 kDa antigen GlcB (Example I and Example III). This was also confirmed by checking the reactivity of the fractionated LFCFPs with mAbs IT-42 and IT-57, both of which identified an 88 kDa band. The 104 kDa protein (#111) corresponds to the 105 kDa seen on the 1-D blots. Nothing corresponding to the 112 kDa antigen on the 1-D immunoblots was observed on the 2-D immunoblots.

The serum pool from group IV TB patients recognized 11 of 12 antigens that were reactive with the group III serum pool (except the 28 kDa antigen, #77; Table 6B). The reactivity of the group IV serum pool however, with the 26 kDa (#170, MPT51), 31 kDa (#119, Ag 85C), 35 kDa (#66, PstS), 38/42 (#11, 14, MPT32), 49 kDa (#82; IT-58), 85 kDa (#113, 124) and the 104 kDa (#111) antigens, was stronger than with the group III serum pool. In contrast to the group III pool which showed faint reactivity with only one isomer of the 35 kDa antigen (#66, PstS), the group IV pool was reactive with all four isomers recognized by murine mAb IT-23. Besides the 11 antigens listed to be reactive with both the group III and IV serum pools (Table 6B), the latter group also reacted with eight additional antigens (Table 6C). The antigen with a molecular weight below 30 kDa was the 13/14 kDa protein (#23, 38, IT-12 and SA12, GroES). In the 30-38 kDa region, this serum pool recognized four new antigens, with the same 31 kDa molecular weight but differing in their pI values: 31 kDa (#15, 16, 22, 25), 31 kDa (#62), 31 kDa (#57) and 31 kDa (#37), and a fifth antigen of 38 kDa (#32). Of these only the 31 kDa (#15, 16, 22, 25) was reactive with the mAb IT-44, while the remaining 4 antigens have not been previously described. In the region above 65 kDa, this pool reacted with a 66/72 kDa protein (#65, 79, mAb IT-40 and IT-41, DnaK), and an unidentified 79 kDa antigen (#78).

In summary, of the 26 antigens that are recognized by TB sera, 6 were reactive with the control sera (Table 6A). Twelve of these 26 antigens are recognized by sera from groups III and IV (Table 6B). Thus, patients both with early, non cavitary TB and advanced cavitary TB have antibodies to these antigens. Of these 12 antigens, 5 are strongly recognized and consequently, are preferred antigens for a serodiagnostic assay for early TB as described herein. These are the 85 kDa/88 kDa antigen (#113, 124; Example D, the 38/42 protein (#11,14, MPT32), the 31 kDa antigen (#119, Ag 85C), an uncharacterized 49 kDa antigen (#82; IT-58), and a 26 kDa antigen (#170, IT-52). In contrast, eight additional antigens listed in Table 6C, and the 38 kDa protein (#66, PstS; Table 6B) are recognized primarily by advanced TB sera and would therefore be of limited serodiagnostic value.

Discussion

Of the approximately 200 proteins secreted by replicating bacteria, only a limited subset is recognized by the TB patients' immune system resulting in antibodies with appropriate specificity in the patients' sera. Even within this subset, some antigens are recognized by early and advanced (late) TB patients whereas others are recognized exclusively by late TB patients. In view of the fact that the 38 kDa PstS protein was the most "successful" serodiagnostic antigen known in the art (Bothamley et al., 1992, supra; Harboe et al., 1992, *J. Infect. Dis.*, supra), the present discovery of several antigens that are recognized by patients who lack anti-38 kDa antibodies is very important. As shown here and in the earlier Examples, removal of cross-reactive antibodies from sera by immunoadsorption with *E. coli* antigens allows definition of Mtb antigens with strongly seroreactive epitopes. Previous attempts to identify antigens of Mtb that elicit antibodies in diseased individuals had limited success. Verbon et al. (supra) found no difference between reactivity of patient and control sera. Espitia et al. (supra) (also using unabsorbed sera) identified only the 38 kDa PstS protein. This antigen reacted with only 57% of TB sera. The immunoadsorption of sera with *E. coli* lysates eliminates the cross-reactive antibodies that have hindered the definition of seroreactive antigens. In addition, the 2-D analysis and mapping of each antigen as described herein has allowed precise definition of antigens that appear to be critical for rational design of serodiagnosis and at least 5 secreted proteins as useful serodiagnostic agents. Antibodies to one of these, the 88 kDa antigen GlcB, are present in 80% of the advanced and 50% of the early TB. The 38/42 kDa antigen (#11, 14, MPT32) has also been suggested to have serodiagnostic potential (Espitia et al., 1995, supra) but not as an "early" antigen. The remaining 3 antigens, the 49 kDa (#82; IT-58), 31 kDa antigen (#119, Ag 85C), and the 26 kDa (#170, IT-52) have never been used for assessing seroreactivity in patients until the making of the present invention.

The present inventors' laboratories have changed the Reference Number designation of some of the spots on the 2D gels shown in U.S. Pat. No. 6,245,331 (12 Jun. 2001) and WO 98/29132 (published 9 Jul. 1998) from a numeric to an alpha (letter) labeling. See, also, their publication, Samanich, K M et al., *J. Infec. Dis.* 178:1534-1538 (1998), which is incorporated by reference in its entirety. The correspondence of some spot number to letter designations are given in the legend to FIG. 1 of that publication and reproduced below:

| New Ref (alpha) | Corresponding numeric |
| --- | --- |
| A | na* |
| B | 86, 96, 105 |
| C | 77 |
| D | 59, 69 |
| E | 103 |
| F | 68, 80 |
| G | 24 |
| H | na |
| I | 111 |
| J | 57 |
| K | 62 |
| L | 32 |
| M | 78 |

*na = not assigned; Ref numbers in table based on Sonnenberg et al., 1997, supra, as used in the present examples

TABLE 6

Antigens Recognized by Various Serum Pools

| Antigen MW[a] | pI | Ref[b] | Reactive mAb (Antigen Identified) | Reactivity with serum pools Grp I | II | III | IV |
|---|---|---|---|---|---|---|---|
| A. ANTIGENS RECOGNIZED BY ALL FOUR SERUM POOLS | | | | | | | |
| 25/26 | 4.65-4.83 | 19, 29 | IT-67 (MPT64) | ++ | NR | ++ | +++ |
| 29 | 5.10 | 81 | IT-49 (Ag 85B) | ++ | ++ | +++ | +++ |
| 31 | 5.38 | 149 | IT-49 (Ag 85A) | + | ++ | +++ | +++ |
| 46 | 5.05 | 51 | none | ± | NR | ++ | +++ |
| 55 | 5.14-5.17 | 114, 120 | glutamine synthetase | ± | ± | ++ | +++ |
| 58 | 5.11-5.12 | 86, 95, 105 | NONE | ++ | ++ | ++ | +++ |
| B. ANTIGENS RECOGNIZED ONLY BY GROUP III AND IV TB PATIENTS | | | | | | | |
| 26 | 5.91 | 170 | IT-52 (MPT51) | NR | NR | ++ | +++ |
| 28 | 5.10 | 77 | none | | | ± | NR |
| 29/30 | 5.08 | 69, 59 | none | | | + | + |
| 31 | 5.12 | 103 | none | | | + | + |
| 31 | 5.17 | 119 | IT-49 (Ag85C) | | | +++ | +++ |
| 35 (38) | 5.09 | 66 | IT-23 (PstS) | | | ± | +++ |
| < | 4.31-4.51 | 11, 14 | polyclonal antisera (MPT32) | | | ++ | +++ |
| 42 | 5.10 | 68, 80 | none | | | + | + |
| 48 | 4.79 | 24 | none | | | + | + |
| 49 | 5.10 | 82 | IT-58 | | | ++ | +++ |
| 85 (88) | 5.14-5.19 | 113, 124 | IT-42, IT-57 | | | ++ | +++ |
| 104 | 5.13 | 111 | none | | | + | ++ |
| C. ANTIGENS RECOGNIZED ONLY BY GROUP IV TB PATIENTS | | | | | | | |
| 13/14 | 4.76-4.93 | 23, 38 | SA-12, IT-10 (GroES) | NR | NR | NR | + |
| 31 | 4.53-4.79 | 15, 16, 22, 25 | IT-44 | | | | +++ |
| 31 | 5.09 | 62 | NONE | | | | ± |
| 31 | 5.08 | 57 | NONE | | | | ++ |
| 31 | 4.93 | 37 | NONE | | | | + |
| 38 | 4.87 | 32 | NONE | | | | ++ |
| 66/72 | 5.09-5.10 | 65, 79 | IT-40, IT-41 (DnaK) | | | | +++ |
| 79 | 5.10 | 78 | NONE | | | | + |

[a]Antigen molecular weight (MW) given in kDa
[b]Reference numbers correspond to the 2-D PAGE map of CFPs of Mtb H$_{37}$Rv (Example III)
NR: Not reactive In addition to the five aforementioned "early" antigens, seven additional antigens showed reactivity with the group III serum pool:

(1) the 28 kDa (#77) antigen,
(2) the 29/30 kDa (#69, 59) antigen,
(3) the 31 kDa (#103) antigen,
(4) the 35 kDa (#66, IT-23) antigen,
(5) the 42 kDa (#68, 80) antigen,
(6) the 48 kDa (#24) antigen, and
(7) the 104 kDa (#111) antigen.

Hence, the presence of one or more of these antigens, an epitope-bearing peptide thereof or a reactive variant of the peptide, in an immunodiagnostic preparation in combination with one or more of the five early antigens (or a peptide thereof) described above enhances the sensitivity of the diagnostic assay.

Three other antigens which have apparently strong serodominant epitopes based on their significantly stronger reactivity with the antibody-positive TB sera (groups III and IV) than with sera of antibody negative TB patient sera and control sera (groups I and II; Table 6A) are: (a) the 55 kDa (#114, 120, glutamine synthetase) antigen, (b) a 46 kDa protein (#51, IT-58) antigen and (c) the 31 kDa (#149, Ag 85A) antigen. The serodiagnostic potential of Ags 85A (#149) and B (#81) has been evaluated by Van Vooren et al. (supra) by isoelectric focusing separation and immunoblot analysis. The 85A component was shown to be reactive with the TB as well as non-TB sera, whereas, 71% of the TB sera in their cohort recognized either Ag 85 B or C. Importantly, no information on reactivity in early vs. advanced disease was provided.

The present results revealed that Ag 85A and 85B were strongly reactive with patient sera, and less reactive with controls, although the 85B was more cross-reactive with control sera. Studies with the Ag 85 components led to the suggestion that serodiagnostic potential of these antigens will lie in their specific epitopes (Wiker et al., 1992, *Microbiol. Rev*, supra). The present results constitutes a major step in that direction and provides a basis for the identification and detection of such epitopes.

Another protein currently being assessed as a serodiagnosis candidate is MPT64 (26 kDa, #19, 29) (Verbon et al., 1993, supra) was reported to provide sensitivities of about 46% in active TB patients. However, the present 2-D analyses suggests that this protein, although strongly reactive with sera of advanced TB patients, fails to discriminate between the group III TB sera (lacking anti-38 kDa antibodies) and the healthy controls (group I).

The early antigens identified herein may not be the only early antigens secreted during Mtb growth in vivo. These antigens may be the only ones that are distinguishable because of their strongly seroreactive epitopes. Several antigens of Mtb were either up- or down-regulated when the organisms were grown intracellularly in macrophages. The present inventors propose that, in vivo, Mtb organisms produce only those proteins required for survival and growth under these particular conditions which may differ from the requirements during growth in culture media. It is noteworthy that several of the antigens that elicit antibodies relatively early in TB (based on reactivity with group III sera), are implicated as having a role in pathogenesis in vivo. Thus, Ag 85A, Ag 85C and MPT51 all belong to the family of secreted proteins which bind to fibronectin (Wiker et al., 1992, *Scand. J. Immunol.*, supra)). MPT32 is homologous to a fibronectin-binding protein of *M. leprae* (Schorey, J. S. et al., 1995, *Infect. Immun.* 63:2652-2657).

It is noteworthy that the 28 kDa antigen (#77) reacted with the group III but not the group IV serum pools, suggesting differential expression of some antigens during different stages of disease progression (Amara, R. R. et al., 1996, *Infect. Immun.* 64:3765-3771).

Based on the foregoing discoveries, the present inventors have identified seroreactive antigens which are useful for diagnostic assays for TB patients who are relatively early in disease progression. In view of the expected homology of these antigens with similar proteins in other mycobacterial species, species-specific epitopes should now be defined for serodiagnostic uses.

If the absence of detectable antibodies (by ELISA) is due to the formation of immune complexes in vivo (Grange, supra), the present invention provides methods to identify such complexes containing these antibodies.

In view of the large number of antigens secreted by replicating Mtb in culture, it is significant that such a small number of antigens are reactive with TB patient antibodies. Extensive efforts have been expended in the art to develop serodiagnostic tools using Ag 85A and 85B and the 38 (or 35) kDa antigens. The present invention clearly show that at least five additional secreted antigens are recognized by a significantly larger proportion of TB patients. These antigens are used to design serodiagnostic tests for TB as disclosed herein.

EXAMPLE VI

Figure 3:
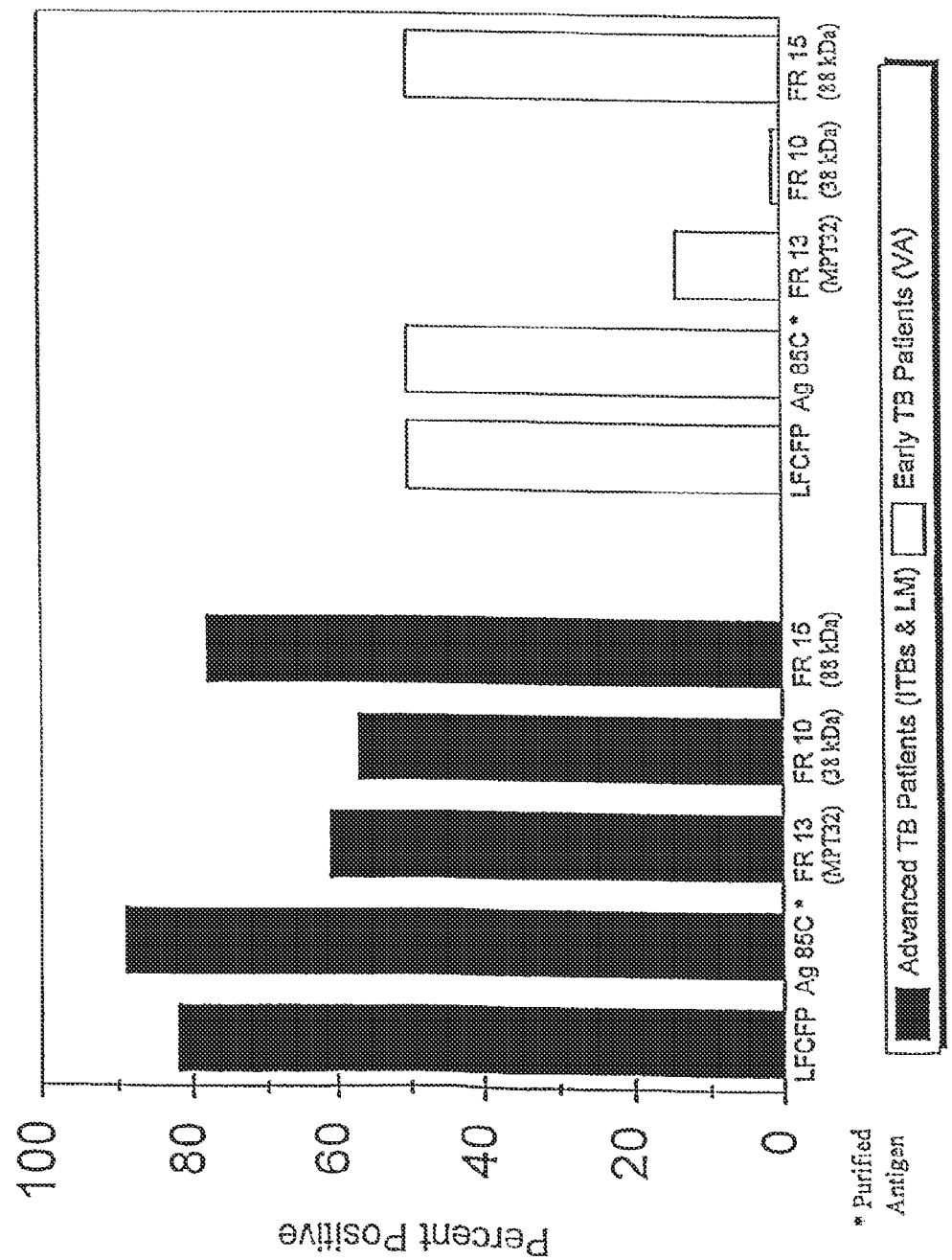
FIG. 3 is a graph showing reactivity of sera from advanced (black bars) and early (white bars) TB patients to M. tuberculosis LFCFP, purified Ag85C or three fractions (13, 10 and 15) enriched for three early antigens (shown in parentheses below the fraction designation).
Figure 4:
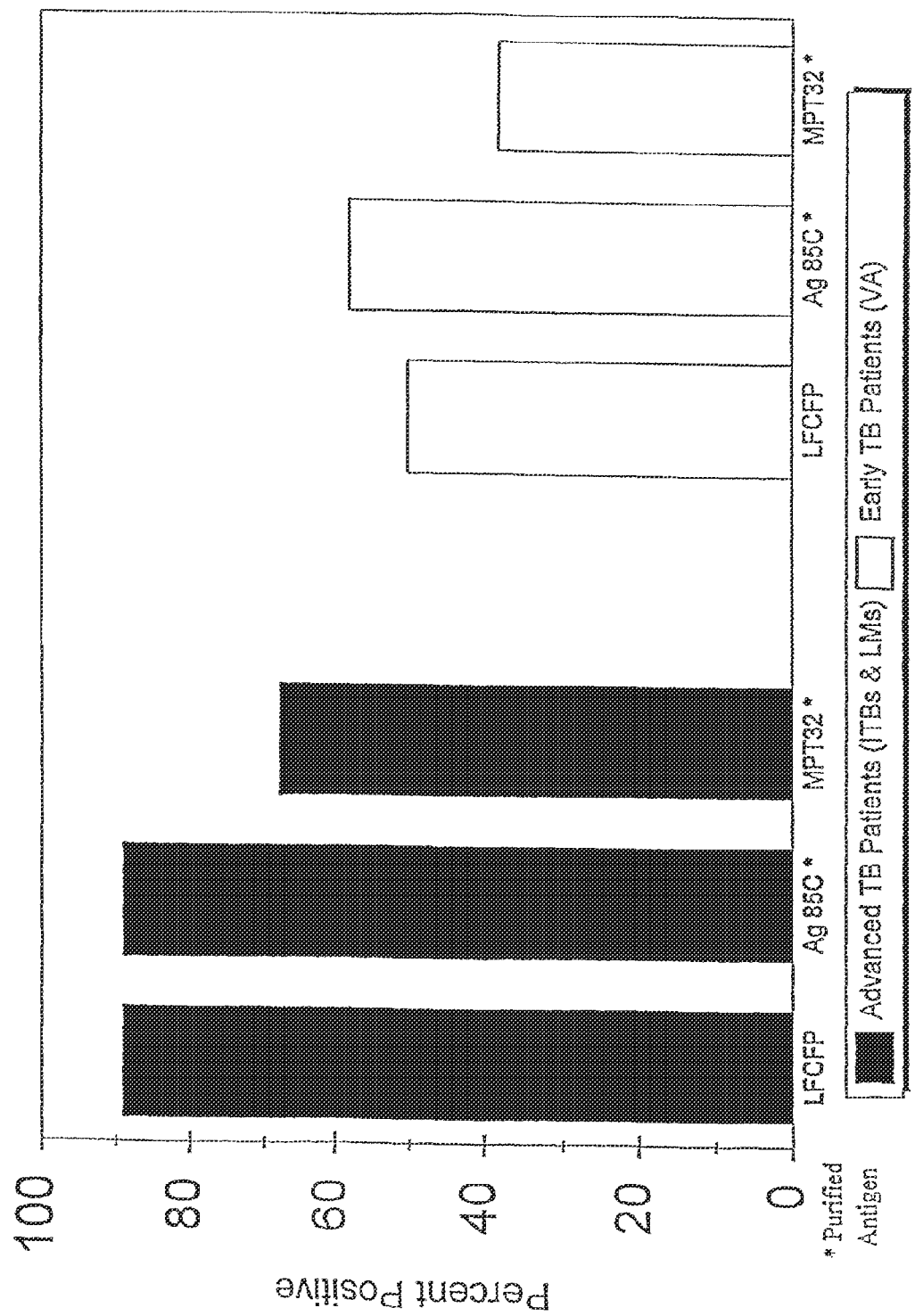
FIG. 4 is a graph showing reactivity of sera from advanced (black bars) and early (white bars) TB patients to Mtb LFCFP, purified Ag85C or purified MPT32.

Reactivity of Sera from TB Patients with Purified Antigens and Selected Antigen Fractions The reactivity of patient and control sera with LFCFP, with fractions 10, 13 and 15, and with purified antigens Ag85C and MPT32 are summarized in FIGS. 3 and 4 and Table 7. As discussed above in Examples I and II, fraction 10 is enriched for a 38 kDa antigen, fraction 13 is enriched for MPT32 and fraction 15 is enriched for the 88 kDa antigen GlcB, the results show that all advanced TB patients who have antibodies to LFCFP can be detected by the use of Ag85C or antigen in Fraction 15. A significant proportion of these patients also have antibodies to MPT32 (Fraction 13) and the 38 kDa antigen (Fraction 10). However, Ag85C and the 88 kDa protein were recognized by most patients' immune systems resulting in antibodies.

All early TB patients who are reactive with LFCFP are also reactive with MPT32 none are reactive with the 38 kDa antigen. Reactivity with purified MPT32 is higher in the early TB group (FIG. 4) than is reactivity with a partially purified (Fraction 13) antigen (FIG. 3).

These results confirm that the reactivity of sera from early TB patients with at least three of the five early antigens described in the present invention (Example I). These findings prove that the use of purified early antigens results in enhanced assay sensitivity in patients with early TB, allowing for improved rapid detection methods.

Of these antigens, only MPT32 has received any consideration in the context of TB serodiagnosis. However, none of these antigens have ever been shown to react with early TB patient sera. Hence, this is the first suggestion of their use in methods to diagnosis TB in its early stages, which is of particular importance to immunocompromised patient such as those infected with HIV.

Reactivity of Individual Sera with Antigens

The reactivity of any single antigen on the 2-D blots with pooled sera may represent reactivity with only some of the individual sera comprising the pool. To confirm that the antigens recognized by group III serum pool are broadly reactive, individual sera were assessed for antibodies to two of the antigens identified by the group III serum pool, Ag 85C and MPT32 which the present inventors had purified. Reactivities with the purified 38 kDa PstS antigen and the 88 kDa antigen GlcB (in fraction 15) was also tested. A larger cohort of TB patients than above, classified as cavitary or non-cavitary TB, was tested. Sera of 27 of the 34 (79%) cavitary and 9/20 (45%) non-cavitary patients were reactive with the 88 kDa antigen (Table 8) and 29/34 (85%) cavitary and 9/20 (45%) non-cavitary patient sera were reactive with Ag 85C (Table 6). Sera of 29 of 34 (85%) cavitary and 5/20 (25%) non-cavitary patients were reactive with the MPT32 (FIG. 4 and Table 8). In contrast, 18/34 (53%) cavitary and only 1/20 (5%) of the non-cavitary patients were reactive with the purified 38 kDa antigen (Table 8).

Analysis of these results, wherein reactivity with one or more of the 3 antigens identified herein was considered as positive reactivity, showed that antibodies were detectable in 31/34 (91%) of the cavitary and 12/20 (60%) of non cavitary TB patients.

The entire cohort of TB patients was also analyzed to determine whether smear positivity and the detection of antibodies to the purified antigens tested above were comparable as methods for diagnosis of TB. Table 9 shows that 43/54 (80%) of all the TB patients are diagnosed by sputum smear and 43/54 (80%) are diagnosed by ELISA.

TABLE 7

Reactivity of Patient Populations to Purified or Fractionated Mtb Antigen
Purified Antigen or Antigen Fraction (at Serum Dilution)

| Subjects | Ag85 C (1:100) | MPT32 (1:150) | LFCFP (1:1000) | F13 (MPT32)[1] 1/200 | F15 (88 kDa) 1:200/400 | F10 (38 kDa) (1:200) |
|---|---|---|---|---|---|---|
| All TB | 36/50 | 28/52 | 30/42 | 19/50 | 29/42 | 16/42 |
|  | 72% | 54% | 72% | 38% | 69% | 38% |
| Advanced TB | 25/28 | 19/28 | 23/28 | 17/28 | 22/28 | 16/28 |
|  | 89% | 68% | 82% | 61% | 78% | 57% |
| Early TB | 11/22 | 9/24 | 7/14 | 2/14 | 7/14 | 0/14 |
|  | 50% | 38% | 50% | 14% | 50% | 0% |
| PPD$^+$HC | 0/18 | 0/21 | 0/16 | 0/16 | 0/16 | 0/16 |
|  | 0% | 0% | 0% | 0% | 0% | 0% |
| PPD$^{neg}$ HC | 0/13 | 0/13 | 0/16 | 0/16 | 1/16 | 0/16 |
|  | 0% | 0% | 0% | 0% | 6% | 0% |
| HIV$^+$ HC | 0/39 | 0/34 | 0/21 | 0/16 | 0/21 | 0/21 |
|  | 0% | 0% | 0% | 0% | 0% | 0% |
| HIV$^+$ TB (pre or at) | 16/52 31% | ND | 23/50 46% | ND | 37/52 71% | 34/52** 65% |

Subject designations are as in Examples I and II.
HC = healthy controls.
HIV$^+$ patients with TB included those diagnosed before (pre) or at the time of (at) TB diagnosis.
**Borderline values of OD Although not all smear-positive patients had detectable antibodies and not all antibody-positive patients had positive smears, the combination of smear and ELISA could diagnose 50/54 (93%) of the TB patients.

When the patients were classified into cavitary and non-cavitary TB, 97% (33/34) of cavitary and 45% (9/20) of non-cavitary TB patients were detected by smears. The sensitivity of antibody (only) detection was 91% (31/34) and 60% (12/20), respectively.

Thus, by using a combination of the two methods, the sensitivities were increased to 100% with cavitary TB and 80% (16/20) with non-cavitary TB patients. These results indicate that the greatest sensitivity for diagnosis of TB is attained by simultaneous use of the sputum smear and the ELISA for antibodies reactive with the antigens described herein.

TABLE 8

Reactivity of Sera with Different *M. tuberculosis* Antigens.

|  | SENSITIVITY(%) | | | |
|---|---|---|---|---|
| ANTIGEN | Total TB (n = 54) | Cavitary (n = 34) | Non Cavitary (n = 20) | SPECIFICITY(%) (n = 83) |
| 88 kDa (GlcB) | 70 | 79 | 45 | 100 |
| Ag 85C | 70 | 85 | 45 | 100 |
| MPT32 | 63 | 85 | 25 | 98 |
| 38 kDa | 35 | 53 | 5 | 100 |

TABLE 9

DIAGNOSIS OF TUBERCULOSIS

|  |  | Number of Patients (%) that are: | | |
|---|---|---|---|---|
| Patients | N | Smear+ | Ab+ | Smear+/Ab+ |
| Tuberculosis | 54 | 43 (80%) | 43 (80%) | 50 (93%)* |
| Cavitary TB | 34 | 33 (97%) | 31 (91%) | 34 (100%) |
| Non-Cavitary | 20 | 9 (45%) | 12 (60%) | 16 (80%) |

*8 of 12 smear-negative patients were antibody-positive.

EXAMPLE VII

Anti-Mycobacterial Antibodies in Urine

Subjects

Paired serum and urine samples were obtained from 23 smear-positive, untreated (=late) TB patients attending the TB clinic at the LRS Hospital for Tuberculosis and Allied diseases at New Delhi, India. Forty-one sera and 24 urine samples obtained from PPD positive and PPD negative healthy individuals were tested as negative controls.

Determination of Anti-Mycobacterial Antibodies:

The reactivity of the serum samples with the culture filtrate proteins of Mtb was evaluated by ELISA as described above. To evaluate the presence of anti-mycobacterial antibodies in the urine samples, ELISA plates were coated overnight with 125 µl of a 4 µg/ml suspension of the culture filtrate proteins of Mtb at 4° C. The next morning, the plates were washed with PBS, and 125 µl of urine were added to each well. After 90 min., the plates were washed with PBS-Tween, and the bound antibody detected by anti-human IgG-Alkaline Phosphatase conjugate, and the substrate for the enzyme.

Figure 5:
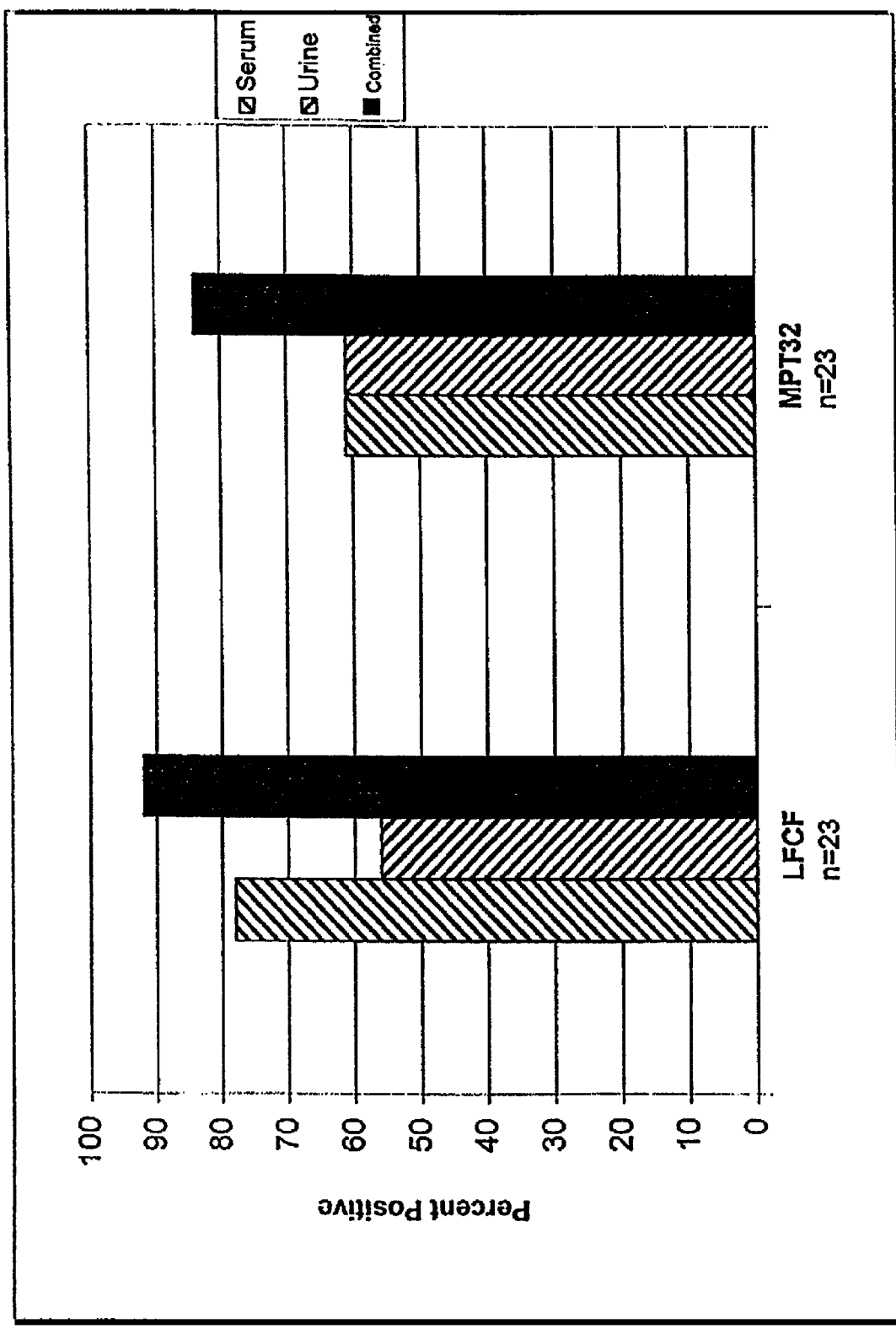
FIG. 5 is a graph showing reactivity of urine and sera from late TB patients with LFCF and MP32 protein. Results are presented as percent samples that are positive.

At specificities exceeding 98%, sera from 78% of the (late) TB patients and urine samples from 56% had antibodies that bound to antigens in the Mtb culture filtrates (FIG. 5, left). Taking into account the presence of antibodies in at-least one of the two body fluids (serum and/or urine), 92% of the patients had anti-mycobacterial antibodies. The same serum and urine samples were also evaluated for reactivity with purified MPT 32 (FIG. 5, right), which is one of the preferred antigens for the serodiagnostic test to detect early infection. In both cases, anti-MPT 32 antibodies were present in specimens from 14/23 (61%) patients. Again, when considering the presence of anti-MPT 32 antibodies in at-least one of these two body fluids, 83% of the patients had anti-MPT 32 antibodies.

To determine which culture filtrate antigens were recognized by these urine antibodies, Western blots were prepared from culture filtrate proteins fractionated on 10% SDS-polyacrylamide gels. Individual blots were probed with sera and urine from 2 late TB patients and 2 PPD+ healthy controls. Sera and urine samples from the healthy controls showed cross-reactivity with the 30-32 and the 65 kDa proteins as discussed above. As expected, the serum samples (tested at 1:100 dilution) from the smear positive (=late) TB patients reacted strongly with several protein bands between 20-120 kDa, and reactivity with the 88 kDa (GlcB) band was clearly discernable. The reactivity of sera with MPT 51, MPT 32 and the Ag 85C is difficult to ascertain on 1-D blots due to the presence of several other proteins with similar molecular weights.

Urine samples from the TB patients (tested undiluted) reacted with a similar profile of antigens, albeit less well. The 88 kDa protein GlcB was recognized by antibodies in both urine samples, but the reactivity of the urine samples with MPT 32, Ag 85C and MPT 51 could not be ascertained on 1-D blots. However, ELISA results showed that anti-MPT 32 antibodies are present in the urine. This suggests that the antibodies in the urine are directed against the same antigens as are those in the serum, although antibody titers are lower. Together, these results indicate that (1) Anti-mycobacterial antibodies are present in the urine of a significant proportion of smear positive (late) TB patients, thereby serving as the basis for a urine based diagnostic test for TB.
(2) An antibody detection based on testing both urine and serum for anti-mycobacterial antibodies significantly enhances the value of the diagnostic test. Increased sensitivity by using both body fluids is be especially important for diagnosis of early TB in smear negative (=early) subjects in whom the sensitivity of antibody detection with the current serodiagnostic test is 50% and in HIV-infected TB patients in whom the current sensitivity is 66%.
(3) A urine or urine/serum based diagnostic test for TB is performed using the same antigens of Mtb described herein (as well as others) including full length proteins, polyproteins, peptides, and peptide multimers, that are identified as seroreactive.

EXAMPLE VIII

Anti-Mycobacterial Antibodies in Nonhuman Mammals

In order to determine which antigens in the culture filtrates of *M. tuberculosis* are recognized by non-human mammals who have TB, the following experiment was performed. Sera were obtained from 2 guinea-pigs that had been infected by 4-5 colony forming units of aerosolized virulent Mtb. Guinea-pigs infected by the above protocol develop TB in 14-15 weeks. The infected animals were bled at 15 weeks post-infection, and the sera were used to probe western blots prepared from culture filtrates fractionated in 12% SDS-PAGE. Sera from 2 uninfected guinea-pigs were included as negative controls. Sera from 2 human TB patients were included for comparison. Sera from healthy individuals cross-react with antigens of 65 kDa and 30-32 kDa in Mtb culture filtrates. Sera from the Mtb infected guinea-pigs showed strong reactivity with several antigens in the culture filtrate that were not recognized by the control sera. Thus, the sera from the tuberculosis animals showed strong reactivity with the 88 kDa protein GlcB described above, the 42-45 kDa protein, the 38 kDa protein, and with several other protein bands. This same antigen profile is recognized by the sera from human TB patients.

These results show that the antigen profile recognized by sera from mammals with TB is the same as the profile recognized by human TB patients. Therefore, the proteins and peptides that are defined herein as being useful for serodiagnosis of TB or TB vaccines in humans can also be the basis of serodiagnostic assays and vaccines for TB in other mammals. The present invention is useful in the veterinary medical setting as well.

EXAMPLE IX

Seroreactive Peptides of "Early" Mtb Protein Antigens

A study was performed that was designed first to predict and test epitopes of the Mtb 88 kDa GlcB protein and of the MPT51 protein that should be antigenic and react with early antibodies of Mtb-infected subjects, making them useful in a serodiagnostic test for early TB in place of the full length native (or recombinant) molecules. The amino acid sequence was subjected to analysis by several different algorithms and approaches that can be used broadly to test other Mtb proteins in the same way (PCGENE, Hydropathy, etc.)

The Hopp-Woods method was described in Hopp, T P & Woods, K R, *Proc Natl Acad Sci USA,* 1981, 78:3824-3828; Hopp & Woods, *Mol Immunol,* 1983 20:483-489). The method locates protein antigenic determinants by analyzing amino acid sequences in order to find the point of greatest local hydrophilicity. This is accomplished by assigning each amino acid a numerical value (hydrophilicity value) and then repetitively averaging these values along the peptide chain. The point of highest local average hydrophilicity is invariably located in, or immediately adjacent to, an antigenic determinant. The prediction success rate depends on averaging group length, with hexapeptide averages yielding optimal results. The method was originally developed using 12 proteins for which extensive immunochemical information was available and subsequently was used to predict antigenic determinants The 1983 publication describes a computerized method for predicting the locations of protein antigenic determinants which requires only amino acid sequence information. This procedure was used to predict the major antigenic determinant of the hepatitis B surface antigen, and is suitable for use on personal computers (having been written in BASIC to make it available to investigators with limited computer experience and/or resources. This document also demonstrated a means of locating multiple antigenic sites on a homologous series of proteins using influenza hemagglutinin.

Another approach to analyze "flexibility" of the molecules is the Karplus-Stultz method (Stultz C M, Karplus M., *Proteins* 2000 40:258-289). This is based on the dynamic ligand design (DLD) algorithm, an automated method for the creation of novel ligands. The algorithm links up small functional groups that have been placed in energetically favorable positions in the binding site of a target molecule. The positions and orientations of the small functional groups can be determined using the multi-copy simultaneous search approach (or experimental data). A novel simulated annealing protocol can be used to optimize the pseudo-potential energy of ligands in the binding site.

The approach of Jameson and colleagues was used to predict the antigenic regions of the molecule. Jameson B A & Wolf H, *Comput Appl Biosci* 1988 4:181-186 introduced a computer algorithm for predicting topological features of a protein directly from its primary amino acid sequence. The computer program generates values for surface accessibility parameters and combines these values with those obtained for regional backbone flexibility and predicted secondary structure. The output of this algorithm, the antigenic index, is used to create a linear surface contour profile of the protein. Because most, if not all, antigenic sites are located within surface exposed regions of a protein, the program offers a reliable means of predicting potential antigenic determinants. The approach was tested on well-characterized proteins and yielded a strong correlation between the predicted antigenic index and known structural and biological data. In a companion publication, Wolf, H. et al., *Comput Appl Biosci* 1988, 4:187-19 presented an integrated family of amino acid sequence analysis programs. Because exact 3-dimensional structures are available for very few proteins with known sequences, it was preferred to use the primary amino acid directly to predict important structural parameters. The authors introduce a broad-based, user-defined analysis of amino acid sequence information based on published algorithms, designed to access standard protein data bases, calculate hydropathy, surface probability and flexibility values and perform secondary structure predictions. The data output was characterized as an 'easy-to-read' graphic format and several parameters could be superimposed within a single plot in order to simplify data interpretations. This package included a novel algorithm for the prediction of potential antigenic sites. Thus the software package offers a powerful tool to analyze an amino acid sequence for antigenic site analyses. These algorithms were written to function in context with the UWGCG (Univ of Wisconsin Genetics Computer Group) program collection.

For the present invention, the foregoing analyses were done in collaboration with Macromolecular Resources, Inc. (Sigma/Genosys) who also synthesized the peptides described below (to a purity of 95%). Biotinylated peptides representing several of the epitopes were synthesized, and reactivity of these peptides with sera from TB patients and PPD positive and PPD negative healthy controls was evaluated. Each of the peptides were recognized by antibodies from different patients.

TABLE 10

Identification of Peptides of 88 kDa Protein Bearing Early TB Immunoreactive Epitopes

| | SEQ ID NO: | Fraction of reacting sera | |
|---|---|---|---|
| | | TB | control |
| Peptides of 88 kDa protein* SEQ ID NO: 106 Genbank #CAB01465 | | | |
| 5274 CGTDGAEKGPTYNKVRGDK aa 151-167* | 108 | 25/57 | 1/40 |
| 5275 KIGIMDEERRTTVNLKAC aa 428-445 | 109 | 4/24 | 1/24 |
| 5276 ELAWAPDEIREEVDNNC aa 586-603 | 110 | 21/57 | 1/40 |
| 5277 LHRRRREFKARAAEKPAPSDRAG aa 715-736 | 111 | 3/24 | 1/24 |
| 5936 ARDELQAQIDKWHRRR aa 56-71 | 112 | 22/57 | 1/40 |
| 5937 LNRDRNYTAPGGGQ aa 314-327 | | | |

TABLE 10-continued

Identification of Peptides of 88 kDa Protein Bearing Early TB Immunoreactive Epitopes

| | SEQ ID NO: | Fraction of reacting sera | |
|---|---|---|---|
| | | TB | control |
| Peptide from MPT51 SEQ ID NO: 107 (Genbank #CAA05211) | | | |
| 5939 GAPQLGRWKWHDPWV aa 167-181 | 114 | 10/57 | 1/40. | a PPD+ TB patient sera
b PPD+ control sera
c Similar studies were done with the MPT51. For MPT51
*N-terminal C and G (underscored) were added; not part of native protein sequence. Amino acid numbers (aa 51 . . . , etc.) denote location in full length sequence to which the peptide corresponds The following method was used. 50 µl of biotinylated peptides in blocking buffer (7.5% fetal calf serum, 2.5% BSA) were pipetted into each well of a streptavidin-coated microtiter plate. 50 µl serum were added per well and allowed to incubate for 1 hour at room temperature. Plates were washed 4 times with 0.05% PBST. 100 µl of anti-human antibody were added and allowed to incubate for 1 hour at room temperature. Plates were then washed with Tris buffer, six times and substrate and amplifier added. Absorbance of the colored reaction product was read on an microplate reader at a wavelength of 490 nm.

Results are shown in Table 10, below which records the peptides to which reactivity was observed. Reactivity is indicated as the fraction of TB sera that reacted positively (absorbance>2.5 standard deviations above the negative control sera). Sera were assayed against the peptides at multiple dilutions; optimal responses were usually observed at a 1/10 dilution, though 1/5 and 1/20 dilutions were also tested.

It was concluded that five peptides from GlcB and one peptide from MPT51 were antigenic with respect to early TB sera and are therefore useful in the present diagnostic compositions and methods, kits, and as vaccine compositions.

EXAMPLE X

Identification of Epitope-Bearing Peptides of Mtb Protein GlcB Using SPOTs Technology The SPOTS epitope mapping technology (Sigma Genosys) was used to identify additional epitopes on the GlcB protein (=88 kDa protein). For technical details, see *Sigma Genosys Custon SPOTs Technical Manual*, v. 1.1 (available at the URL on the Worldwide Web: genosys.com).

A custom library of 13-mer peptides, overlapping by 7 amino acids, and attached covalently to a pre-derivatized cellulose membrane was synthesized by Sigma Genosys in accordance with the present inventors' instructions. The sequences of the 122 peptides, spanning the entire protein are shown in Table 11, below. The membrane was used for colorimetric detection of immunoreactivity. After regeneration, the free immobilized peptides are "regenerated" and a second and subsequent antibody or antiserum is applied. Thus, different patterns are obtained on the identical peptide matrix and can be compared qualitatively and quantitatively.

For mapping, the membrane was rinsed briefly in methanol, and washed thrice (10 min each) in Tris-buffered saline.

The membrane was blocked overnight at room temperature with a casein-containing blocking agent provided by the Sigma Genosys. After blocking, the membrane was washed with Tris-buffered saline containing Tween-20 (0.05%) and exposed to 1:100 dilution of a serum pool prepared from sera of 6 patients with confirmed, smear-positive TB.

To identify the reactive peptides, the overlapping peptide library was incubated with the pooled serum for 4 hrs, washed and probed with 1a:200 dilution of β-galactosidase-conjugated anti-human IgG. After this incubation the membrane was washed and exposed to the substrate for β-galactosidase (X-gal in N,N'-dimethyl formamide (DMF). The membrane could be regenerated for reuse by washing extensively in deionized water (30 min, 3 changes), and then in DMF before stripping with buffer A (urea 48% w/v, SDS, 1% w/v, and β-mercaptoethanol, 1/1000 dilution of the neat reagent) and buffer B (50% ethanol/10% acetic acid (v/v)). Once the previously deposited substrate was removed, the membrane was re-blocked again and probed as above using a serum pool obtained from 6 PPD skin test-positive healthy individuals. This pooled serum was also diluted 1:100. The same 2 pools (TB patients and healthy controls) were also tested at twice the concentration (i.e., 1:50 dilution). As a controls the membrane was probed with the β-galactosidase-conjugated anti-human IgG (without prior exposure to the human serum) to identify peptides that bind non-specifically to the secondary antibody (or enzyme).

Based on the reactivity of the 122 overlapping peptides (SEQ ID NO:116-237) with the pooled sera, the following peptides were identified as being strongly immunogenic in TB patients: SEQ ID NO:117; SEQ ID NO:126; SEQ ID NO:127; SEQ ID NO:128; SEQ ID NO:134; SEQ ID NO:135; SEQ ID NO:136; SEQ ID NO:137; SEQ ID NO:138; SEQ ID NO:154; SEQ ID NO:155; SEQ ID NO:170; SEQ ID NO:172; SEQ ID NO:191; SEQ ID NO:216; and SEQ ID NO:217.

These sequences represent peptides that comprise strongly recognized epitopes (2-5× more intense staining with TB serum pool vs. control. This is in addition to those epitopes identified earlier on the basis of computer algorithms and found to be immunogenic in patients (see Example IX).

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

TABLE 11

Analysis of Overlapping Peptide Sequences* of the GlcB

| SEQUENCE | SEQ ID NO | SEQUENCE | SEQ ID NO: | SEQUENCE | SEQ ID NO: | SEQUENCE | SEQ ID NO: |
|---|---|---|---|---|---|---|---|
| 1. MTDRVSVGNLRIA | 116 | 32. FGDATGFTVQDGQ | 147 | 62. IHGLKASDVNGPL | 178 | 92. LHYHQVDVAAVQQ | 208 |
| 2. VGNLRIARVLYDF | 111 | 33. FTVQDGQLVVALP | 148 | 63. SDVNGPLINSRTG | 179 | 93. DVAAVQQGLAGKR | 209 |
| 3. ARVLYDFVNNEAL | 118 | 34. QLVVALPDKSTGL | 149 | 64. LINSRTGSIYIVK | 180 | 94. QGLAGKRRATIEQ | 210 |
| 4. FVNNEALPGTDID | 119 | 35. PDKSTGLANPGQF | 150 | 65. GSIYIVKPKMHGP | 181 | 95. RRATIEQLLTIPL | 211 |
| 5. LPGTDIDPDSFWA | 120 | 36. LANPGQFAGYTGA | 151 | 66. KPKMHGPAEVAFT | 182 | 96. QLLTIPLAKELAW | 212 |
| 6. DPDSFWAGVDKVV | 121 | 37. FAGYTGAAESPTS | 152 | 67. PAEVAFTCELFSR | 183 | 97. LAKELAWAPDEIR | 213 |
| 7. AGVDKVVADLTPQ | 122 | 38. AAESPTSVLLINH | 153 | 68. TCELFSRVEDVLG | 184 | 98. WAPDEIREEVDNN | 214 |
| 8. VADLTPQNQALLN | 123 | 39. SVLLINHGLHIEI | 154 | 69. RVEDVLGLPQNTM | 185 | 99. REEVDNNCQSILG | 215 |
| 9. QNQALLNARDELQ | 124 | 40. HGLHIEILIDPES | 155 | 70. GLPQNTMKIGIMD | 186 | 100. NCQSILGYVVRWV | 216 |
| 10. NARDELQAQIDKW | 125 | 41. ILIDPESQVGTTD | 156 | 71. MKIGIMDEERRTT | 187 | 101. GYVVRWVDQGVGC | 217 |
| 11. QAQIDKWHRRRVI | 126 | 42. SQVGTTDRAGVKD | 157 | 72. DEERRTTVNLKAC | 188 | 102. VDQGVGCSKVPDI | 218 |
| 12. WHRRRVIEPIDMD | 127 | 43. DRAGVKDVILESA | 158 | 73. TVNLKACIKAAAD | 189 | 103. CSKVPDIHDVALM | 219 |
| 13. IEPIDMDAYRQFL | 128 | 44. DVILESAITTIMD | 159 | 74. CIKAAADRWFIN | 190 | 104. IHDVALMEDRATL | 220 |
| 14. DAYRQFLTEIGYL | 129 | 45. AITTIMDFEDSVA | 160 | 75. DRVVFINTGFLDR | 191 | 105. MEDRATLRISSQL | 221 |
| 15. LTEIGYLLPEPDD | 130 | 46. DFEDSVAAVDAAD | 161 | 76. NTGFLDRTGDEIH | 192 | 106. LRISSQLLANWLR | 222 |
| 16. LLPEPDDFTITTS | 131 | 47. AAVDAADKVLGYR | 162 | 77. RTGDEIHTSMEAG | 193 | 107. LLANWLRHGVITS | 223 |
| 17. DFTITTSGVDAEI | 132 | 48. DKVLGYRNWLGLN | 163 | 78. HTSMEAGPMVRKG | 194 | 108. RHGVITSADVRAS | 224 |
| 18. SGVDAEITTTAGP | 133 | 49. RNWLGLNKGDLAA | 164 | 79. GPMVRKGTMKSQP | 195 | 109. SADVRASLERMAP | 225 |
| 19. ITTTAGPQLVVPV | 134 | 50. NKGDLAAAVDKDG | 165 | 80. GTMKSQPWILAYE | 196 | 110. SLERMAPLVDRQN | 226 |
| 20. PQLVVPVLNARFA | 135 | 51. AAVDKDGTAFLRV | 166 | 81. PWILAYEDHNVDA | 197 | 111. PLVDRQNAGDVAY | 227 |
| 21. VLNARFALNAANA | 136 | 52. GTAFLRVLNRDRN | 167 | 82. EDHNVDAGLAAGF | 198 | 112. NAGDVAYRPMAPN | 228 |

TABLE 11-continued

Analysis of Overlapping Peptide Sequences* of the GlcB

| SEQUENCE | SEQ ID NO | SEQUENCE | SEQ ID NO: | SEQUENCE | SEQ ID NO: | SEQUENCE | SEQ ID NO: |
|---|---|---|---|---|---|---|---|
| 22. ALNAANARWGSLY | 137 | 53. VLNRDRNYTAPGG | 168 | 83. AGLAAGFSGRAQV | 199 | 113. YRPMAPNFDDSIA | 229 |
| 23. ARWGSLYDALYGT | 138 | 54. NYTAPGGGQFTLP | 169 | 84. FSGRAQVGKGMWT | 200 | 114. NFDDSIAFLAAQE | 230 |
| 24. YDALYGTDVIPET | 139 | 55. GGQFTLPGRSLMF | 170 | 85. VGKGMWTMTELMA | 201 | 115. AFLAAQELILSGA | 231 |
| 25. TDVIPETDGAEKG | 140 | 56. PGRSLMFVRNVGH | 171 | 86. TMTELMADMVETK | 202 | 116. ELILSGAQQPNGY | 232 |
| 26. TDGAEKGPTYNKV | 141 | 57. FVRNVGHLMTNDA | 172 | 87. ADMVETKIAQPRA | 203 | 117. AQQPNGYTEPILH | 233 |
| 27. GPTYNKVRGDKVI | 142 | 58. HLMTNDAIVDTDG | 173 | 88. KIAQPRAGASTAW | 204 | 118. YTEPILHRRRREF | 234 |
| 28. VRGDKVIAYARKF | 143 | 59. AIVDTDGSEVFEG | 174 | 89. AGASTAWVPSPTA | 205 | 119. HRRRREFKARAAE | 235 |
| 29. IAYARKFLDDSVP | 144 | 60. GSEVFEGIMDALF | 175 | 90. WVPSPTAATLHAL | 206 | 120. FKARAAEKPAPSD | 236 |
| 30. FLDDSVPLSSGSF | 145 | 61. GIMDALFTGLIAI | 176 | 91. AATLHALHYHQVD | 207 | 121. EKPAPSDRAGDDA | 237 |
| 31. PLSSGSFGDATGF | 146 | 62. FTGLIAIHGLKAS | 177 | | | | |

*Seroreactive peptides are shown in boldface and larger font

What is claimed is:

1. An antigenic composition useful for early detection of *M. tuberculosis* (Mtb) disease or infection or for immunizing a subject against Mtb infection, comprising (a) a peptide selected from the group consisting of:

(1) CGTDGAEKGPTYNKVRGDK; (SEQ ID NO: 108)

(2) KIGIMDEERRTTVNLKAC; (SEQ ID NO: 109)

(3) ELAWAPDEIREEVDNNC; (SEQ ID NO: 110)

(4) LHRRRREFKARAAEKPAPSDRAG; (SEQ ID NO: 111)

(5) ARDELQAQIDKWHRRR; (SEQ ID NO: 112)

(6) LNRDRNYTAPGGGQ; (SEQ ID NO: 113)

(7) GAPQLGRWKWHDPWV (SEQ ID NO: 114)

(8) VGNLRIARVLYDF; (SEQ ID NO: 117)

(9) QAQIDKWHRRRVI; (SEQ ID NO: 126)

(10) WHRRRVIEPIDMD; (SEQ ID NO: 127)

(11) IEPIDMDAYRQFL; (SEQ ID NO: 128)

(12) ITTTAGPQLVVPV; (SEQ ID NO: 134)

-continued

(13) PQLVVPVLNARFA; (SEQ ID NO: 135)

(14) VLNARFALNAANA; (SEQ ID NO: 136)

(15) ALNAANARWGSLY; (SEQ ID NO: 137)

(16) ARWGSLYDALYGT; (SEQ ID NO: 138)

(17) SVLLINHGLHIEI; (SEQ ID NO: 154)

(18) HGLHIEILIDPES; (SEQ ID NO: 155)

(19) GGQFTLPGRSLMF; (SEQ ID NO: 170)

(20) FVRNVGHLMTNDA; (SEQ ID NO: 172)

(21) DRVVFINTGFLDR; (SEQ ID NO: 191)

(22) NCQSILGYVVRWV; (SEQ ID NO: 216)
and

(23) GYVVRWVDQGVGC. (SEQ ID NO: 217)

with the proviso that said composition is not the full length protein GlcB, the sequence of which is SEQ ID NO:106, or MPT51, the sequence of which is SEQ ID NO:107;

(b) a conservative amino acid substitution variant of the peptide of (a) which retains reactivity with antibodies specific for (i) GlcB in the case of peptides (1)-(6) or (8)-(23) or (ii) MPT51 in the case of peptide (7); or (c) a combination of two or more of any of said peptides (1)-(23) of (a) or a combination of two or more of any of said variants of (b), or a combination of any one or more of said peptides of (a) and any one or more of said variants of (b).

2. An antigenic composition according to claim 1 which is a fusion polypeptide that includes:

(a) one or more of said peptides (1)-(23) and/or said variants thereof, linked to (b) one or more proteins selected from the group consisting of SEQ ID NO:106, SEQ ID NO:107 and another early Mtb antigen, wherein the fusion polypeptide includes an optional linker or linkers linking any two or more of said proteins or peptides.

3. An antigenic composition according to claim 1 which is:

(a) a peptide multimer having the formula $P^1_n$ wherein $P^1$ is any of peptides (1)-(23) and/or said variants thereof, and n=2-8, (b) a peptide multimer having the formula $P^1—X_m)_n—P^2$ wherein $P^1$ and $P^2$ are any of peptides (1)-(23) and/or said variants thereof, and wherein (i) $P^1$ and $P^2$ may be the same or different, and each occurrence of $P^1$ in the $P^1—X_m$ structure may be a different peptide or variant from its adjacent neighbor; and (ii) X is (A) $C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1 and n=1-7; or (B) $Gly_z$ wherein, z=1-6, and wherein the peptide multimer reacts with an antibody specific for said GlcB or MPT51 protein.

4. An antigenic composition according to claim 1 which is a recombinant peptide multimer having the formula:

$(P^1$-$Gly_z)_n$-$P^2$ wherein $P^1$ and $P^2$ are any of peptides (1)-(23) and/or said variants thereof, and wherein (a) $P^1$ and $P^2$ may be the same or different, and each occurrence of $P^1$ in the $P^1$-$Gly_z$ structure may be a different peptide or variant from its adjacent neighbor;

(b) n=1-100 and z=0-6, and wherein the peptide multimer reacts with an antibody specific for said GlcB or MPT51 protein.

5. A method for the early detection of Mtb disease or infection in a subject comprising assaying a biological fluid sample from a subject suspected of having active TB for the presence of antibodies specific for the composition of claim 1, wherein the presence of said antibodies is indicative of the presence of said disease or infection.

6. A method for the early detection of Mtb disease or infection in a subject comprising assaying a biological fluid sample from a subject suspected of having active TB for the presence of antibodies specific for the fusion polypeptide of claim 2, wherein the presence of said antibodies is indicative of the presence of said disease or infection.

7. A method for the early detection of Mtb disease or infection in a subject comprising assaying a biological fluid sample from a subject suspected of having active TB for the presence of antibodies specific for the peptide multimer of claim 3, wherein the presence of said antibodies is indicative of the presence of said disease or infection.

8. A method for the early detection of Mtb disease or infection in a subject comprising assaying a biological fluid sample from a subject suspected of having active TB for the presence of antibodies specific for the peptide multimer of claim 4, wherein the presence of said antibodies is indicative of the presence of said disease or infection.

9. The method of claim 5 where said biological fluid sample is taken from a subject having constitutional symptoms of tuberculosis, but before the onset of specific symptoms identifiable as advanced tuberculosis that is distinguished by (a) smear positivity of sputum or other pulmonary associated fluid for acid-fast bacilli, (b) cavitary pulmonary lesions, or both (a) and (b).

10. The method of claim 5, further comprising, before said assaying, the step of obtaining the biological fluid sample from said subject.

11. The method of claim 5 comprising, prior to said assaying step, removing from said sample antibodies specific for cross-reactive epitopes or antigens between proteins present in Mtb and in other bacterial genera.

12. The method of claim 11, wherein said removing is performed by immunoadsorption of said sample with *E. coli* antigens.

13. The method of claim 5, which further comprises assaying said sample for the presence of antibodies specific for one or more additional early antigens of *M. tuberculosis* selected from the group consisting of:

(a) Mtb protein GlcB the amino acid sequence of which is SEQ ID NO:106;

(b) Mtb protein MPT51 the amino acid sequence of which is SEQ ID NO:107;

(c) Mtb protein antigen 85C;

(d) Mtb glycoprotein antigen MPT32; and (e) a fusion protein comprising one or more of (a)-(d).

14. The method of claim 5, wherein said subject is a human.

15. The method of claim 14, wherein said subject is infected with HIV-1 or is at high risk for tuberculosis.

16. The method of claim 5 wherein said biological fluid sample is serum, urine or saliva.

17. The method of claim 14 wherein said biological fluid sample is urine.

18. The method of claim 5 that further includes performance of a test that detects Mtb bacilli in a sample of sputum or other body fluid of said subject.

19. A kit useful for early detection of Mtb disease comprising:

(a) an antigenic composition according to claim 1, in combination with (b) reagents necessary for detection of antibodies which bind to said peptides.

20. A kit useful for early detection of Mtb disease comprising:

(a) an antigenic composition according to claim 2, in combination with (b) reagents necessary for detection of antibodies which bind to said peptides.

21. A kit useful for early detection of *M. tuberculosis* disease comprising:

(a) an antigenic composition according to claim 3, in combination with (b) reagents necessary for detection of antibodies which bind to said peptides.

22. A kit useful for early detection of Mtb disease comprising:
   (a) an antigenic composition according to claim 4, in combination with
   (b) reagents necessary for detection of antibodies which bind to said peptides.

23. The kit of claim 19 further comprising one or more early antigens of Mtb.

24. The kit of claim 23 wherein said one or more early antigens is selected from the group consisting of:
   (a) Mtb protein GlcB the amino acid sequence of which is SEQ ID NO:106;
   (b) Mtb protein MPT51 the amino acid sequence of which is SEQ ID NO:107;
   (c) Mtb protein antigen 85C;
   (d) Mtb glycoprotein antigen MPT32; and
   (e) a fusion protein comprising one or more of (a)-(d).

* * * * *